(12) United States Patent
Harding et al.

(10) Patent No.: US 11,235,059 B2
(45) Date of Patent: Feb. 1, 2022

(54) AFUCOSYLATED ANTI-FGFR2IIIB ANTIBODIES

(71) Applicant: Five Prime Therapeutics, Inc., South San Francisco, CA (US)

(72) Inventors: Thomas Harding, San Francisco, CA (US); Kristen Pierce, Burlingame, CA (US); Namrata Patil, Sunnyvale, CA (US); Thomas Brennan, San Jose, CA (US); Julie Hambleton, San Francisco, CA (US)

(73) Assignee: Five Prime Therapeutics, Inc., Thousand Oaks, CA (US)

( * ) Notice: Subject to any disclaimer, the term of this patent is extended or adjusted under 35 U.S.C. 154(b) by 0 days.

(21) Appl. No.: 16/181,784

(22) Filed: Nov. 6, 2018

(65) Prior Publication Data
US 2019/0175730 A1    Jun. 13, 2019

Related U.S. Application Data

(62) Division of application No. 15/166,798, filed on May 27, 2016, now Pat. No. 10,172,937, which is a division of application No. 14/447,751, filed on Jul. 31, 2014, now abandoned.

(60) Provisional application No. 61/933,632, filed on Jan. 30, 2014, provisional application No. 61/901,732, filed on Nov. 8, 2013, provisional application No. 61/861,198, filed on Aug. 1, 2013.

(51) Int. Cl.
| | |
|---|---|
| *A61K 39/395* | (2006.01) |
| *C07K 16/28* | (2006.01) |
| *A61K 39/00* | (2006.01) |
| *A61K 33/243* | (2019.01) |
| *A61K 31/337* | (2006.01) |
| *A61K 31/513* | (2006.01) |
| *A61K 45/06* | (2006.01) |

(52) U.S. Cl.
CPC ........ *A61K 39/3955* (2013.01); *A61K 31/337* (2013.01); *A61K 31/513* (2013.01); *A61K 33/243* (2019.01); *A61K 45/06* (2013.01); *C07K 16/2863* (2013.01); *A61K 2039/505* (2013.01); *A61K 2039/507* (2013.01); *A61K 2039/54* (2013.01); *A61K 2039/545* (2013.01); *C07K 2317/24* (2013.01); *C07K 2317/41* (2013.01); *C07K 2317/732* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,591,639 A | 1/1997 | Bebbington et al. | |
| 5,707,632 A | 1/1998 | Williams et al. | |
| 5,863,888 A | 1/1999 | Dionne et al. | |
| 5,981,216 A | 11/1999 | Kenten et al. | |
| 6,342,221 B1 | 1/2002 | Thorpe et al. | |
| 6,946,292 B2 | 9/2005 | Kanda et al. | |
| 7,214,775 B2 | 5/2007 | Hanai et al. | |
| 7,297,493 B2 | 11/2007 | Lorenzi et al. | |
| 7,425,446 B2 | 9/2008 | Kanda et al. | |
| 7,708,992 B2 | 5/2010 | Hanai et al. | |
| 7,737,325 B2 | 6/2010 | Kanda et al. | |
| 7,872,016 B2 | 1/2011 | Eswarakumar et al. | |
| 8,067,232 B2 | 11/2011 | Kanda et al. | |
| 8,101,723 B2 | 1/2012 | Kim et al. | |
| 8,263,074 B2 | 9/2012 | Sun et al. | |
| 8,481,688 B2 | 7/2013 | Weng et al. | |
| 8,603,987 B2 | 12/2013 | Kim et al. | |
| 8,664,365 B2 * | 3/2014 | Luehrsen ............... | C07K 16/28 530/387.3 |
| 8,679,491 B2 | 3/2014 | Hanai et al. | |
| 8,945,572 B2 | 2/2015 | Chant et al. | |
| 9,140,689 B2 | 9/2015 | Byron et al. | |
| 9,254,288 B2 | 2/2016 | Pollock | |
| 9,260,525 B2 | 2/2016 | Chang et al. | |
| 9,382,324 B2 | 7/2016 | Kim et al. | |
| 9,415,118 B2 | 8/2016 | Batt et al. | |
| 9,481,733 B2 | 11/2016 | Ohtsaka et al. | |
| 9,498,532 B2 | 11/2016 | Batt et al. | |
| 9,714,298 B2 | 7/2017 | Ohtsuka et al. | |
| 9,834,609 B2 | 12/2017 | Kim et al. | |
| 10,172,937 B2 | 1/2019 | Harding et al. | |

(Continued)

FOREIGN PATENT DOCUMENTS

| | | |
|---|---|---|
| CN | 103096915 B | 8/2016 |
| EP | 2018442 A2 | 1/2009 |

(Continued)

OTHER PUBLICATIONS

Juntilla et al. Superior in vivo efficacy of afucosylated Trastuzumab in the treatment of HER2-amplified breast cancer. Cancer Res. 70, 4481-4489, 2010. (Year: 2010).*
Jefferis R., Antibody therapeutics: isotype and glycoform selection. Expert Opin. Biol. Ther. 7, 1401-1413, 2007. (Year: 2007).*
Brown, M. et al., "Tolerance to Single, but Not Multiple, Amino Acid Replacements in Antibody VH CDR2," J. Immunol., 156: 3285-3291, 1996.

(Continued)

*Primary Examiner* — Elly-Gerald Stoica
(74) *Attorney, Agent, or Firm* — McNeill Baur PLLC

(57) ABSTRACT

The present invention provides antibodies that bind FGFR2IIIb, wherein the antibodies are afucosylated. The present invention provides compositions comprising antibodies that bind FGFR2IIIb, wherein at least 95% of the antibodies in the composition are afucosylated. In some embodiments, methods of treating cancer comprising administering afucosylated anti-FGFR2IIIb antibodies are provided.

59 Claims, 10 Drawing Sheets

Specification includes a Sequence Listing.

(56) References Cited

U.S. PATENT DOCUMENTS

| | | | |
|---|---|---|---|
| 2005/0147612 A1 | 7/2005 | Yayon et al. | |
| 2007/0248605 A1 | 10/2007 | Hestir et al. | |
| 2009/0068110 A1 | 3/2009 | Shang et al. | |
| 2009/0170715 A1 | 7/2009 | Glinsky | |
| 2009/0311250 A1 | 12/2009 | Chant et al. | |
| 2010/0047251 A1 | 2/2010 | Yayon et al. | |
| 2010/0111944 A1 | 5/2010 | Pollock et al. | |
| 2010/0173323 A1* | 7/2010 | Strome | C07K 16/2863 435/7.1 |
| 2010/0196364 A1 | 8/2010 | Kim et al. | |
| 2011/0059091 A1 | 3/2011 | Chang et al. | |
| 2011/0091473 A1 | 4/2011 | Golab et al. | |
| 2011/0160216 A1 | 6/2011 | Lenz | |
| 2011/0305687 A1 | 12/2011 | Weng et al. | |
| 2011/0318373 A1 | 12/2011 | Sasikumar et al. | |
| 2012/0258496 A1* | 10/2012 | Ellwanger | C12N 5/067 435/69.6 |
| 2013/0142802 A1 | 6/2013 | Chang et al. | |
| 2013/0183288 A1* | 7/2013 | Reff | A61K 39/3955 424/133.1 |
| 2013/0288305 A1 | 10/2013 | Weng et al. | |
| 2013/0309250 A1 | 11/2013 | Cogswell et al. | |
| 2014/0322220 A1 | 10/2014 | Harrenga et al. | |
| 2015/0050273 A1 | 2/2015 | Harding et al. | |
| 2015/0125454 A1 | 5/2015 | Ohtsuka et al. | |
| 2015/0167101 A1 | 6/2015 | Chant et al. | |
| 2015/0210769 A1 | 7/2015 | Freeman et al. | |
| 2015/0366866 A1 | 12/2015 | Mahamed et al. | |
| 2016/0009820 A1 | 1/2016 | Ohtsuka et al. | |
| 2016/0130661 A1 | 5/2016 | Brooks et al. | |
| 2016/0287699 A1 | 10/2016 | Karkera et al. | |
| 2017/0008964 A1 | 1/2017 | Batt et al. | |
| 2017/0145102 A1 | 5/2017 | Pierce et al. | |
| 2017/0145103 A1 | 5/2017 | Pierce | |
| 2018/0094063 A1 | 4/2018 | Kim et al. | |
| 2019/0175730 A1 | 6/2019 | Harding | |

FOREIGN PATENT DOCUMENTS

| | | | |
|---|---|---|---|
| EP | 1423428 A2 | 8/2009 | |
| EP | 2046384 A2 | 12/2009 | |
| EP | 2569012 A2 | 10/2013 | |
| EP | 2603521 A2 | 10/2014 | |
| EP | 2782934 A1 | 10/2014 | |
| EP | 2837685 A1 | 2/2015 | |
| EP | 2871236 A1 | 5/2015 | |
| EP | 3008210 A1 | 4/2016 | |
| JP | 2013534922 A | 9/2013 | |
| KR | 1020040020107 | 3/2004 | |
| RU | 2009107895 A | 9/2010 | |
| TW | 201345924 A | 11/2013 | |
| TW | 201536804 A | 10/2015 | |
| TW | 201536808 A | 10/2015 | |
| WO | 0061739 | 10/2000 | |
| WO | 01079266 A1 | 10/2001 | |
| WO | 0231140 | 4/2002 | |
| WO | 2002102972 A2 | 12/2002 | |
| WO | 2003063893 A2 | 8/2003 | |
| WO | 2005066211 A2 | 7/2005 | |
| WO | 2007134210 A2 | 11/2007 | |
| WO | 07144893 A2 | 12/2007 | |
| WO | 2007144893 A2 | 12/2007 | |
| WO | 2008017963 A2 | 2/2008 | |
| WO | 2008042236 A2 | 4/2008 | |
| WO | 2008052796 A1 | 5/2008 | |
| WO | 2008065543 A2 | 6/2008 | |
| WO | 2009052830 A1 | 4/2009 | |
| WO | 09100105 A2 | 8/2009 | |
| WO | 2010040571 A2 | 4/2010 | |
| WO | 2010054265 | 5/2010 | |
| WO | 11025814 A1 | 3/2011 | |
| WO | 2011088196 A2 | 7/2011 | |
| WO | 2011143318 A2 | 11/2011 | |
| WO | 2011161699 A2 | 12/2011 | |
| WO | 2012021841 A2 | 2/2012 | |
| WO | WO2012045085 * | 4/2012 | C07K 16/28 |
| WO | 2012162561 A2 | 11/2012 | |
| WO | 2012162561 A3 | 5/2013 | |
| WO | 2013076186 A1 | 5/2013 | |
| WO | 2013087716 A3 | 6/2013 | |
| WO | 2013154206 A1 | 10/2013 | |
| WO | WO2013148263 * | 10/2013 | C07K 16/00 |
| WO | 2014089193 A1 | 6/2014 | |
| WO | 2014160160 A2 | 10/2014 | |
| WO | 2014179448 | 11/2014 | |
| WO | 2014197937 A1 | 12/2014 | |
| WO | 2015017600 A1 | 2/2015 | |
| WO | 2015112900 A1 | 7/2015 | |
| WO | 2015116868 A2 | 8/2015 | |
| WO | 2016100882 A1 | 6/2016 | |

OTHER PUBLICATIONS

"Monoclonal Anti-human FGF R2 Antibody," R&D Systems Product Description, Catalog No. MAB665, Clone 98707, Lot No. DWH02, printed Mar. 1, 2005, 2 pages.

"Potelligent® CHOK1SV." LONZA. Web.

ACTIP, monoclonal antibodies approved by the EMA and FDA for therapeutic use, available at: http://www.ACTIP.org/products/monoclonal-antibodies-approved-by-the-ema-and-fda-for-therapeutic-use/, 10 pages, last viewed May 18, 2018.

Adelaide et al., "Integrated Profiling of Basal and Luminal Breast Cancers," Cancer Res., 67:11565-11575, (2007).

Bai et al., "GP369, an FGFR2-IIIb-specific antibody, exhibits potent antitumor activity against human cancers driven by activated FGFR2 signaling," Cancer Res., 70:7630-7639, (2010).

Beer et al., "Expression and Function of Keratinocyte Growth Factor and Activin in Skin Morphogenesis and Cutaneous Wound Repair," Journal of Investigative Dermatology Symposium Proceedings, 5:34-39 (2000).

Beer et al., "Fibroblast Growth Factor (FGF) Receptor 1-IIIb Is a Naturally Occurring Functional Receptor for FGFs That is Preferentially Expressed in the Skin and the Brain," J Biol Chem, 275:16091-16097 (2000).

Byron et al., "Inhibition of Activated Fibroblast Growth Factor Receptor 2 in Endometrial Cancer Cells Induces Cell Death Despite PTEN Abrogation," Cancer Res., 68:6902-6907, (2008).

Campbell, "General properties and applications of monoclonal antibodies," Monoclonal Antibody Technology, pp. 1-32, (1984).

Carter et al., "Identification and validation of cell surface antigens for antibody targeting in oncology," Endocrine-Related Cancer, 11:659-687, (2004).

Casset, F. et al., "A Peptide Mimetic of an Anti-CD4 Monoclonal Antibody by Rational Design," Biochem. Biophys. Res. Comm., 307: 198-205 (2003).

Catenacci, D.V.T. et al. "Updated antitumor activity and safety of FPA144, an ADCC-enhanced, FGFR2b isoform-specific monoclonal antibody, in patients with FGFR2b+ gastric cancer" 2017 ASCO Annual Meeting, Abstract No. 4067, J. Clin. Oncol. 35(Suppl): Abst. 4067 (May 17, 2017).

Catenacci, D.V.T. et al. "Updated antitumor activity and safety of FPA144, an ADCC-enhanced, FGFR2b isoform-specific monoclonal antibody, in patients with FGFR2b+ gastric cancer" 2017 ASCO Annual Meeting, Poster No. 4067, (Jun. 2, 2017).

Chen, Y. et al., "Selection and Analysis of an Optimized Anti-VEGF Antibody: Crystal Structure of an Affinity-matured Fab in Complex with Antigen," J. Mol. Biol., 293: 865-881 (1999).

Cho et al., "Enhanced Expression of Keratinocyte Growth Factor and Its Receptor Correlates with Venous Invasion in Pancreatic Cancer," Am. J. Pathol., 170(6):1964-1974, doi: http://dx.doi.org/10.2353/ajpath.2007.060935, (2007).

Clarivate Analytics, Cortellis internet portal printed pages (https://www.cortellis.com/intelligence/advsearch/view.do), two pages, Jul. 20, 2018.

Clarivate Analytics, Cortellis search results for search query: (afucosyl* or non-fucosyl* or non fucosylation) and monocolonal and antibody, four pages, Jul. 20, 2018.

(56) References Cited

OTHER PUBLICATIONS

Davies et al., "Somatic Mutations of the Protein Kinase Gene Family in Human Lung Cancer," Cancer Res., 65:7591-7595, (2005).
Davies, J. et al., "Affinity Improvement of Single Antibody VH Domains: residues in all three hypervariable regions affect antigen binding," Immunotech., 2: 169-179 (1996).
De Moerlooze et al., "An important role for the IIIb isoform of fibroblast growth factor receptor 2 (FGFR2) in mesenchymal-epithelial signalling during mouse organogenesis," Development, 127:483-492, (2000).
De Pascalis et al., "Grafting of abbreviated complementarity determining regions containing specificity determining residues essential for ligand contact to engineer a less immunogenic humanized monoclonal antibody," Journal of Immunology, 169: 3076-3084, (2002).
Declaration of Dr. Kristen Pierce, Sep. 15, 2017.
Dr. Kristen Pierce 2017 CV.
Dutt et al., "Drug-sensitive FGFR2 mutations in endometrial carcinoma," Proc Natl Acad Sci USA, 105:8713-7, (2008).
Easton et al., "Genome-wide Association Study Identifies Novel Breast Cancer Susceptibility Locus," Nature, 447:1087-1093, (2007).
Eswarakumar, V.P. et al. "Cellular signaling by fibroblast growth factor receptors" Cytokine & Growth Factor Reviews 16: 139-149 (2005).
Finch and Rubin, "Keratinocyte Growth Factor Expression and Activity in Cancer: Implications for Use in Patients with Solid Tumors," Journal of the National Cancer Institute, 98:812-824 (2006).
Fortin, D. et al., "Distinct Fibroblast Growth Factor (FGF)/FGF Receptor Signaling Pairs Initiate Diverse Cellular Responses in the Oligodendrocyte Lineage," J. Neurosci., 25(32): 7470-7479 (2005).
Genbank Accession No. AAF26719, "Fibroblast growth factor receptor 2 IIIb [Ovis aries]," Nov. 17, 2000 (1 page).
Genbank Accession No. ABI81225, "Fibroblast growth factor receptor 1 IIIc [Ovis aries]," Mar. 5, 2008 (1 page).
Gong et al., "Increased in vivo effector function of human IgG4 isotype antibodies through afucosylation," Monoclonal Antibodies 8(6): 1098-1106 (2016).
Gratz, G. "Final Report: A Twenty-eight Day Intravenous Toxicity Study of FPA144-A and FPA144-F in Cynomolgus Monkeys, Study No. 0787-12157," Test Facility: BASi, Mt. Vernon, IN, report completed Jun. 27, 2014 (295 pages).
Gratz, G. "Final Report: A Twenty-eight Day Intravenous Toxicity Study of FPA144-A and FPA144-F in Rats, Study No. 0787-12212," Test Facility: BASi, Mt. Vernon, IN, report completed Jun. 27, 2014 (483 pages).
Gratz, G. "Final Report: Single Dose Intravenous Pharmacokinetic Study of FPA144-A and FPA144-F in Cynomolgus Monkeys, Study No. 0787-12156," Test Facility: BASi, Mt. Vernon, IN, report completed Jun. 26, 2014 (133 pages).
Grose et al., "The Role of Fibroblast Growth Factor Receptor 2b in Skin Homeostasis and Cancer Development," The Embo Journal, 26:1268-1278 (2007).
Grose, R. et al., "Fibroblast Growth Factor Signaling in Tumorigenesis," Cytokine & Growth Factor Reviews, 16: 179-186 (2005).
Hattori et al., "Immunohistochemical detection of K-sam protein in stomach cancer," Clin Cancer Res, 2:1373-81, (1996).
Holt, L. et al., "Domain Antibodies: proteins for therapy," TRENDS in Blotech., 21(11): 484-490 (2003).
Hughes, "Differential Expression of the Fibroblast Growth Factor Receptor (FGFR) Multigene Family in Normal Human Adult Tissues," J Histochem cytochem, 45:1005-1019 (1997).
Hunter et al., "A Genome-Wide Association Study Identifies Alleles in FGFR2 Associated With Risk of Sporadic Postmenopausal Breast Cancer," Nature Genetics, 39:870-874, (2007).
Ibrahimi et al., "Biochemical Analysis of Pathogenic Ligand-Dependent FGFR2 Mutations Suggests Distinct Pathophysiological Mechanisms for Craniofacial and Limb Abnormalities," Human Molecular Genetics, 13:2313-2324, (2004).
International Search Report and Written Opinion of the International Searching Authority for International Application No. PCT/US2014/049008, dated Nov. 11, 2014.
Itoh et al., "Preferential Alternative Splicing in Cancer Generates a K-sam Messenger RNA with Higher Transforming Activity," Cancer Res., 54:3237-3241, (1994).
Jang et al., "Mutations in Fibroblast Growth Factor Receptor 2 and Fibroblast Growth Factor Receptor 3 Genes Associated with Human Gastric and Colorectal Cancers," Cancer Res., 61 :3541-3543, (2001 ).
Junttila, T. et al., "Superior In vivo Efficacy of Afucosylated Trastuzumab in the Treatment of HER2-Amplified Breast Cancer," Cancer Res., 70(11): 4481-4489 (2010).
Kanda et al. "Comparison of Cell Lines for Stable Production of Fucose-Negative Antibodies With Enhanced ADCC" Biotechnology and Bioengineering, 94(4): 680-688 (2006).
Katoh "Cancer genomics and genetics of FGFR2 (Review)," Int J Oncology, 33:233-237, (2008).
Keam, B. et al. "Modified FOLFOX-6 chemotherapy in advanced gastric cancer: Results of phase II study and comprehensice analysis of polymorphisms as a predictive and prognostic marker" BMC Cancer 2008, 8:148.
Kono et al., "Impaired Antibody-Dependent Cellular Cytotoxicity Mediated by Herceptin in Patients with Gastric Cancer," Cancer Res 62:5813-5817, (2002).
Von Horsten et.al. "Production of non-fucosylated antibodies by co-expression of heterologous GDP-6-deoxy-D-lyxo-4-hexulose reductase" 2010, Glycobiology, v.20 n.12 pp. 1607-1618.
W. Zhao et al., "Monoclonal Antibodies to Fibroblast Growth Factor Receptor 2 Effectively Inhibit Growth of Gastric Tumor Xenografts," Clin. Cancer Res., 16(23): 5750-5758 (2010).
Wang,L. et al., "Abstract #1236: Blocking antibody to fibroblast growth factor-2 as a potential cancer therapeutic agent," 100th AACR Annual Meeting, Apr. 18-22, 2009, Denver, CO, Cancer Res., 69:1236 (2009).
Watanabe, et al., "Overexpression of keratinocyte growth factor in cancer cells and enterochromaffin cells in human colorectal cancer," Pathology International, 50:363-372, (2000).
Wei, P. et al., "Generation and Characterization of Monoclonal Antibodies to Human Keratinocyte Growth Factor Receptor," Hybridoma, 25(3): 115-124 (2006).
Werner, "Molecular and Cellular Mechanisms of Tissue Repair", Experimental Dermatology, 14(10):786-787, (2005).
Winter, et al., "Humanized antibodies," Immunology Today, 14(6):243-246, (1993)—Ordered 6/11 from Reprints desk.
Wong et.al., "Enhancement of DNA Uptake in FUT8-Deleted CHO Cells for Transient Production of Afucosylated Antibodies" 2010, Biotechnology and Bioengineering, V.106, N.5, pp. 751-763.
Wu, H. et al., "Humanization of a Murine Monoclonal Antibody by Simultaneous Optimization of Framework and CDR Residues," J. Mol. Biol., 294: 151-162 (1999).
Yamane-Ohnuki N, et al., "Production of therapeutic antibodies with controlled fucosylation," MABS, Jun. 2009, 1(3):230-236.
Yashiro et al., "Establishment of two new scirrhous gastric cancer cell lines: analysis of factors associated with disseminated metastasis," Br J Cancer, 72:1200-1210 (1995).
Yoshino, M. et al. "Keratinocyte growth factor receptor expression in normal colorectal epithelial cells and differentiated type of colorectal cancer" Oncology Reports 13: 247-252 (2005).
Zhang et al., "Receptor specificity of the fibroblast growth factor family. The complete mammalian FGF family," J Biol Chem, 281:15694-156700, (2006).
Zhao et al., "Another Approach: Anti-FGFR2 MABs" Proc Am Assoc Cancer Res., Denver, CO Poster Presentation No. 1236, Apr. 18-22, 2009.
Zhao et al., "Monoclonal antibodies to fibroblast growth factor receptor 2 effectively inhibit growth of gastric tumor xenografts," Clin Cancer Res, 16:5750-5758, (2010).
USPTO prosecution history of U.S. Appl. No. 15/166,798.
Shields, R. L. et al. "Lack of fucose on human IgG1 N-linked oligosaccharide improves binding to human Fcgamma RIII and antibody-dependent cellular toxicity" J. Biol. Chem., vol. 277, No. 30, 2002, pp. 26733-26740.

(56) References Cited

OTHER PUBLICATIONS

Suzuki, E. et al. "A nonfucosylated anti-HER2 antibody augments antibody-dependent cellular cytotoxicity in breast cancer patients" Clin. Cancer Res., vol. 13, No. 6, 2007, pp. 1875-1882.
Kunii et al., "FGFR2-amplified gastric cancer cell lines require FGFR2 and Erbb3 signaling for growth and survival," Cancer Res, 68:2340-2348, (2008).
Kurban, et al., "Expression of keratinocyte growth factor receptor (KGFR/FGFR2 nib) in human uterine cervical cancer," Oncology Reports, 11:987-991, (2004).
Lazar, G. et al. "Engineered antibody Fc variants with enhaced effector funtion" PNAS USA 103(11): 4005-4010.
Liang et al., "Genetic Variants in Fibroblast Growth Factor Receptor 2 (FGFR2) Contribute to Susceptibility of Breast Cancer in Chinese Women," Carcinoaenesis, 29: 2341-2346, (2008).
Lo et al., Effector-attenuating substitutions that maintain antibody stability and reduce toxicity in mice, J. Biol. Chem, 292(9): 3900-08 (2017).
Luqmani et al., "Expression of Basic Fibroblast Growth Factor, FGFR1 and FGFR2 in Normal and Malignant Human Breast, and Comparison with Other Normal Tissues," Br. J. Cancer, 66:273-280, (1992).
MacCallum, R. et al., "Antibody-antigen Interactions: Contact analysis and binding site topography," J. Mol. Biol., 262: 732-745 (1996).
Masayuki et al., "AZD2171 Shows Potent Antitumor Activity Against Gastric Cancer Over-Expressing Fibroblast Growth Factor Receptor 2/Keratinocyte Growth Factor Receptor," Clinical Cancer Research, 13(10):3051-3057, (2007).
Matsunobu et al., "Expression of Keratinocyte Growth Factor Receptor Correlates with Expansive Growth and Early Stage of Gastric Cancer," International Journal of Oncology, 28:307-314, (2006).
McKay et al., "Tolerance to single, but not multiple, amino acid replacements in antibody V-HCDR2: A means of minimizing B cell wastage from somatic hypermutation?," Journal of Immunology, 156(9):3285-3291, (1996).
Miki, et al., "Determination of ligand-binding specificity by alternative splicing: Two distinct growth factor receptors encoded by a single gene," Proc. Natl. Acad. Sci. USA, Biochemistry, 89:246-250, (1992).
Mohammadi, M. et al., "Structural Basis for Fibroblast Growth Factor Receptor Activation," Cytokine & Growth Factor Reviews, 16: 107-137 (2005).
Moloney et al., "Exclusive Paternal Origin of New Mutations in Apert Syndrome," Nature Genetics, 13:48-53, (1996).
Mor et al., "DNA Amplification in Human Gastric Carcinomas," Cancer Genet Cytogenet, 65:111-114, (1993).
Mor et al., "Novel DNA Sequences at Chromosome 1 0Q26 Are Amplified in Human Gastric Carcinoma Cell Lines: Molecular Cloning by Competitive DNA Reassociation," Nucleic Acids Research, 19:117-123, (1991.
Nakamura et al., "A novel molecular targeting compound as K-samII/FGF-R2 phosphorylation inhibitor, Ki23057, for scirrhous gastric cancer," Gastroenterology, 131:1530-1541, (2006).
Nakatani et al., "Isolation of an Amplified DNA Sequence in Stomach Cancer," Jpn J. Cancer Res., 81 :707-710, (1990).
Naoko Y-O and et.al, Production of therapeutic antibodies with controlled fucosylation, MAbs, 2009; V.1, pp. 230-236.
NCT02318329, Sponsor Five Prime Therapeutics, Inc., "Open-label, dose-finding study evaluating safety and PK of FPA144 in patients with advanced solid tumors," available at clinicaltrials (dot) gov, Jan. 2017 (last viewed May 25, 2017).
Niwa R. "IgG subclass-independent improvement of antibody-dependent cellular cytotoxicity by fucose removal from Asn297-linked oligosaccharides," Journal of Immunological Methods, Sep. 22, 2005, 306:151-160.
Office Action issued in Japanese Patent Application No. 2016-531878 dated Aug. 7, 2018.

Office Action issued in Russian Patent application No. 2016106101, dated Oct. 9, 2018.
Ogle, R. et al., "Regulation of Cranial Suture Morphogenesis," Cells Tissues Organs, 176: 54-66 (2004).
Ornitz et al., "Fibroblast growth factors," Genome Biol, 2:REVIEWS3005, (2001).
Ornitz et al., "Receptor specificity of the fibroblast growth factor family," J Biol Chem, 271:15292-15297, (1996).
Otte, et al., "Expression of keratinocyte growth factor and its receptor in colorectal cancer," European Journal of Clinical Investigation, 30:222-229, (2000).
Pascal et al., "Correlation of mRNA and protein levels: Cell type-specific gene expression of cluster desianation antiaens in the prostate," BMC Genomics, 9:246, 13 pages, (2008).
PCT/US2009/063647 International Preliminary Report on Patentability and Written Opinion dated May 10, 2011.
PCT/US2009/063647 International Search Report dated Jun. 23, 2010.
Pellegrinet, L. et al. "DII1- and DII4-mediated Notch signaling are required for homeostasis of intestinal stem cells" Gastroenterology 140: 1230-1240 (2011).
Pollock et al., "Frequent activating FGFR2 mutations in endometrial carcinomas parallel germline mutations associated with craniosynostosis and skeletal dysplasia syndromes," Oncogene, 26:7158-7162, (2007).
Presta, M. et al., "Fibroblast Growth Factor/Fibroblast Growth Factor Receptor System in Angiogenesis," Cytokine & Growth Factor Reviews, 16: 159-178 (2005).
Reusch, D. et al., "Fc Glycans of Therapeutic Antibodies as Critical Quality Attributes," Glycobiol., advance access published Sep. 12, 2015, pp. 1-10 (2015).
Rudikoff et al., "Single amino acid substitution altering antigen-binding specificity," Proceedings of the National Academy of Sciences, 79:1979-1983, (1982).
Schuster, M. et al. "Improved effector functions of a therapeutic monoclonal Lewis Y-specific antibody by glycoform engineering" Cancer Res. 65(17): 7934-41 (2005).
Steele et al., "Induction of FGF receptor 2-IIIb expression and response to its ligands in epithelial ovarian cancer," Oncogene, 20:5878-5887, (2001).
Supplementary European Search Report and European Search Opinion for application EP09825523 dated May 7, 2012.
Takeda, M. et al., "AZD2171Shows Potent Antitumor Activity Against Gastric Cancer Over-Expressing Fibroblast Growth Factor Receptor 2/Keratinocyte Growth Factor Receptor," Clin. Cancer Res., 13(10): 3051-3057 (2007).
Tamaru et al., "Estrogen receptor-associated expression of keratinocyte growth factor and its possible role in the inhibition of apoptosis in human breast cancer," Lab. Invest, 84(11 ):1460-1471, (2004).
Tannheimer et al., "Characterization of Fibroblast Growth Factor Receptor 2 Overexpression in the Human Breast Cancer Cell Line SUM-52 PE," Breast Cancer Res, 2:311-320 (2000).
Trudel et al., "The inhibitory anti-FGFR3 antibody, PRO-001, is cytotoxic to t(4;14) multiple myeloma cells," Blood, 107:4039-4046, (2006).
Tsujimoto et al., "Amplification of Growth Factor Receptor Genes and DNA Ploidy Pattern in the Progression of Gastric Cancer," Virchows Arch 431 :383-389, (1997).
U.S. Appl. No. 12/614,282, Non-Final Rejection dated Apr. 7, 2011.
U.S. Appl. No. 12/614,282, Notice of Allowance dated Sep. 29, 2011.
U.S. Appl. No. 12/614,282, Requirement for Restriction/Election dated Dec. 27, 2010.
Ueda et al., "Deletion of the Carboxyl-Terminal Exons of K-sam/FGFR2 by Short Homology-Mediated Recombination, Generating Preferential Expression of Specific Messenger RNAs," Cancer Res., 59:6080-6086, (1999).
USPTO Prosecution History of U.S. Appl. No. 14/447,751.
Vajdos et al., "Comprehensive functional maps of the antigen-binding site of an anti-ErbB2 antibody obtained with shotgun scanning mutagenesis," J. Mol. Biol., 320:415-428, (2002)—Ordered 6/11 from Reprints desk.

(56) References Cited

OTHER PUBLICATIONS

Visco et al., "Expression of keratinocyte growth factor receptor compared with that of epidermal growth factor receptor and erbB-2 in endometrial adenocarcinoma," Int. J. Oncol., 15(3):431-435, doi: https://doi.org/10.3892/ijo.15.3.431, (1999).
Ahmad, Imran, et al. "Mechanisms of FGFR-mediated carcinogenesis" Biochimica et Biophysica Acta, 1823(4):850-860 (2012).
Bendell et al., FPA144-001: A First Human Study of FPA144, and ADCC-enhanced, FGFR2b Isoform-selective Monoclonal Antibody in Patients with Advanced Solid Tumors ASCO Gastrointestinal Cancers Symposium, Jan. 2016, poster #140 (Year: 2016).
Gemo, et al. "FPA144: A Therapeutic Antibody for Treating Patients with Gastric Cancers Bearing FGFR2 Gene Amplification" AACR Abstract No. 5446, Apr. 2014.
International Search Report and Written Opinion issued in PCT/US2016/063332 dated Feb. 27, 2017.
International Search Report and Written Opinion issued in PCT/US2016/063340 dated Feb. 24, 2017.
Powles et al., "MPDL3280A (anti-PD-L1) treatment leads to clinical activity in metastatic bladder cancer" Nature 515:558-563 (Year: 2014).
R&D Systems online catalog page for MAB665 dated Mar. 1, 2005.
Ricol, David et al. "Tumour suppressive properties of fibroblast growth factor receptor 2-IIIB in human bladder cancer" Oncogene 18:7234-7243 (1999).
Takeda, Masayuki et al. "AZD2171 Shows Potent Antitumor Activity Against Gastric Cancer Over-Expressing Fibroblast Growth Factor Receptor 2/Keratinocyte Growth Factor Receptor" Clinical Cancer Research, 13(10):3051-3057 (2007).
Tiong, Kai Hung et al. "Functional roles of fibroblast growth factor receptors (FGFRs) signaling in human cancers" Apoptosis 18:1447-1468 (2013).
Zhao, Wei-meng, et al. "Monoclonal Antibodies to Fibroblast Growth Factor Receptor 2 Effectively Inhibit Growth of Gastric Tumor Xenografts" Clin Cancer Res, 16(23):5750-5758 (2010).
Fedyanin M. Yu. et al., Prospects of therapeutic action on FGFR signaling pathway. Advances of molecular oncology. 2015, No. 1, pp. 27-38.
Anonymous, "Five Prime announces bemarituzumab plus chemotherapy demonstrates significant progression-free and overall survival benefit compared to placebo plus chemotherapy in front-line advanced gastric and gastrointestinal junction cancer," press release Nov. 10, 2020, available at www(dot)fiveprime(dot)com. (3 pages).
Anonymous: "Five Prime Therapeutics Initiates Phase Patient Dosing in Phase 1 Lead-In to Phase 3, Global Registrational Trial of FPA144 in Front-Line Advanced Gastric Cancer" Five Prime, Jan. 2, 2018, p. 1-2, retrieved from the internet: Retrieved from the URL:http://investor.fiveprime.com/news-releases/news-release-details/five-prime-therapeutics-initiates-patient-dosing-phase-1-lead.
Gemo, et al. "Abstract 5446: FPA144L A therapeutic antibondy for treating patients with gastric cancers bearing FGFR2 gene amplifications" Cancer Research, 74(19):1-4 (2014).
Hacibekiroglu et al., "Comparative analysis of the efficacy and safety of modified FOLFOX-6 and DCF regimens as first-line treatment in advanced gastric cancer," Mol Clin Oncol, 2015, 3:1160-1164.
International Search Report and Written Opinion for PCT/US2018/032757 dated Aug. 10, 2018.
Kim et al., "Oxaliplatin, 5-fluorouracil and leucovorin (modified FOLFOX-6) as first-line chemotherapy for advanced gastric cancer patients with poor performance status," Oncology Letters, 2012, 3:425-428.
Pectasides, D. et al. "Randomized phase III clinical trial comparing the combination of pacecitabine and oxaliplatin (CAPOX) with the combination of 5-fluorouracil, leucovorin and oxaliplatin (modified FOLFOX6) as adjuvant therapy in patients with operated high-risk stage II or stage III colorectal cancer" BMC Cancer, 15(1):384 (2015).
Sibertin-Blanc, C. et al. "Monoclonal antibodies for treating gastric cancer: promises and pitfalls", Expert Opinion on Biological Therapy. 16(6): 759-769 (2016).
Wang et al., "A phase II study of a modified FOLFOX6 regimen as neoadjuvant chemotherapy for locally advanced gastric cancer," British J Cancer, 2016, 114:1326-1333.
Yashiro, M. et al. "Synergistic antitumor effects of FGFR2 inhibitor with 5-fluorouracil on scirrhous gastric carcinoma", International Journal of Cancer, 126(4): 1004-1015 (2010).
File History of U.S. Appl. No. 15/358,756, filed Nov. 22, 2016.
File History of U.S. Appl. No. 16/613,579, filed Nov. 14, 2019.
Catenacci et al., "Phase 1 Escalation and Expansion Study of Bemarituzumab (FPA144) in Patients with Advanced Solid Tumors and FGFR2b-Selected Gastroesophageal Adenocarcinoma," J Clin Oncol, 2020, 1-10.
Five Prime Corporate Overview, "Rewriting cancer, together," Jan. 2021, 36 pages.
Wainberg et al., "Randomized Double-blind Placebo-Controlled Phase 2 Study of Bemarituzumab Combined with Modified FOLFOX6 (mFOLFOX6) in 1st Line (1L) Treatment of Advanced Gastric/Gastroesophageal Junction Adenocarcinoma (FIGHT)," Abstract, ASCO-GI, Jan. 15, 2021, 2 pages.
Wainberg et al., "A double-blind randomized study of bemarituzumab (bema) plus mFOLFOX6 versus placebo plus mFOLFOX6 as first-line treatment for advanced gastric/gastroesophageal junction cancer (FIGHT)," Late Breaking Abstract (LBA160), ASCO Gastrointestinal Cancer Symposium 2021, 15 pages.
Xiang et al., "Population pharmacokinetic analysis of phase 1 bemarituzumab data to support phase 2 gastroesophageal adenocarcinoma FIGHT trial," Cancer Chemotherapy and Pharmacology, 2020, 86:595-606.
Grothey, A., "Bemarituzumab plus modified FOLFOX6 for advanced gastric/GE junction adenocarcinoma," Oncology (/explore/channel/oncology/sp1), Expert Opinion, Interview, Feb. 10, 2021, 4 pages.
Chao, J., "Adding bemarituzumab to chemotherapy improves outcomes in certain gastric cancers," available at: www.healio.com/news/hematology-oncology/20210120/, Jan. 20, 2021, 3 pages.
Van Cutsem et al., "A randomized, open-label study of the efficacy and safety of AZD4547 monotherapy versus paclitaxel for the treatment of advanced gastric adenocarcinoma with FGFR2 polysomy or gene amplification," Anals of Oncology, 28: 1316-24 (2017).
Jefferies, Analyst Report on Five Prime Therapeutics, Inc., Nov. 10, 2020 (10 pages).
Guggenheim, Analyst Report on Five Prime Therapeutics, Inc., Nov. 11, 2020 (6 pages).
J.P. Morgan, Analyst Report on Five Prime Therapeutics, Inc., Nov. 11, 2020 (10 pages).
Amgen Press Release, "Amgen to Acquire Five Prime Therapeutics for $1.9 Billion in Cash," Mar. 4, 2021 (8 pages).
Amgen Press Release, "Amgen's Investigational Targeted Treatment Bemarituzumab Granted Breakthrough Therapy Designation," Apr. 19, 2021 (7 pages).
Zhang et al., "Research Status and Development Trend of Tumor Drugs of the FGFR Antibody Class." Biotechnology & Business, 2014, 3:7-12.
English translation of Search Report in Chinese Patent Application No. 201680067905.8., dated Mar. 19, 2021, 2 pages.
Katoh, "FGFR Inhibitors: Effects on Cancer Cells, Tumor Microenvironment and Whole-Body Homeostasis (Review)", Intl J Mol Med, 2016, 38:1-15.
File History of U.S. Appl. No. 15/358,941, filed Nov. 22, 2016.
File History of U.S. Appl. No. 17/282,589, filed Apr. 2, 2021.

* cited by examiner

G0    G1    G2

G0F    G1F    G2F

■ N-acetylglucosamine (GlcNAc)
● Mannose (Man)
○ Galactose (Gal)
▼ Fucose (Fuc)
◆ Sialic acid (Neu5Ac)

Mannose-5 (Man-5)

AFUCOSYLATED ANTI-FGFR2IIIB ANTIBODIES

This application is a Divisional of U.S. patent application Ser. No. 15/166,798, filed May 27, 2016, which is a Divisional of U.S. patent application Ser. No. 14/447,751, filed Jul. 31, 2014, which claims the benefit of priority to U.S. Provisional Application Nos. 61/861,198, filed Aug. 1, 2013; 61/901,732, filed Nov. 8, 2013; and 61/933,632, filed Jan. 30, 2014; the disclosure of each of which is incorporated herein by reference in its entirety for any purpose.

FIELD OF THE INVENTION

Afucosylated anti-FGFR2IIIb antibodies are provided.

BACKGROUND OF THE INVENTION

The fibroblast growth factor (FGF) family members bind to four known tyrosine kinase receptors, fibroblast growth factor receptors 1-4 (FGFR1-4) and their isoforms, with the various FGFs binding the different FGFRs to varying extents (Zhang et al., J. Biol. Chem. 281:15694, 2006). A protein sequence of human FGFR2 is provided in, e.g., GenBank Locus AF487553. Each FGFR consists of an extracellular domain (ECD) comprising three immunoglobulin (Ig)-like domains (D1, D2 and D3), a single transmembrane helix, and an intracellular catalytic kinase domain (Mohammadi et al., Cytokine Growth Factor Revs, 16:107, 2005). There is a contiguous stretch of acidic amino acids in the linker between D1 and D2 called the "acid box" (AB). The region containing D1 and AB is believed to be involved in auto-inhibition of the receptor, which is relieved by binding to ligand. FGFs bind to the receptors primarily through regions in D2 and D3 of the receptors. The FGFRs are characterized by multiple alternative splicing of their mRNAs, leading to a variety of isoforms (Ornitz et al., J. Biol. Chem. 271: 15292, 1996; see also Swiss-Prot P21802 and isoforms P21802-1 to -20 for sequences of FGFR2 and its isoforms). Notably, there are forms containing all three Ig domains (a isoform) or only the two Ig domains D2 and D3 domains without D1 (β isoform). In FGFR1-FGFR3, all forms contain the first half of D3 denoted Ma, but two alternative exons can be utilized for the second half of D3, leading to IIIb and IIIc forms. For FGFR2, these are respectively denoted FGFR2IIIb and FGFR2IIIc (or just FGFR2b and FGFR2c); the corresponding beta forms are denoted FGFR2(beta)IIIb and FGFR2(beta)IIIc. The FGFR2IIIb form of FGFR2 (also denoted K-sam-II) is a high affinity receptor for both FGF1 and KGF family members (FGF7, FGF10, and FGF22) whereas FGFR2IIIc (also denoted K-sam-I) binds both FGF1 and FGF2 well but does not bind the KGF family members (Miki et al., Proc. Natl. Acad. Sci. USA 89:246, 1992). Indeed, FGFR2IIIb is the only receptor for KGF family members (Ornitz et al., 1996, op. cit.) and is therefore also designated KGFR.

The FGFRs and their isoforms are differentially expressed in various tissues. FGFR2IIIb (and the IIIb forms of FGFR1 and FGFR3) is expressed in epithelial tissues, while FGFRIIIc is expressed in mesenchymal tissues (Duan et al., J. Biol. Chem. 267:16076, 1992; Ornitz et al., 1996, op. cit.). Certain of the FGF ligands of these receptors have an opposite pattern of expression. Thus, KGF subfamily members, including FGF7 (KGF), FGF10, and FGF22, bind only to FGFRIIIb (Zhang et al., op. cit.) and are expressed in mesenchymal tissues so may be paracrine effectors of epithelial cells (Ornitz et al., 1996, op. cit.). In contrast, the FGF4 subfamily members FGF4-6 bind to FGFR2IIIc and are expressed in both epithelial and mesenchymal lineages so may have either autocrine or paracrine functions. Because of the expression patterns of the isoforms of FGFR2 and their ligands, FGFR2 plays a role in epithelial-mesenchymal interactions (Finch et al., Dev. Dyn. 203:223, 1995), so it is not surprising that knock-out of FGFR2IIIb in mice leads to severe embryonic defects and lethality (De Moerlooze et al., Development 127:483, 2000).

KGF (FGF7) and KGFR (FGFR2IIIb) are overexpressed in many pancreatic cancers (Ishiwata et al., Am. J. Pathol. 153: 213, 1998), and their coexpression correlates with poor prognosis (Cho et al., Am. J. Pathol. 170:1964, 2007). Somatic mutations of the FGFR2 gene were found in 12% of a large panel of endometrial (uterine) carcinomas, and in several tested cases were required for tumor cell survival (Dutt et al., Proc. Natl. Acad. Sci. USA 105:8713, 2008). In two tumors the FGFR2 mutation was found to be the same S252W substitution associated with Apert syndrome. Amplification and overexpression of FGFR2 is associated with the undifferentiated, diffuse type of gastric cancer, which has a particularly poor prognosis, and inhibition of the FGFR2 activity by small molecule compounds potently inhibited proliferation of such cancer cells (Kunii et al., Cancer Res. 68:2340, 2008; Nakamura et al., Gastroenterol. 131:1530, 2006).

SUMMARY OF THE INVENTION

In some embodiments, an anti-FGFR2IIIb antibody is provided, wherein the heavy chain variable region comprises: (i) HVR-H1 comprising the amino acid sequence of SEQ ID NO: 6; (ii) HVR-H2 comprising the amino acid sequence of SEQ ID NO: 7; and (iii) HVR-H3 comprising the amino acid sequence of SEQ ID NO: 8; and the light chain variable region comprises: (iv) HVR-L1 comprising the amino acid sequence of SEQ ID NO: 9; (v) HVR-L2 comprising the amino acid sequence of SEQ ID NO: 10; and (vi) HVR-L3 comprising the amino acid sequence of SEQ ID NO: 11; wherein the antibody is afucosylated. In some embodiments, the antibody lack fucose at Asn297. In some embodiments, compositions comprising a plurality of anti-FGFR2IIIb antibodies are provided, wherein the heavy chain variable region of each anti-FGFR2IIIb antibody in the composition comprises: (i) HVR-H1 comprising the amino acid sequence of SEQ ID NO: 6; (ii) HVR-H2 comprising the amino acid sequence of SEQ ID NO: 7; and (iii) HVR-H3 comprising the amino acid sequence of SEQ ID NO: 8; and the light chain variable region of each anti-FGFR2IIIb antibody in the composition comprises: (iv) HVR-L1 comprising the amino acid sequence of SEQ ID NO: 9; (v) HVR-L2 comprising the amino acid sequence of SEQ ID NO: 10; and (vi) HVR-L3 comprising the amino acid sequence of SEQ ID NO: 11; wherein at least 95% of the antibodies in the composition are afucosylated. In some embodiments, the composition may be a supernatant from an antibody-producing cell line. In some embodiments, the composition may be a buffered composition. In some embodiments, the heavy chain variable domain comprises the amino acid sequence of SEQ ID NO: 4. In some embodiments, the light chain variable domain comprises the amino acid sequence of SEQ ID NO: 5. In some embodiments, the heavy chain variable domain comprises the amino acid sequence of SEQ ID NO: 4 and the light chain variable domain comprises the amino acid sequence of SEQ ID NO: 5. In some embodiments, the heavy chain comprises the amino acid sequence of SEQ ID NO: 2. In some embodiments, the light chain comprises the amino acid sequence of SEQ ID NO: 3. In some embodiments, the heavy chain comprises the amino acid sequence of SEQ ID NO: 2 and the light chain comprises the amino acid sequence of SEQ ID NO: 3. In some embodiments, a composition comprising a plurality of afucosylated anti-FGFR2IIIb antibodies is provided, wherein the antibodies compete for binding to FGFR2IIIb with an antibody comprising a heavy chain variable domain comprising the amino acid sequence of SEQ ID NO: 4 and a light chain variable domain comprising the amino acid sequence of SEQ ID NO: 5.

In some embodiments, the antibodies are monoclonal antibodies. In some embodiments, the antibodies are chimeric antibodies. In some embodiments, the antibodies are humanized antibodies. In any of the embodiments described herein, the antibodies may comprise a κ light chain constant region. In any of the embodiments described herein, the antibodies may comprise an IgG1 heavy chain constant region.

In some embodiments, the antibodies have enhanced ADCC activity in vitro compared to fucosylated anti-FGFR2IIIb antibodies having the same amino acid sequence. In some embodiments, the afucosylated anti-FGFR2IIIb antibodies cause specific lysis that is at least 10, at least 15, at least 20, at least 25, at least 30, at least 35, at least 40, at least 45, at least 50, at least 60, at least 65, at least 70, or at least 75 percentage points greater than specific lysis with fucosylated anti-FGFR2IIIb antibodies. In some embodiments, ADCC activity is determined using Ba/F3 cells expressing FGFR2IIIb as target cells and isolated human PBMCs as effector cells.

In some embodiments, the antibodies have enhanced affinity for Fc gamma RIIIA compared to fucosylated anti-FGFR2IIIb antibodies having the same amino acid sequence. In some embodiments, the afucosylated anti-FGFR2IIIb antibodies bind to Fc gamma RIIIA with at least 2-fold, at least 3-fold, at least 4-fold, at least 5-fold, at least 7-fold, at least 10-fold, at least 12-fold, at least 15-fold, at least 17-fold, or at least 20-fold greater affinity than fucosylated anti-FGFR2IIIb antibodies. In some embodiments, affinity for Fc gamma RIIIA is determined using surface plasmon resonance. In some embodiments, Fc gamma RIIIA is selected from Fc gamma RIIIA(V158) and Fc gamma RIIIA(F158). In some embodiments, Fc gamma RIIIA is Fc gamma RIIIA(V158).

In any of the embodiments described herein, the antibodies may bind FGFR2IIIb but not FGFR2IIIc. 10111 In any of the embodiments described herein, a composition comprising a plurality of afucosylated anti-FGFR2IIIb antibodies comprises at least 95% afucosylated antibodies. In any of the embodiments described herein, a composition comprising a plurality of afucosylated anti-FGFR2IIIb antibodies may have undetectable fucosylation. In some embodiments, the presence of fucose may be determined by a method comprising high performance liquid chromatography (HPLC), capillary electrophoresis, or MALDI-TOF mass spectrometry.

In some embodiments, host cells are provided that comprise nucleic acid encoding an anti-FGFR2IIIb antibody described herein, wherein the host cell lacks a functional alpha-1,6-fucosyltransferase gene (FUT8) gene. In some embodiments, the host cell is a CHO cell.

In some embodiments, methods for making afucosylated anti-FGFR2IIIb antibodies are provided. In some embodiments, a method comprises culturing a host cell under conditions suitable for expressing nucleic acid encoding the anti-FGFR2IIIb antibody, wherein the host cell lacks a functional alpha-1,6-fucosyltransferase gene (FUT8) gene. In some embodiments, a method for making afucosylated anti-FGFR2IIIb antibodies comprises culturing the host cell under conditions suitable for producing the afucosylated anti-FGFR2IIIb antibody. In some embodiments, the method further comprises recovering the anti-FGFR2IIIb antibody produced by the host cell. In some embodiments, less than 5% of the anti-FGFR2IIIb antibodies produced by the host cell comprise fucose. In some embodiments, at least 95% of the anti-FGFR2IIIb antibodies produced by the host cell lack fucose (i.e., are afucosylated). In some embodiments, fucose is undetectable in the anti-FGFR2IIIb antibodies produced by the host cell. In some embodiments, presence of fucose is detected by a method comprising HPLC, capillary electrophoresis, or MALDI-TOF mass spectrometry.

In some embodiments, pharmaceutical compositions are provided, wherein the pharmaceutical composition comprises afucosylated anti-FGFR2IIIb antibodies described herein and a pharmaceutically acceptable carrier.

In some embodiments, methods of treating cancer are provided. In some embodiments, a method comprises administering an effective amount of a pharmaceutical composition comprising afucosylated anti-FGFR2IIIb antibodies described herein and a pharmaceutically acceptable carrier. In some embodiments, the cancer is selected from gastric cancer, breast cancer, ovarian cancer, endometrial cancer, pancreatic cancer, and esophageal cancer. In some embodiments, the cancer is gastric cancer. In some embodiments, the cancer comprises an FGFR2 gene amplification. In some embodiments, FGFR2 amplification comprises FGFR2:CEN10 (chromosome 10 centromere) ratio of >3. In some embodiments, the cancer overexpresses FGFR2IIIb. In some embodiments, a cancer comprising FGFR2 amplification overexpresses FGFR2IIIb to a greater extent than FGFR2IIIc. In some embodiments, a cancer comprising FGFR2 amplification expresses FGFR2IIIb at a normalized level that is more than 2-fold, 3-fold, 5-fold, or 10-fold greater than the normalized level of FGFR2IIIc expression. In some embodiments, the expression levels are normalized to GUSB. In some embodiments, the cancer overexpresses FGFR2IIIb but does not comprise FGFR2 gene amplification. In some embodiments, expression or overexpression of FGFR2IIIb is determined by IHC. In some embodiments, 1+, 2+ or 3+ staining of tumor cells by IHC indicates FGFR2IIIb overexpression. In some embodiments, 2+ or 3+ staining in tumor cells by IHC indicates FGFR2IIIb overexpression. In some embodiments, the IHC staining is scored as described in Example 6.

In some embodiments, a method of treating cancer further comprises administering at least one additional therapeutic agent selected from a platinum agent, paclitaxel, ABRAXANE®, docetaxel, gemcitabine, capecitabine, irinotecan, epirubicin, FOLFOX, FOLFIRI, leucovorin, fluorouracil, mitomycin C, and doxorubicin hydrochloride. In some embodiments, the platinum agent is selected from cisplatin, oxaliplatin, and carboplatin. In some embodiments, a method of treating cancer further comprises administering paclitaxel. In some embodiments, a method of treating cancer further comprises administering cisplatin and/or 5-FU.

In some embodiments, uses of a pharmaceutical composition comprising afucosylated anti-FGFR2IIIb antibodies described herein and a pharmaceutically acceptable carrier are provided. In some embodiments, such use is for treating cancer in an individual with cancer. In some embodiments, the cancer is selected from gastric cancer, breast cancer, ovarian cancer, endometrial cancer, pancreatic cancer, or esophageal cancer. In some embodiments, the cancer is gastric cancer. In some embodiments, the cancer comprises an FGFR2 gene amplification. In some embodiments, FGFR2 amplification comprises FGFR2:CEN10 (chromosome 10 centromere) ratio of >3. In some embodiments, the cancer overexpresses FGFR2IIIb. In some embodiments, a cancer comprising FGFR2 amplification overexpresses FGFR2IIIb to a greater extent than FGFR2IIIc. In some embodiments, a cancer comprising FGFR2 amplification expresses FGFR2IIIb at a normalized level that is more than 2-fold, 3-fold, 5-fold, or 10-fold greater than the normalized level of FGFR2IIIc expression. In some embodiments, the expression levels are normalized to GUSB. In some embodiments, the cancer overexpresses FGFR2IIIb but does not comprise FGFR2 gene amplification. In some embodiments, expression or overexpression of FGFR2IIIb is determined by IHC. In some embodiments, 1+, 2+ or 3+ staining of tumor cells by IHC indicates FGFR2IIIb overexpression. In some embodiments, 2+ or 3+ staining in tumor cells by IHC indicates FGFR2IIIb overexpression. In some embodiments, the IHC staining is scored as described in Example 6.

In some embodiments, pharmaceutical compositions for treating cancer are provided, wherein the pharmaceutical composition comprises afucosylated anti-FGFR2IIIb antibodies described herein and a pharmaceutically acceptable carrier. In some embodiments, the cancer is selected from gastric cancer, breast cancer, ovarian cancer, endometrial cancer, pancreatic cancer, or esophageal cancer. In some embodiments, the cancer is gastric cancer. In some embodiments, the cancer comprises an FGFR2 gene amplification. In some embodiments, FGFR2 amplification comprises FGFR2:CEN10 (chromosome 10 centromere) ratio of >3. In some embodiments, the cancer overexpresses FGFR2IIIb. In some embodiments, a cancer comprising FGFR2 amplification overexpresses FGFR2IIIb to a greater extent than FGFR2IIIc. In some embodiments, a cancer comprising FGFR2 amplification expresses FGFR2IIIb at a normalized level that is more than 2-fold, 3-fold, 5-fold, or 10-fold greater than the normalized level of FGFR2IIIc expression. In some embodiments, the expression levels are normalized to GUSB. In some embodiments, the cancer overexpresses FGFR2IIIb but does not comprise FGFR2 gene amplification. In some embodiments, expression or overexpression of FGFR2IIIb is determined by IHC. In some embodiments, 1+, 2+ or 3+ staining of tumor cells by IHC indicates FGFR2IIIb overexpression. In some embodiments, 2+ or 3+ staining in tumor cells by IHC indicates FGFR2IIIb overexpression. In some embodiments, the IHC staining is scored as described in Example 6.

DETAILED DESCRIPTION OF THE INVENTION

Figure 1A:
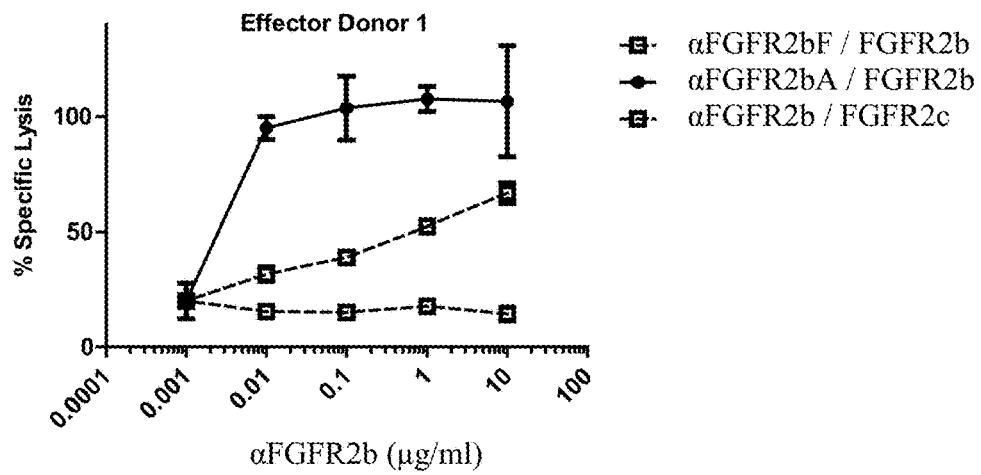
FIGS. 1A to 1C show ADCC activity of afucosylated αFGFR2bA and fucosylated αFGFR2bF against FGFR2IIIb-expressing Ba/F3 cells, as discussed in Example 3. In the legends, "αFGFR2bF/FGFR2b" indicates that fucosylated αFGFR2bF antibody was tested against FGFR2IIIb-expressing Ba/F3 target cells.

Afucosylated antibodies that bind FGFR2IIIb are provided. In some embodiments, afucosylated antibody heavy chains and light chains that are capable of forming antibodies that bind FGFR2IIIb are also provided. In some embodiments, afucosylated antibodies, heavy chains, and light chains comprising one or more particular hypervariable regions (HVRs) are provided. In some embodiments, afucosylated anti-FGFR2IIIb antibodies have enhanced ADCC activity relative to fucosylated anti-FGFR2IIIb antibodies. In some embodiments, afucosylated anti-FGFR2IIIb antibodies have enhanced affinity for Fc gamma RIIIA relative to fucosylated anti-FGFR2IIIb antibodies. In some embodiments, afucosylated anti-FGFR2IIIb antibodies have enhanced affinity for Fc gamma RIIIA(V158) relative to fucosylated anti-FGFR2IIIb antibodies. In some embodiments, afucosylated anti-FGFR2IIIb antibodies have enhanced affinity for Fc gamma RIIIA(F158) relative to fucosylated anti-FGFR2IIIb antibodies. In some embodiments, afucosylated anti-FGFR2IIIb antibodies do not bind to FGFR2IIIc.

Polynucleotides encoding antibodies that bind FGFR2IIIb are provided. Polynucleotides encoding antibody heavy chains or lights chains are also provided. Host cells that express afucosylated anti-FGFR2IIIb antibodies are provided. Methods of treatment using afucosylated antibodies to FGFR2IIIb are provided. Such methods include, but are not limited to, methods of treating cancer, such as gastric cancer, breast cancer, ovarian cancer, endometrial cancer, pancreatic cancer, and esophageal cancer.

The section headings used herein are for organizational purposes only and are not to be construed as limiting the subject matter described.

All references cited herein, including patent applications, patent publications, and Genbank Accession numbers are herein incorporated by reference, as if each individual reference were specifically and individually indicated to be incorporated by reference in its entirety.

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3rd. edition (2001) Cold Spring Harbor Laboratory Press, Cold Spring Harbor, N.Y. CURRENT PROTOCOLS IN MOLECULAR BIOLOGY (F. M. Ausubel, et al. eds., (2003)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)); Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney), ed., 1987); Introduction to Cell and Tissue Culture (J. P. Mather and P. E. Roberts, 1998) Plenum Press; Cell and Tissue Culture Laboratory Procedures (A. Doyle, J. B. Griffiths, and D. G. Newell, eds., 1993-8) J. Wiley and Sons; Handbook of Experimental Immunology (D. M. Weir and C. C. Blackwell, eds.); Gene Transfer Vectors for Mammalian Cells (J. M. Miller and M. P. Calos, eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: A Practical Approach (D. Catty., ed., IRL Press, 1988-1989); Monoclonal Antibodies: A Practical Approach (P. Shepherd and C. Dean, eds., Oxford University Press, 2000); Using Antibodies: A Laboratory Manual (E. Harlow and D. Lane (Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J.B. Lippincott Company, 1993); and updated versions thereof.

I. Definitions

Unless otherwise defined, scientific and technical terms used in connection with the present invention shall have the meanings that are commonly understood by those of ordinary skill in the art. Further, unless otherwise required by context or expressly indicated, singular terms shall include pluralities and plural terms shall include the singular.

It is understood that aspect and embodiments of the invention described herein include "consisting" and/or "consisting essentially of" aspects and embodiments. As used herein, the singular form "a", "an", and "the" includes plural references unless indicated otherwise.

In this application, the use of "or" means "and/or" unless expressly stated or understood by one skilled in the art. In the context of a multiple dependent claim, the use of "or" refers back to more than one preceding independent or dependent claim.

As is understood by one skilled in the art, reference to "about" a value or parameter herein includes (and describes) embodiments that are directed to that value or parameter per se. For example, description referring to "about X" includes description of "X".

The terms "nucleic acid molecule", "nucleic acid" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides that comprise the nucleic acid molecule or polynucleotide.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

"FGFR2IIIb" or "FGFR2b" are used interchangeably to refer to the fibroblast growth factor receptor 2 IIIb splice form. An exemplary human FGFR2IIIb is shown in GenBank Accession No. NP 075259.4, dated Jul. 7, 2013. A nonlimiting exemplary mature human FGFR2IIIb amino acid sequence is shown in SEQ ID NO: 1.

"FGFR2IIIc" or "FGFR2c" are used interchangeably to refer to the fibroblast growth factor receptor 2 Mc splice form. An exemplary human FGFR2IIIc is shown in GenBank Accession No. NP 000132.3, dated Jul. 7, 2013. A nonlimiting exemplary mature FGFR2IIIc amino acid sequence is shown in SEQ ID NO: 12.

The term "epitope" refers to a site on a target molecule (e.g., an antigen, such as a protein, nucleic acid, carbohydrate or lipid) to which an antigen-binding molecule (e.g., an antibody, antibody fragment, or scaffold protein containing antibody binding regions binds. Epitopes often consist of a chemically active surface grouping of molecules such as amino acids, polypeptides or sugar side chains and have specific three-dimensional structural characteristics as well as specific charge characteristics. Epitopes can be formed both from contiguous or juxtaposed noncontiguous residues (e.g., amino acids, nucleotides, sugars, lipid moiety) of the target molecule. Epitopes formed from contiguous residues (e.g., amino acids, nucleotides, sugars, lipid moiety) typically are retained on exposure to denaturing solvents whereas epitopes formed by tertiary folding typically are lost on treatment with denaturing solvents. An epitope may include but not limited to at least 3, at least 5 or 8-10 residues (e.g., amino acids or nucleotides). In some examples an epitope is less than 20 residues (e.g., amino acids or nucleotides) in length, less than 15 residues or less than 12 residues. Two antibodies may bind the same epitope within an antigen if they exhibit competitive binding for the antigen.

A "nonlinear epitope" or "conformational epitope" comprises noncontiguous polypeptides, amino acids and/or sugars within the antigenic protein to which an antibody specific to the epitope binds.

A "linear epitope" comprises contiguous polypeptides, amino acids and/or sugars within the antigenic protein to which an antibody specific to the epitope binds.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

The term antibody includes, but is not limited to, fragments that are capable of binding antigen, such as Fv, single-chain Fv (scFv), Fab, Fab', and (Fab')$_2$. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen. The term antibody also includes, but is not limited to, chimeric antibodies, humanized antibodies, and antibodies of various species such as mouse, human, cynomolgus monkey, etc.

The term "heavy chain variable region" refers to a region comprising heavy chain HVR1, framework (FR) 2, HVR2, FR3, and HVR3. In some embodiments, a heavy chain variable region also comprises at least a portion of an FR1 and/or at least a portion of an FR4.

The term "heavy chain constant region" refers to a region comprising at least three heavy chain constant domains, CH1, CH2, and CH3. Nonlimiting exemplary heavy chain constant regions include γ, δ, and α. Nonlimiting exemplary heavy chain constant regions also include and μ. Each heavy constant region corresponds to an antibody isotype. For example, an antibody comprising a γ constant region is an IgG antibody, an antibody comprising a δ constant region is an IgD antibody, and an antibody comprising an α constant region is an IgA antibody. Further, an antibody comprising a μ constant region is an IgM antibody, and an antibody comprising an c constant region is an IgE antibody. Certain isotypes can be further subdivided into subclasses. For example, IgG antibodies include, but are not limited to, IgG1 (comprising a $γ_1$ constant region), IgG2 (comprising a $γ_2$ constant region), IgG3 (comprising a $γ_3$ constant region), and IgG4 (comprising a $γ_4$ constant region) antibodies; IgA antibodies include, but are not limited to, IgA1 (comprising an $α_1$ constant region) and IgA2 (comprising an $α_2$ constant region) antibodies; and IgM antibodies include, but are not limited to, IgM1 and IgM2.

The term "heavy chain" refers to a polypeptide comprising at least a heavy chain variable region, with or without a leader sequence. In some embodiments, a heavy chain comprises at least a portion of a heavy chain constant region. The term "full-length heavy chain" refers to a polypeptide comprising a heavy chain variable region and a heavy chain constant region, with or without a leader sequence.

The term "light chain variable region" refers to a region comprising light chain HVR1, framework (FR) 2, HVR2, FR3, and HVR3. In some embodiments, a light chain variable region also comprises an FR1 and/or an FR4.

The term "light chain constant region" refers to a region comprising a light chain constant domain, $C_L$. Nonlimiting exemplary light chain constant regions include λ, and κ.

The term "light chain" refers to a polypeptide comprising at least a light chain variable region, with or without a leader sequence. In some embodiments, a light chain comprises at least a portion of a light chain constant region. The term "full-length light chain" refers to a polypeptide comprising a light chain variable region and a light chain constant region, with or without a leader sequence.

The term "hypervariable region" or "HVR" refers to each of the regions of an antibody variable domain which are hypervariable in sequence and/or form structurally defined loops ("hypervariable loops"). Generally, native four-chain antibodies comprise six HVRs; three in the $V_H$ (H1, H2, H3), and three in the $V_L$ (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, J. Mol. Biol. 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., Sequences of Proteins of Immunological Interest, 5th Ed. Public Health Service, National Institutes of Health, Bethesda, Md. (1991)). The terms hypervariable regions (HVRs) and complementarity determining regions (CDRs), are used herein interchangeably in reference to portions of the variable region that form the antigen binding regions.

An "acceptor human framework" for the purposes herein is a framework comprising the amino acid sequence of a light chain variable domain ($V_L$) framework or a heavy chain variable domain ($V_H$) framework derived from a human immunoglobulin framework or a human consensus framework, as defined below. An acceptor human framework derived from a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the $V_L$ acceptor human framework is identical in sequence to the $V_L$ human immunoglobulin framework sequence or human consensus framework sequence.

"Affinity" refers to the strength of the sum total of noncovalent interactions between a single binding site of a molecule (e.g., an antibody) and its binding partner (e.g., an antigen). In some embodiments, "binding affinity" refers to intrinsic binding affinity which reflects a 1:1 interaction between members of a binding pair (e.g., antibody and antigen). The affinity of a molecule X for its partner Y can generally be represented by the dissociation constant ($K_d$). Affinity can be measured by common methods known in the art, including those described herein.

An "affinity matured" antibody refers to an antibody with one or more alterations in one or more hypervariable regions (HVRs) and/or complementarity determining regions (CDRs), compared to a parent antibody which does not possess such alterations, such alterations resulting in an improvement in the affinity of the antibody for antigen.

A "chimeric antibody" refers to an antibody in which a portion of the heavy and/or light chain is derived from a particular source or species, while the remainder of the heavy and/or light chain is derived from a different source or species. In some embodiments, a chimeric antibody refers to an antibody comprising at least one variable region from a first species (such as mouse, rat, cynomolgus monkey, etc.) and at least one constant region from a second species (such as human, cynomolgus monkey, etc.). In some embodiments, a chimeric antibody comprises at least one mouse variable region and at least one human constant region. In some embodiments, a chimeric antibody comprises at least one cynomolgus variable region and at least one human constant region. In some embodiments, all of the variable regions of a chimeric antibody are from a first species and all of the constant regions of the chimeric antibody are from a second species.

A "humanized antibody" refers to an antibody in which at least one amino acid in a framework region of a non-human variable region has been replaced with the corresponding amino acid from a human variable region. In some embodiments, a humanized antibody comprises at least one human constant region or fragment thereof. In some embodiments, a humanized antibody is an Fab, an scFv, a (Fab')$_2$, etc.

An "HVR-grafted antibody" refers to a humanized antibody in which one or more hypervariable regions (HVRs) of a first (non-human) species have been grafted onto the framework regions (FRs) of a second (human) species.

A "functional Fc region" possesses an "effector function" of a native sequence Fc region. Exemplary "effector functions" include Fc receptor binding; C1q binding; CDC; ADCC; phagocytosis; down regulation of cell surface receptors (e.g. B cell receptor; BCR), etc. Such effector functions generally require the Fc region to be combined with a binding domain (e.g., an antibody variable domain) and can be assessed using various assays.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification.

"Fc receptor" or "FcR" describes a receptor that binds to the Fc region of an antibody. In some embodiments, an FcγR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. (see, e.g., Daeron, *Annu. Rev. Immunol.* 15:203-234 (1997)). FcRs are reviewed, for example, in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulation of homeostasis of immunoglobulins. Methods of measuring binding to FcRn are known (see, e.g., Ghetie and Ward., *Immunol. Today* 18(12):592-598 (1997); Ghetie et al., *Nature Biotechnology,* 15(7):637-640 (1997); Hinton et al., *J. Biol. Chem.* 279(8):6213-6216 (2004); WO 2004/92219 (Hinton et al.).

"Effector functions" refer to biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

"Human effector cells" are leukocytes which express one or more FcRs and perform effector functions. In certain embodiments, the cells express at least FcγRIII and perform ADCC effector function(s). Examples of human leukocytes which mediate ADCC include peripheral blood mononuclear cells (PBMC), natural killer (NK) cells, monocytes, macrophages, cytotoxic T cells, and neutrophils. The effector cells may be isolated from a native source, e.g., from blood.

"Antibody-dependent cell-mediated cytotoxicity" or "ADCC" refers to a form of cytotoxicity in which secreted Ig bound onto Fc receptors (FcRs) present on certain cytotoxic cells (e.g. NK cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII, and FcγRIII FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362, or U.S. Pat. No. 5,821,337, or U.S. Pat. No. 6,737,056 (Presta), may be performed. Useful effector cells for such assays include PBMC and NK cells. Alternatively, or additionally, ADCC activity of the molecule of interest may be assessed in vivo, e.g., in an animal model such as that disclosed in Clynes et al. *Proc. Natl. Acad. Sci.* (USA) 95:652-656 (1998). Additional antibodies with altered Fc region amino acid sequences and increased or decreased ADCC activity are described, e.g., in U.S. Pat. Nos. 7,923,538, and 7,994,290.

An antibody having an "enhanced ADCC activity" refers to an antibody that is more effective at mediating ADCC in vitro or in vivo compared to the parent antibody, wherein the antibody and the parent antibody differ in at least one structural aspect, and when the amounts of such antibody and parent antibody used in the assay are essentially the same. In some embodiments, the antibody and the parent antibody have the same amino acid sequence, but the antibody is afucosylated while the parent antibody is fucosylated. In some embodiments, ADCC activity will be determined using the in vitro ADCC assay as herein disclosed, but other assays or methods for determining ADCC activity, e.g. in an animal model etc., are contemplated. In some embodiments, an antibody with enhanced ADCC activity has enhanced affinity for Fc gamma RIIIA In some embodiments, an antibody with enhanced ADCC activity has enhanced affinity for Fc gamma RIIIA (V158). In some embodiments, an antibody with enhanced ADCC activity has enhanced affinity for Fc gamma RIIIA (F158).

An antibody with "altered" FcR binding affinity or ADCC activity is one which has either enhanced or diminished FcR binding activity and/or ADCC activity compared to a parent antibody, wherein the antibody and the parent antibody differ in at least one structural aspect. An antibody that "displays increased binding" to an FcR binds at least one FcR with better affinity than the parent antibody. An antibody that "displays decreased binding" to an FcR, binds at least one FcR with lower affinity than a parent antibody. Such antibodies that display decreased binding to an FcR may possess little or no appreciable binding to an FcR, e.g., 0-20% binding to the FcR compared to a native sequence IgG Fc region.

"Enhanced affinity for Fc gamma RIIIA" refers to an antibody that has greater affinity for Fc gamma RIIIA (also referred to, in some instances, as CD16a) than a parent antibody, wherein the antibody and the parent antibody differ in at least one structural aspect. In some embodiments, the antibody and the parent antibody have the same amino acid sequence, but the antibody is afucosylated while the parent antibody is fucosylated. Any suitable method for determining affinity for Fc gamma RIIIA may be used. In some embodiments, affinity for Fc gamma RIIIA is determined by a method described herein. In some embodiments, an antibody with enhanced affinity for Fc gamma RIIIA has enhanced ADCC activity. In some embodiments, an antibody with enhanced affinity for Fc gamma RIIIA has enhanced affinity for Fc gamma RIIIA(V158). In some embodiments, an antibody with enhanced affinity for Fc gamma RIIIA has enhanced affinity for Fc gamma RIIIA (F158).

"Afucosylated" antibody or an antibody "lacking fucose" refers to an IgG1 or IgG3 isotype antibody that lacks fucose in its constant region glycosylation. Glycosylation of human IgG1 or IgG3 occurs at Asn297 as core fucosylated biantennary complex oligosaccharide glycosylation terminated with up to 2 Gal residues. In some embodiments, an afucosylated antibody lacks fucose at Asn297. These structures are designated as G0, G1 ($\alpha$1,6 or $\alpha$1,3) or G2 glycan residues, depending on the amount of terminal Gal residues. See, e.g., Raju, T. S., *BioProcess Int.* 1: 44-53 (2003). CHO type glycosylation of antibody Fc is described, e.g., in Routier, F. H., *Glycoconjugate J.* 14: 201-207 (1997). In some embodiments, at least 85% of a batch of antibodies recombinantly expressed in non glycomodified CHO host cells are fucosylated at Asn297. When referring to a composition comprising a plurality of antibodies, the antibodies are considered to be afucosylated if <5% of the antibodies in the composition comprise fucose at Asn297. Methods of measuring fucose include any methods known in the art, including the methods described herein. In some embodiments, fucose is detected by the method described in Example 1. In some embodiments, fucose is undetectable in a composition comprising a plurality of afucosylated antibodies. In some embodiments, an afucosylated antibody has enhanced ADCC activity. In some embodiments, an afucosylated antibody has enhanced affinity for Fc gamma RIIIA In some embodiments, an afucosylated antibody has enhanced affinity for Fc gamma RIIIA(V158). In some embodiments, an afucosylated antibody has enhanced affinity for Fc gamma RIIIA(F158).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass), which are bound to their cognate antigen. To assess complement activation, a CDC assay, e.g., as described in Gazzano-Santoro et al., *J. Immunol. Methods* 202:163 (1996), may be performed. Antibodies with altered Fc region amino acid sequences and increased or decreased C1q binding capability are described, e.g., in U.S. Pat. Nos. 6,194,551 B1, 7,923,538, 7,994,290 and WO 1999/51642. See also, e.g., Idusogie et al., *J. Immunol.* 164: 4178-4184 (2000).

The term "substantially similar" or "substantially the same," as used herein, denotes a sufficiently high degree of similarity between two or more numeric values such that one of skill in the art would consider the difference between the two or more values to be of little or no biological and/or statistical significance within the context of the biological characteristic measured by said value. In some embodiments the two or more substantially similar values differ by no more than about any one of 5%, 10%, 15%, 20%, 25%, or 50%.

The phrase "substantially reduced," or "substantially different," as used herein, denotes a sufficiently high degree of difference between two numeric values such that one of skill in the art would consider the difference between the two values to be of statistical significance within the context of the biological characteristic measured by said values. In some embodiments, the two substantially different numeric values differ by greater than about any one of 10%, 20%, 25%, 30%, 35%, 40%, 45%, 50%, 60%, 70%, 80%, 90%, or 100%.

The terms "leader sequence" and "signal sequence" are used interchangeably to refer to a sequence of amino acid residues located at the N terminus of a polypeptide that facilitates secretion of a polypeptide from a mammalian cell. A leader sequence may be cleaved upon export of the polypeptide from the mammalian cell, forming a mature protein. Leader sequences may be natural or synthetic, and they may be heterologous or homologous to the protein to which they are attached.

A "native sequence" polypeptide comprises a polypeptide having the same amino acid sequence as a polypeptide found in nature. Thus, a native sequence polypeptide can have the amino acid sequence of naturally occurring polypeptide from any mammal. Such native sequence polypeptide can be isolated from nature or can be produced by recombinant or synthetic means. The term "native sequence" polypeptide specifically encompasses naturally occurring truncated or secreted forms of the polypeptide (e.g., an extracellular domain sequence), naturally occurring variant forms (e.g., alternatively spliced forms) and naturally occurring allelic variants of the polypeptide.

A polypeptide "variant" means a biologically active polypeptide having at least about 80% amino acid sequence identity with the native sequence polypeptide after aligning the sequences and introducing gaps, if necessary, to achieve the maximum percent sequence identity, and not considering any conservative substitutions as part of the sequence identity. Such variants include, for instance, polypeptides wherein one or more amino acid residues are added, or deleted, at the N- or C-terminus of the polypeptide. In some embodiments, a variant will have at least about 80% amino acid sequence identity. In some embodiment, a variant will have at least about 90% amino acid sequence identity. In some embodiment, a variant will have at least about 95% amino acid sequence identity with the native sequence polypeptide.

As used herein, "Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

An amino acid substitution may include but are not limited to the replacement of one amino acid in a polypeptide with another amino acid. Conservative substitutions are shown in Table 1 under the heading of "preferred substitutions". More substantial changes are provided in Table 1 under the heading of "exemplary substitutions", and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
  (1) hydrophobic: Norleucine, Met, Ala, Val, Leu, Ile;
  (2) neutral hydrophilic: Cys, Ser, Thr, Asn, Gln;
  (3) acidic: Asp, Glu;
  (4) basic: His, Lys, Arg;
  (5) residues that influence chain orientation: Gly, Pro;
  (6) aromatic: Trp, Tyr, Phe.

Non-conservative substitutions will entail exchanging a member of one of these classes for another class.

The term "vector" is used to describe a polynucleotide that may be engineered to contain a cloned polynucleotide or polynucleotides that may be propagated in a host cell. A vector may include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that may be used in colorimetric assays, e.g., β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Nonlimiting exemplary mammalian cells include, but are not limited to, NSO cells, PER.C6® cells (Crucell), and 293 and CHO cells, and their derivatives, such as 293-6E and DG44 cells, respectively.

The term "isolated" refers to a molecule that has been separated from at least some of the components with which it is typically found in nature or produced. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, e.g., in the case of an RNA polynucleotide. Thus, a DNA polynucleotide that is contained in a vector inside a host cell may be referred to as "isolated".

The terms "individual" or "subject" are used interchangeably herein to refer to an animal; for example a mammal. In some embodiments, methods of treating mammals, including, but not limited to, humans, rodents, simians, felines, canines, equines, bovines, porcines, ovines, caprines, mammalian laboratory animals, mammalian farm animals, mammalian sport animals, and mammalian pets, are provided. In some examples, an "individual" or "subject" refers to an individual or subject in need of treatment for a disease or disorder.

A "disease" or "disorder" refers to a condition where treatment is needed.

The term "cancer" refers to a malignant proliferative disorder associated with uncontrolled cell proliferation, unrestrained cell growth, and decreased cell death via apoptosis. Nonlimiting exemplary cancers include gastric cancer, breast cancer, ovarian cancer, endometrial cancer, pancreatic cancer, and esophageal cancer. In some embodiments, a cancer comprises an FGFR2 gene amplification. In some embodiments, FGFR2 amplification comprises FGFR2:CEN10 (chromosome 10 centromere) ratio of >3. In some embodiments, a cancer comprising an FGFR2 gene amplification overexpresses FGFR2IIIb. In some embodiments, a cancer comprising FGFR2 amplification overexpresses FGFR2IIIb to a greater extent than FGFR2IIIc. In some embodiments, a cancer comprising FGFR2 amplification expresses FGFR2IIIb at a normalized level that is more than 2-fold, 3-fold, 5-fold, or 10-fold greater than the normalized level of FGFR2IIIc expression. In some embodiments, the expression levels are normalized to GUSB. In some embodiments, a cancer overexpresses FGFR2IIIb but does not comprise FGFR2 gene amplification. In some embodiments, a gastric cancer comprises an FGFR2 gene amplification. In some embodiments, a gastric cancer comprising an FGFR2 gene amplification overexpresses FGFR2IIIb. In some embodiments, a gastric cancer comprising FGFR2 amplification overexpresses FGFR2IIIb to a greater extent than FGFR2IIIc. In some embodiments, a gastric cancer comprising FGFR2 amplification expresses FGFR2IIIb at a normalized level that is more than 2-fold, 3-fold, 5-fold, or 10-fold greater than the normalized level of FGFR2IIIc expression. In some embodiments, the expression levels are normalized to GUSB. In some embodiments, a gastric cancer overexpresses FGFR2IIIb but does not comprise FGFR2 gene amplification. In some embodiments, overexpression is mRNA overexpression. In some embodiments, overexpression is protein overexpression.

The term "tumor" is used herein to refer to a group of cells that exhibit abnormally high levels of proliferation and growth. A tumor may be benign, pre-malignant, or malignant; malignant tumor cells are cancerous. Tumor cells may be solid tumor cells or leukemic tumor cells. The term "tumor growth" is used herein to refer to proliferation or growth by a cell or cells that comprise a tumor that leads to a corresponding increase in the size of the tumor.

As used herein, "treatment" is an approach for obtaining beneficial or desired clinical results. "Treatment" as used herein, covers any administration or application of a therapeutic for disease in a mammal, including a human. For purposes of this invention, beneficial or desired clinical results include, but are not limited to, any one or more of: alleviation of one or more symptoms, diminishment of extent of disease, preventing or delaying spread (e.g., metastasis, for example metastasis to the lung or to the lymph node) of disease, preventing or delaying recurrence of disease, delay or slowing of disease progression, amelioration of the disease state, inhibiting the disease or progression of the disease, inhibiting or slowing the disease or its progression, arresting its development, and remission (whether partial or total). Also encompassed by "treatment" is a reduction of pathological consequence of a proliferative disease. The methods of the invention contemplate any one or more of these aspects of treatment.

In the context of cancer, the term "treating" includes any or all of: inhibiting growth of tumor cells or cancer cells, inhibiting replication of tumor cells or cancer cells, lessening of overall tumor burden and ameliorating one or more symptoms associated with the disease.

The terms "inhibition" or "inhibit" refer to a decrease or cessation of any phenotypic characteristic or to the decrease or cessation in the incidence, degree, or likelihood of that characteristic. To "reduce" or "inhibit" is to decrease, reduce or arrest an activity, function, and/or amount as compared to a reference. In certain embodiments, by "reduce" or "inhibit" is meant the ability to cause an overall decrease of 20% or greater. In another embodiment, by "reduce" or "inhibit" is meant the ability to cause an overall decrease of 50% or greater. In yet another embodiment, by "reduce" or "inhibit" is meant the ability to cause an overall decrease of 75%, 85%, 90%, 95%, or greater.

A "reference" as used herein, refers to any sample, standard, or level that is used for comparison purposes. A reference may be obtained from a healthy and/or non-diseased sample. In some examples, a reference may be obtained from an untreated sample. In some examples, a reference is obtained from a non-diseased on non-treated sample of a subject individual. In some examples, a reference is obtained from one or more healthy individuals who are not the subject or patient.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease.

As used herein, to "suppress" a function or activity is to reduce the function or activity when compared to otherwise same conditions except for a condition or parameter of interest, or alternatively, as compared to another condition. For example, an antibody which suppresses tumor growth reduces the rate of growth of the tumor compared to the rate of growth of the tumor in the absence of the antibody.

An "effective amount" of an agent refers to an amount effective, at dosages and for periods of time necessary, to achieve the desired therapeutic or prophylactic result.

A "therapeutically effective amount" of a substance/molecule of the invention, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A therapeutically effective amount may be delivered in one or more administrations.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The terms "pharmaceutical formulation" and "pharmaceutical composition" refer to a preparation which is in such form as to permit the biological activity of the active ingredient(s) to be effective, and which contains no additional components which are unacceptably toxic to a subject to which the formulation would be administered. Such formulations may be sterile.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed.

A "sterile" formulation is aseptic or essentially free from living microorganisms and their spores.

Administration "in combination with" one or more further therapeutic agents includes simultaneous (concurrent) and consecutive or sequential administration in any order.

The term "concurrently" is used herein to refer to administration of two or more therapeutic agents, where at least part of the administration overlaps in time or where the administration of one therapeutic agent falls within a short period of time relative to administration of the other therapeutic agent. For example, the two or more therapeutic agents are administered with a time separation of no more than about 60 minutes, such as no more than about any of 30, 15, 10, 5, or 1 minutes.

The term "sequentially" is used herein to refer to administration of two or more therapeutic agents where the administration of one or more agent(s) continues after discontinuing the administration of one or more other agent(s). For example, administration of the two or more therapeutic agents are administered with a time separation of more than about 15 minutes, such as about any of 20, 30, 40, 50, or 60 minutes, 1 day, 2 days, 3 days, 1 week, 2 weeks, or 1 month, or longer.

As used herein, "in conjunction with" refers to administration of one treatment modality in addition to another treatment modality. As such, "in conjunction with" refers to administration of one treatment modality before, during or after administration of the other treatment modality to the individual.

The term "package insert" is used to refer to instructions customarily included in commercial packages of therapeutic products, that contain information about the indications, usage, dosage, administration, combination therapy, contraindications and/or warnings concerning the use of such therapeutic products.

An "article of manufacture" is any manufacture (e.g., a package or container) or kit comprising at least one reagent, e.g., a medicament for treatment of a disease or disorder (e.g., cancer), or a probe for specifically detecting a biomarker described herein. In certain embodiments, the manufacture or kit is promoted, distributed, or sold as a unit for performing the methods described herein.

II. Anti-FGFR2IIIb Antibodies

In some aspects, the invention provides an afucosylated antibody directed against FGFR2IIIb. Afucosylated anti-FGFR2IIIb antibodies include, but are not limited to, humanized antibodies, chimeric antibodies, mouse antibodies, and antibodies comprising the heavy chain and/or light chain HVRs (e.g. CDRs) discussed herein. In one aspect, the invention provides isolated afucosylated antibodies that bind to FGFR2IIIb. In certain embodiments, an afucosylated anti-FGFR2IIIb antibody modulates FGFR2IIIb activity. In some embodiments, an afucosylated anti-FGFR2IIIb antibody has enhanced ADCC activity. In some embodiments, an afucosylated anti-FGFR2IIIb antibody has enhanced affinity for Fc gamma RIIIA In some embodiments, an afucosylated anti-FGFR2IIIb antibody has enhanced affinity for Fc gamma RIIIA(V158). In some embodiments, an afucosylated anti-FGFR2IIIb antibody has enhanced affinity for Fc gamma RIIIA(F158).

The anti-FGFR2IIIb antibody designated "αFGFR2b" described herein in the Examples and the sequence listing is intended to have the same amino acid sequence as antibody HuGAL-FR21 in U.S. Pat. No. 8,101,723 B2, issued Jan. 24, 2012. U.S. Pat. No. 8,101,723 B2 is specifically incorporated herein by reference for any purpose, and in particular, FIGS. 13 and 14 of U.S. Pat. No. 8,101,723 B2, which show the amino acid sequences of the variable regions and full-length mature antibody chains of HuGAL-FR21, are incorporated by reference herein for any purpose. In addition, the HVR sequences of antibody HuGAL-FR21, which are underlined in FIG. 13 of U.S. Pat. No. 8,101,723 B2, are specifically incorporated by reference herein for any purpose.

In one aspect, the invention provides an afucosylated anti-FGFR2IIIb antibody comprising at least one, two, three, four, five, or six HVRs (e.g., CDRs) selected from (a) HVR-H1 comprising the amino acid sequence of SEQ ID NO: 6; (b) HVR-H2 comprising the amino acid sequence of SEQ ID NO: 7; (c) HVR-H3 comprising the amino acid sequence of SEQ ID NO: 8; (d) HVR-L1 comprising the amino acid sequence of SEQ ID NO: 9; (e) HVR-L2 comprising the amino acid sequence of SEQ ID NO: 10; and (f) HVR-L3 comprising the amino acid sequence of SEQ ID NO: 11.

In some embodiments, an afucosylated anti-FGFR2IIIb antibody comprises a heavy chain variable region and a light chain variable region. In some embodiments, an afucosylated anti-FGFR2IIIb antibody comprises at least one heavy chain comprising a heavy chain variable region and at least a portion of a heavy chain constant region, and at least one light chain comprising a light chain variable region and at least a portion of a light chain constant region. In some embodiments, an afucosylated anti-FGFR2IIIb antibody comprises two heavy chains, wherein each heavy chain comprises a heavy chain variable region and at least a portion of a heavy chain constant region, and two light chains, wherein each light chain comprises a light chain variable region and at least a portion of a light chain constant region. In some embodiments, an afucosylated anti-FGFR2IIIb antibody comprises a heavy chain variable region comprising the amino acid sequence of SEQ ID NO: 4 and a light chain variable region comprising the amino acid sequence of SEQ ID NO: 5. In some embodiments, an afucosylated anti-FGFR2IIIb antibody comprises a heavy chain comprising the amino acid sequence of SEQ ID NO: 2 and a light chain comprising the amino acid sequence of SEQ ID NO: 3.

In one aspect, the invention provides an afucosylated anti-FGFR2IIIb antibody comprising six HVRs comprising (a) HVR-H1 comprising the amino acid sequence of SEQ ID NO: 6; (b) HVR-H2 comprising the amino acid sequence of SEQ ID NO: 7; (c) HVR-H3 comprising the amino acid sequence of SEQ ID NO: 8; (d) HVR-L1 comprising the amino acid sequence of SEQ ID NO: 9; (e) HVR-L2 comprising the amino acid sequence of SEQ ID NO: 10; and (f) HVR-L3 comprising the amino acid sequence of SEQ ID NO: 11. In some embodiments, the afucosylated anti-FGFR2IIIb antibody comprises the six HVRs as described above and binds to FGFR2IIIb. In some embodiments, the afucosylated anti-FGFR2IIIb antibody comprises the six HVRs as described above, binds to FGFR2IIIb and has at least one activity selected from enhanced ADCC activity and enhanced affinity for Fc gamma RIIIA (such as Fc gamma RIIIA(V158) and/or Fc gamma RIIIA(F158)). In some embodiments, the afucosylated anti-FGFRIIIb antibody does not bind to FGFR2IIIc.

In one aspect, the invention provides an afucosylated anti-FGFR2IIIb antibody that competes with an anti-FGFR2IIIb antibody comprising six HVRs comprising (a) HVR-H1 comprising the amino acid sequence of SEQ ID NO: 6; (b) HVR-H2 comprising the amino acid sequence of SEQ ID NO: 7; (c) HVR-H3 comprising the amino acid sequence of SEQ ID NO: 8; (d) HVR-L1 comprising the amino acid sequence of SEQ ID NO: 9; (e) HVR-L2 comprising the amino acid sequence of SEQ ID NO: 10; and (f) HVR-L3 comprising the amino acid sequence of SEQ ID NO: 11.

In one aspect, the invention provides an afucosylated antibody comprising at least one, at least two, or all three $V_H$ HVR sequences selected from (a) HVR-H1 comprising the amino acid sequence of SEQ ID NO: 6; (b) HVR-H2 comprising the amino acid sequence of SEQ ID NO: 7; and (c) HVR-H3 comprising the amino acid sequence of SEQ ID NO: 8.

In another aspect, the invention provides an afucosylated antibody comprising at least one, at least two, or all three $V_L$ HVR sequences selected from (a) HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 11.

In another aspect, an afucosylated antibody of the invention comprises (a) a $V_H$ domain comprising at least one, at least two, or all three $V_H$ HVR sequences selected from (i) HVR-H1 comprising the amino acid sequence of SEQ ID NO: 6, (ii) HVR-H2 comprising the amino acid sequence of SEQ ID NO: 7, and (iii) HVR-H3 comprising an amino acid sequence selected from SEQ ID NO: 8; and (b) a $V_L$ domain comprising at least one, at least two, or all three $V_L$ HVR sequences selected from (i) HVR-L1 comprising the amino acid sequence of SEQ ID NO: 9, (ii) HVR-L2 comprising the amino acid sequence of SEQ ID NO: 10, and (c) HVR-L3 comprising the amino acid sequence of SEQ ID NO: 11.

In another aspect, an afucosylated anti-FGFR2IIIb antibody comprises a heavy chain variable domain ($V_H$) sequence having at least 90%, 91%, 92%, 93%, 94%, 95%, 96%, 97%, 98%, 99%, or 100% sequence identity to the amino acid sequence of SEQ ID NO: 4. In certain embodiments, a $V_H$ sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-FGFR2IIIb antibody comprising that sequence retains the ability to bind to FGFR2IIIb. In certain embodiments, such anti-FGFR2IIIb antibody retains the ability to selectively bind to FGFR2IIIb without binding to FGFR2IIIc. In certain embodiments, a total of 1 to 10 amino acids have been substituted, inserted and/or deleted in SEQ ID NO: 4. In certain embodiments, substitutions, insertions, or deletions occur in regions outside the HVRs (i.e., in the FRs). Optionally, the afucosylated anti-FGFR2IIIb antibody comprises the $V_H$ sequence in SEQ ID NO: 5, including post-translational modifications of that sequence. In a particular embodiment, the $V_H$ comprises one, two or three HVRs selected from: (a) HVR-H1 comprising the amino acid sequence of SEQ ID NO: 6; (b) HVR-H2 comprising the amino acid sequence of SEQ ID NO: 7; and (c) HVR-H3 comprising the amino acid sequence of SEQ ID NO: 8.

In another aspect, an afucosylated anti-FGFR2IIIb antibody is provided, wherein the antibody comprises a light chain variable domain ($V_L$) having at least 90%, 91%, 92%, 93%, 94%, 95%, 96%, 97%, 98%, 99%, or 100% sequence identity to the amino acid sequence of SEQ ID NO: 5. In certain embodiments, a $V_L$ sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-FGFR2IIIb antibody comprising that sequence retains the ability to bind to FGFR2IIIb. In certain embodiments, such anti-FGFR2IIIb antibody retains the ability to selectively bind to FGFR2IIIb without binding to FGFR2IIIc. In certain embodiments, a total of 1 to 10 amino acids have been substituted, inserted and/or deleted in SEQ ID NO: 5. In certain embodiments, the substitutions, insertions, or deletions occur in regions outside the HVRs (i.e., in the FRs). Optionally, the afucosylated anti-FGFR2IIIb antibody comprises the $V_L$ sequence in SEQ ID NO: 4, including post-translational modifications of that sequence. In a particular embodiment, the $V_L$ comprises one, two or three HVRs selected from (a) HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 11.

In another aspect, an afucosylated anti-FGFR2IIIb antibody comprises a heavy chain variable domain ($V_H$) sequence having at least 90%, 91%, 92%, 93%, 94%, 95%, 96%, 97%, 98%, 99%, or 100% sequence identity to the amino acid sequence of SEQ ID NO: 4 and a light chain variable domain ($V_L$) having at least 90%, 91%, 92%, 93%, 94%, 95%, 96%, 97%, 98%, 99%, or 100% sequence identity to the amino acid sequence of SEQ ID NO: 5. In certain embodiments, a $V_H$ sequence having at least 90%, 91%, 92%, 93%, 94%, 95%, 96%, 97%, 98%, or 99% identity contains substitutions (e.g., conservative substitutions), insertions, or deletions relative to the reference sequence, and a $V_L$ sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-FGFR2IIIb antibody comprising that sequence retains the ability to bind to FGFR2IIIb. In certain embodiments, such anti-FGFR2IIIb antibody retains the ability to selectively bind to FGFR2IIIb without binding to FGFR2IIIc. In certain embodiments, a total of 1 to 10 amino acids have been substituted, inserted and/or deleted in SEQ ID NO: 4. In certain embodiments, a total of 1 to 10 amino acids have been substituted, inserted and/or deleted in SEQ ID NO: 5. In certain embodiments, substitutions, insertions, or deletions occur in regions outside the HVRs (i.e., in the FRs). Optionally, the afucosylated anti-FGFR2IIIb antibody comprises the $V_H$ sequence in SEQ ID NO: 4 and the $V_L$ sequence of SEQ ID NO: 5, including post-translational modifications of one or both sequence. In a particular embodiment, the $V_H$ comprises one, two or three HVRs selected from: (a) HVR-H1 comprising the amino acid sequence of SEQ ID NO: 6; (b) HVR-H2 comprising the amino acid sequence of SEQ ID NO: 7; and (c) HVR-H3 comprising the amino acid sequence of SEQ ID NO: 8; and the $V_L$ comprises one, two or three HVRs selected from (a) HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 11.

In another aspect, an afucosylated anti-FGFR2IIIb antibody is provided, wherein the antibody comprises a $V_H$ as in any of the embodiments provided above, and a $V_L$ as in any of the embodiments provided above. In one embodiment, the antibody comprises the $V_H$ and $V_L$ sequences in SEQ ID NO: 4 and SEQ ID NO: 5, respectively, including post-translational modifications of those sequences.

In another aspect, an afucosylated anti-FGFR2IIIb antibody comprises a heavy chain sequence having at least 90%, 91%, 92%, 93%, 94%, 95%, 96%, 97%, 98%, 99%, or 100% sequence identity to the amino acid sequence of SEQ ID NO: 2. In certain embodiments, a heavy chain sequence having at least 90%, 91%, 92%, 93%, 94%, 95%, 96%, 97%, 98%, or 99% identity contains substitutions (e.g., conservative substitutions), insertions, or deletions relative to the reference sequence, but an afucosylated anti-FGFR2IIIb antibody comprising that sequence retains the ability to bind to FGFR2IIIb. In certain embodiments, such anti-FGFR2IIIb antibody retains the ability to selectively bind to FGFR2IIIb without binding to FGFR2IIIc. In certain embodiments, a total of 1 to 10 amino acids have been substituted, inserted and/or deleted in SEQ ID NO: 2. In certain embodiments, substitutions, insertions, or deletions occur in regions outside the HVRs (i.e., in the FRs). Optionally, the afucosylated anti-FGFR2IIIb antibody heavy chain comprises the $V_H$ sequence in SEQ ID NO: 2, including post-translational modifications of that sequence. In a particular embodiment, the heavy chain comprises one, two or three HVRs selected from: (a) HVR-H1 comprising the amino acid sequence of SEQ ID NO: 6; (b) HVR-H2 comprising the amino acid sequence of SEQ ID NO: 7; and (c) HVR-H3 comprising the amino acid sequence of SEQ ID NO: 8.

In another aspect, an afucosylated anti-FGFR2IIIb antibody is provided, wherein the antibody comprises a light chain having at least 90%, 91%, 92%, 93%, 94%, 95%, 96%, 97%, 98%, 99%, or 100% sequence identity to the amino acid sequence of SEQ ID NO: 3. In certain embodiments, a light chain sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-FGFR2IIIb antibody comprising that sequence retains the ability to bind to FGFR2IIIb. In certain embodiments, such anti-FGFR2IIIb antibody retains the ability to selectively bind to FGFR2IIIb without binding to FGFR2IIIc. In certain embodiments, a total of 1 to 10 amino acids have been substituted, inserted and/or deleted in SEQ ID NO: 3. In certain embodiments, the substitutions, insertions, or deletions occur in regions outside the HVRs (i.e., in the FRs). Optionally, the afucosylated anti-FGFR2IIIb antibody light chain comprises the $V_L$ sequence in SEQ ID NO: 3, including post-translational modifications of that sequence. In a particular embodiment, the light chain comprises one, two or three HVRs selected from (a) HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 11.

In another aspect, an afucosylated anti-FGFR2IIIb antibody comprises a heavy chain sequence having at least 90%, 91%, 92%, 93%, 94%, 95%, 96%, 97%, 98%, 99%, or 100% sequence identity to the amino acid sequence of SEQ ID NO: 2 and a light chain sequence having at least 90%, 91%, 92%, 93%, 94%, 95%, 96%, 97%, 98%, 99%, or 100% sequence identity to the amino acid sequence of SEQ ID NO: 3. In certain embodiments, a heavy chain sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-FGFR2IIIb antibody comprising that sequence retains the ability to bind to FGFR2IIIb. In certain embodiments, such anti-FGFR2IIIb antibody retains the ability to selectively bind to FGFR2IIIb without binding to FGFR2IIIc. In certain embodiments, a light chain sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-FGFR2IIIb antibody comprising that sequence retains the ability to bind to FGFR2IIIb. In certain embodiments, such anti-FGFR2IIIb antibody retains the ability to selectively bind to FGFR2IIIb without binding to FGFR2IIIc. In certain embodiments, a total of 1 to 10 amino acids have been substituted, inserted and/or deleted in SEQ ID NO: 2. In certain embodiments, a total of 1 to 10 amino acids have been substituted, inserted and/or deleted in SEQ ID NO: 3. In certain embodiments, substitutions, insertions, or deletions occur in regions outside the HVRs (i.e., in the FRs). Optionally, the afucosylated anti-FGFR2IIIb antibody heavy chain comprises the $V_H$ sequence in SEQ ID NO: 2, including post-translational modifications of that sequence and the afucosylated anti-FGFR2IIIb antibody light chain comprises the $V_L$ sequence in SEQ ID NO: 3, including post-translational modifications of that sequence. In a particular embodiment, the heavy chain comprises one, two or three HVRs selected from: (a) HVR-H1 comprising the amino acid sequence of SEQ ID NO: 6; (b) HVR-H2 comprising the amino acid sequence of SEQ ID NO: 7; and (c) HVR-H3 comprising the amino acid sequence of SEQ ID NO: 8; and the light chain comprises one, two or three HVRs selected from (a) HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 11.

Exemplary Chimeric Antibodies

In certain embodiments, an antibody, such as an afucosylated antibody, provided herein is a chimeric antibody. Certain chimeric antibodies are described, e.g., in U.S. Pat. No. 4,816,567; and Morrison et al., (1984) *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

Nonlimiting exemplary afucsoylated chimeric antibodies include chimeric antibodies comprising heavy chain HVR1, HVR2, and HVR3, and/or light chain HVR1, HVR2, and HVR3 sequences described herein. In some embodiments, the afucosylated chimeric anti-FGFR2IIIb antibody comprises the variable regions described above and binds to FGFR2IIIb. In some embodiments, the afucosylated chimeric anti-FGFR2IIIb antibody comprises the variable regions described above, binds to FGFR2IIIb and has at least one activity selected from enhanced ADCC activity and enhanced affinity for Fc gamma RIIIA (such as Fc gamma RIIIA(V158) and/or Fc gamma RIIIA(F158)). In some embodiments, the afucosylated chimeric anti-FGFRIIIb antibody does not bind to FGFR2IIIc.

In some embodiments, an afucosylated chimeric anti-FGFR2IIIb antibody comprises a heavy chain comprising a variable region sequence that is at least 90%, at least 91%, at least 92%, at least 93%, at least 94%, at least 95%, at least 96%, at least 97%, at least 98%, or at least 99% identical SEQ ID NO: 4, wherein the antibody binds FGFR2IIIb. In some embodiments, an afucosylated chimeric anti-FGFR2IIIb antibody comprises a light chain comprising a variable region sequence that is at least 90%, at least 91%, at least 92%, at least 93%, at least 94%, at least 95%, at least 96%, at least 97%, at least 98%, or at least 99% identical to SEQ ID NO: 5, wherein the antibody binds FGFR2IIIb. In some embodiments, an afucosylated chimeric anti-FGFR2IIIb antibody comprises a heavy chain comprising a variable region sequence that is at least 90%, at least 91%, at least 92%, at least 93%, at least 94%, at least 95%, at least 96%, at least 97%, at least 98%, or at least 99% identical to SEQ ID NO: 4; and a light chain comprising a variable region sequence that is at least 90%, at least 91%, at least 92%, at least 93%, at least 94%, at least 95%, at least 96%, at least 97%, at least 98%, or at least 99% identical to SEQ ID NO: 5; wherein the antibody binds FGFR2IIIb.

Exemplary afucosylated chimeric anti-FGFR2IIIb antibodies also include chimeric antibodies that compete for binding to FGFR2IIIb with an antibody or fragment thereof described herein. Thus, in some embodiments, a chimeric anti-FGFR2IIIb antibody is provided that competes for binding to FGFR2IIIb with an antibody comprising a heavy chain variable region comprising the amino acid sequence of SEQ ID NO: 4 and a light chain variable region comprising the amino acid sequence of SEQ ID NO: 5. In some embodiments, the antibody competes for binding to FGFR2IIIb, but does not bind FGFR2IIIc.

In some embodiments, a chimeric antibody described herein comprises one or more human constant regions. In some embodiments, the human heavy chain constant region is of an isotype selected from IgA, IgG, and IgD. In some embodiments, the human light chain constant region is of an isotype selected from κ and λ. In some embodiments, a chimeric antibody described herein comprises a human IgG constant region. In some embodiments, a chimeric antibody described herein comprises a human IgG4 heavy chain constant region. In some embodiments, a chimeric antibody described herein comprises a human IgG4 constant region and a human κ light chain.

As noted above, whether or not effector function is desirable may depend on the particular method of treatment intended for an antibody. Thus, in some embodiments, when effector function is desirable, a chimeric anti-FGFR2IIIb antibody comprising a human IgG1 heavy chain constant region or a human IgG3 heavy chain constant region is selected. In some embodiments, when effector function is not desirable, a chimeric anti-FGFR2IIIb antibody comprising a human IgG4 or IgG2 heavy chain constant region is selected.

Exemplary Humanized Antibodies

In some embodiments, afucosylated humanized antibodies that bind FGFR2IIIb are provided. Humanized antibodies are useful as therapeutic molecules because humanized antibodies reduce or eliminate the human immune response to non-human antibodies (such as the human anti-mouse antibody (HAMA) response), which can result in an immune response to an antibody therapeutic, and decreased effectiveness of the therapeutic.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, (2008) *Front. Biosci.* 13: 1619-1633, and are further described, e.g., in Riechmann et al., (1988) *Nature* 332:323-329; Queen et al., (1989) *Proc. Natl Acad. Sci. USA* 86: 10029-10033; U.S. Pat. Nos. 5,821,337, 7,527,791, 6,982,321, and 7,087,409; Kashmiri et al., (2005) *Methods* 36:25-34 (describing SDR (a-CDR) grafting); Padlan, (1991) *Mol. Immunol.* 28:489-498 (describing "resurfacing"); Dall'Acqua et al., (2005) *Methods* 36:43-60 (describing "FR shuffling"); and Osbourn et al., (2005) *Methods* 36:61-68 and Klimka et al., (2000) *Br. J. Cancer,* 83:252-260 (describing the "guided selection" approach to FR shuffling).

Human framework regions that may be used for humanization include but are not limited to: framework regions selected using the "best-fit" method (see, e.g., Sims et al. (1993) *J. Immunol.* 151:2296); framework regions derived from the consensus sequence of human antibodies of a particular subgroup of light or heavy chain variable regions (see, e.g., Carter et al. (1992) *Proc. Natl. Acad. Sci. USA,* 89:4285; and Presta et al. (1993) *J. Immunol,* 151:2623); human mature (somatically mutated) framework regions or human germline framework regions (see, e.g., Almagro and Fransson, (2008) *Front. Biosci.* 13:1619-1633); and framework regions derived from screening FR libraries (see, e.g., Baca et al., (1997) *J. Biol. Chem.* 272: 10678-10684 and Rosok et al., (1996) *J. Biol. Chem.* 271:22611-22618).

Nonlimiting exemplary humanized antibodies include αFGFR2b, described herein. Nonlimiting exemplary afucosylated humanized antibodies include αFGFR2bA, described herein, which has the same amino acid sequences as αFGFR2b comprising fucose (also referred to as αFGFR2bF). Nonlimiting exemplary afucosylated humanized antibodies also include antibodies comprising a heavy chain variable region of αFGFR2b and/or a light chain variable region of αFGFR2b. Nonlimiting exemplary afucosylated humanized antibodies include antibodies comprising a heavy chain variable region of SEQ ID NO: 4 and/or a light chain variable region of SEQ ID NO: 5. Exemplary humanized antibodies also include, but are not limited to, humanized antibodies comprising heavy chain HVR1, HVR2, and HVR3, and/or light chain HVR1, HVR2, and HVR3 of αFGFR2b. In some embodiments, the humanized anti-FGFR2IIIb antibody comprises the HVRs described above (i.e., (a) HVR-H1 comprising the amino acid sequence of SEQ ID NO: 6; (b) HVR-H2 comprising the amino acid sequence of SEQ ID NO: 7; (c) HVR-H3 comprising the amino acid sequence of SEQ ID NO: 8; (d) HVR-L1 comprising the amino acid sequence of SEQ ID NO: 9; (e) HVR-L2 comprising the amino acid sequence of SEQ ID NO: 10; and (f) HVR-L3 comprising the amino acid sequence of SEQ ID NO: 11) and binds to FGFR2IIIb. In some embodiments, the humanized anti-FGFR2IIIb antibody comprises the HVRs described above, binds to FGFR2IIIb and has at least one activity selected from enhanced ADCC activity and enhanced affinity for Fc gamma RIIIA (such as Fc gamma RIIIA(V158) and/or Fc gamma RIIIA(F158)). In some embodiments, the afucosylated humanized anti-FGFRIIIb antibody does not bind to FGFR2IIIc.

In some embodiments, an afucosylated humanized anti-FGFR2IIIb antibody comprises heavy chain HVR1, HVR2, and HVR3 and/or a light chain HVR1, HVR2, and HVR3 of αFGFR2b. Nonlimiting exemplary afucosylated humanized anti-FGFR2IIIb antibodies include antibodies comprising sets of heavy chain HVR1, HVR2, and HVR3 set forth in SEQ ID NOs: 6, 7, and 8. Nonlimiting exemplary afucosylated humanized anti-FGFR2IIIb antibodies also include antibodies comprising sets of light chain HVR1, HVR2, and HVR3 set forth in SEQ ID NOs: 9, 10, and 11.

In some embodiments, an afucosylated humanized anti-FGFR2IIIb antibody comprises a heavy chain comprising a variable region sequence that is at least 90%, at least 91%, at least 92%, at least 93%, at least 94%, at least 95%, at least 96%, at least 97%, at least 98%, or at least 99% identical to SEQ ID NO: 4, and wherein the antibody binds FGFR2IIIb. In some embodiments, an afucosylated humanized anti-FGFR2IIIb antibody comprises a light chain comprising a variable region sequence that is at least 90%, at least 91%, at least 92%, at least 93%, at least 94%, at least 95%, at least 96%, at least 97%, at least 98%, or at least 99% identical to SEQ ID NO: 5, wherein the antibody binds FGFR2IIIb. In some embodiments, an afucosylated humanized anti-FGFR2IIIb antibody comprises a heavy chain comprising a variable region sequence that is at least 90%, at least 91%, at least 92%, at least 93%, at least 94%, at least 95%, at least 96%, at least 97%, at least 98%, or at least 99% identical to SEQ ID NO: 4; and a light chain comprising a variable region sequence that is at least 90%, at least 91%, at least 92%, at least 93%, at least 94%, at least 95%, at least 96%, at least 97%, at least 98%, or at least 99% identical to SEQ ID NO: 5; wherein the antibody binds FGFR2IIIb.

In some embodiments, an afucosylated humanized anti-FGFR2IIIb antibody comprises at least one of the HVRs discussed herein. That is, in some embodiments, an afucosylated humanized anti-FGFR2IIIb antibody comprises at least one HVR selected from a heavy chain HVR1 discussed herein, a heavy chain HVR2 discussed herein, a heavy chain HVR3 discussed herein, a light chain HVR1 discussed herein, a light chain HVR2 discussed herein, and a light chain HVR3 discussed herein. Further, in some embodiments, an afucosylated humanized anti-FGFR2IIIb antibody comprises at least one mutated HVR based on a HVR discussed herein, wherein the mutated HVR comprises 1, 2, 3, or 4 amino acid substitutions relative to the HVR discussed herein. In some embodiments, one or more of the amino acid substitutions are conservative amino acid substitutions. One skilled in the art can select one or more suitable conservative amino acid substitutions for a particular HVR sequence, wherein the suitable conservative amino acid substitutions are not predicted to significantly alter the binding properties of the antibody comprising the mutated HVR.

Exemplary afucosylated humanized anti-FGFR2IIIb antibodies also include antibodies that compete for binding to FGFR2IIIb with an antibody or fragment thereof described herein. Thus, in some embodiments, a humanized anti-FGFR2IIIb antibody is provided that competes for binding to FGFR2IIIb with αFGFR2b. In some embodiments, an afucosylated humanized anti-FGFR2IIIb antibody is provided that competes for binding to FGFR2IIIb with αFGFR2b and has at least one activity selected from enhanced ADCC activity and enhanced affinity for Fc gamma RIIIA (such as Fc gamma RIIIA(V158) and/or Fc gamma RIIIA(F158)). In some embodiments, the afucosylated humanized anti-FGFRIIIb antibody does not bind to FGFR2IIIc.

In some embodiments, an afucosylated humanized anti-FGFR2IIIb antibody comprises one or more human constant regions. In some embodiments, the human heavy chain constant region is of an isotype selected from IgA, IgG, and IgD. In some embodiments, the human light chain constant region is of an isotype selected from κ and λ.

In some embodiments, an afucosylated humanized antibody described herein comprises a human IgG constant region. In some embodiments, when effector function is desirable, an afucosylated humanized anti-FGFR2IIIb antibody comprising a human IgG1 heavy chain constant region or a human IgG3 heavy chain constant region is selected. In some embodiments, an afucosylated humanized antibody described herein comprises a human IgG1 constant region. In some embodiments, an afucosylated humanized antibody described herein comprises a human IgG1 constant region, wherein N297 is not fucosylated. In some embodiments, an afucosylated human antibody described herein comprises a human IgG1 constant region and a human κ light chain.

In some embodiments, an afucosylated humanized antibody comprises a heavy chain comprising the amino acid sequence of SEQ ID NO: 2 and a light chain comprising the amino acid sequence of SEQ ID NO: 3. In some embodiments, an afucosylated humanized antibody comprises a heavy chain consisting of the amino acid sequence of SEQ ID NO: 2, and any post-translational modifications, and a light chain consisting the amino acid sequence of SEQ ID NO: 3, and any post-translational modifications.

Exemplary Antibody Constant Regions

In some embodiments, an afucosylated antibody described herein comprises one or more human constant regions. In some embodiments, the human heavy chain constant region is of an isotype selected from IgA, IgG, and IgD. In some embodiments, the human light chain constant region is of an isotype selected from κ and λ.

In some embodiments, an afucosylated antibody described herein comprises a human IgG constant region. In some embodiments, when effector function is desirable, an afucosylated anti-FGFR2IIIb antibody comprising a human IgG1 heavy chain constant region or a human IgG3 heavy chain constant region is selected. In some embodiments, an afucosylated antibody described herein comprises a human IgG1 constant region. In some embodiments, an afucosylated antibody described herein comprises a human IgG1 constant region, wherein N297 is not fucosylated. In some embodiments, an afucosylated antibody described herein comprises a human IgG1 constant region and a human κ light chain.

Throughout the present specification and claims unless explicitly stated or known to one skilled in the art, the numbering of the residues in an immunoglobulin heavy chain is that of the EU index as in Kabat et al., *Sequences of Proteins of Immunological Interest,* 5th Ed. Public Health Service, National Institutes of Health, Bethesda, Md. (1991), expressly incorporated herein by reference. The "EU index as in Kabat" refers to the residue numbering of the human IgG1 EU antibody.

In certain embodiments, an antibody of the invention comprises a variant Fc region has at least one amino acid substitution compared to the Fc region of a wild-type IgG or a wild-type antibody. In certain embodiments, the variant Fc region has two or more amino acid substitutions in the Fc region of the wild-type antibody. In certain embodiments, the variant Fc region has three or more amino acid substitutions in the Fc region of the wild-type antibody. In certain embodiments, the variant Fc region has at least one, two or three or more Fc region amino acid substitutions described herein. In certain embodiments, the variant Fc region herein will possess at least about 80% homology with a native sequence Fc region and/or with an Fc region of a parent antibody. In certain embodiments, the variant Fc region herein will possess at least about 90% homology with a native sequence Fc region and/or with an Fc region of a parent antibody. In certain embodiments, the variant Fc region herein will possess at least about 95% homology with a native sequence Fc region and/or with an Fc region of a parent antibody.

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibodies with certain improved properties.

In one embodiment, antibodies are provided having a carbohydrate structure that lacks fucose attached (directly or indirectly) to an Fc region (i.e., afucosylated antibodies). For example, the amount of fucose in a composition comprising a plurality of such antibodies may be from 0% to about 5%. In some embodiments, a composition comprising a plurality of such antibodies comprises at least 95% afucosylated antibodies. The amount of fucose is determined by calculating the average amount of fucose within the sugar chain at Asn297, relative to the sum of all glycostructures attached to Asn 297 (e.g., complex, hybrid and high mannose structures). Nonlimiting exemplary methods of detecting fucose in an antibody include MALDI-TOF mass spectrometry (see, e.g., WO 2008/077546), HPLC measurement of released fluorescently labeled oligosaccharides (see, e.g., Schneider et al., "N-Glycan analysis of monoclonal antibodies and other glycoproteins using UHPLC with fluorescence detection," Agilent Technologies, Inc. (2012); Lines, *J. Pharm. Biomed. Analysis,* 14: 601-608 (1996); Takahasi, *J. Chrom.,* 720: 217-225 (1996)), capillary electrophoresis measurement of released fluorescently labeled oligosaccharides (see, e.g., Ma et al., *Anal. Chem.,* 71: 5185-5192 (1999)), and HPLC with pulsed amperometric detection to measure monosaccharide composition (see, e.g., Hardy, et al., *Analytical Biochem.,* 170: 54-62 (1988)). Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. In antibody αFGFR2b described herein, Asn297 is found in the sequence QY<u>N</u>ST, and is in bold and underlined in the Table of Sequences shown below, SEQ ID NO: 2. Fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "afucosylated" or "fucose-deficient" antibodies include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing afucosylated antibodies include Lec13 CHO cells deficient in protein fucosylation (Ripka et al. *Arch. Biochem. Biophys.* 249:533-545 (1986); US Patent Application No. US 2003/0157108 A1, Presta, L; and WO 2004/056312 A1, Adams et al., especially at Example 11), and knockout cell lines, such as cell lines lacking a functional alpha-1,6-fucosyltransferase gene, FUT8, e.g., knockout CHO cells (see, e.g., Yamane-Ohnuki et al. *Biotech. Bioeng.* 87: 614 (2004); Kanda, Y. et al., *Biotechnol. Bioeng.,* 94(4):680-688 (2006); and WO2003/085107).

Antibodies are further provided with bisected oligosaccharides, e.g., in which a biantennary oligosaccharide attached to the Fc region of the antibody is bisected by GlcNAc. Such antibodies may have reduced fucosylation and/or improved ADCC function. Examples of such antibodies are described, e.g., in WO 2003/011878 (Jean-Mairet et al.); U.S. Pat. No. 6,602,684 (Umana et al.); and US 2005/0123546 (Umana et al.). Antibodies with at least one galactose residue in the oligosaccharide attached to the Fc region are also provided. Such antibodies may have improved CDC function. Such antibodies are described, e.g., in WO 1997/30087 (Patel et al.); WO 1998/58964 (Raju, S.); and WO 1999/22764 (Raju, S.).

Antibodies are also provided with amino-terminal leader extensions. For example, one or more amino acid residues of the amino-terminal leader sequence are present at the amino-terminus of any one or more heavy or light chains of an antibody. An exemplary amino-terminal leader extension comprises or consists of three amino acid residues, VHS, present on one or both light chains of an antibody.

The in vivo or serum half-life of human FcRn high affinity binding polypeptides can be assayed, e.g., in transgenic mice, in humans, or in non-human primates to which the polypeptides with a variant Fc region are administered. See also, e.g., Petkova et al. *International Immunology* 18(12): 1759-1769 (2006).

In some embodiments of the invention, an afucosylated antibody mediates ADCC in the presence of human effector cells more effectively than a parent antibody that comprises fucose, Generally, ADCC activity may be determined using the in vitro ADCC assay as herein disclosed, but other assays or methods for determining ADCC activity, e.g. in an animal model etc., are contemplated.

In certain embodiments, the "$K_D$," "$K_d$," "Kd" or "Kd value" of the antibody is measured by using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NETS) according to the supplier's instructions. Antigen is diluted with 10 mM sodium acetate, pH 4.8, to 5 μg/ml (~0.2 μM) before injection at a flow rate of 5 μL/minute to achieve approximately 10 response units (RU) of coupled protein. Following the injection of antigen, 1 M ethanolamine is injected to block unreacted groups. For kinetics measurements, serial dilutions of polypeptide, e.g., full length antibody, are injected in PBS with 0.05% TWEEN-20' surfactant (PBST) at 25° C. at a flow rate of approximately 25 μL/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

An "on-rate," "rate of association," "association rate," or "$k_{on}$" of the antibody can also be determined as described above using a BIACORE®-2000 or a BIACORE®-3000 system (BIAcore, Inc., Piscataway, N.J.).

In certain embodiments, the difference between said two values (e.g., Kd values) is substantially the same, for example, less than about 50%, less than about 40%, less than about 30%, less than about 20%, and/or less than about 10% as a function of the reference/comparator value.

In certain embodiments, the difference between said two values (e.g., $K_d$ values) is substantially different, for example, greater than about 10%, greater than about 20%, greater than about 30%, greater than about 40%, and/or greater than about 50% as a function of the value for the reference/comparator molecule.

Exemplary Leader Sequences

In order for some secreted proteins to express and secrete in large quantities, a leader sequence from a heterologous protein may be desirable. In some embodiments, employing heterologous leader sequences may be advantageous in that a resulting mature polypeptide may remain unaltered as the leader sequence is removed in the ER during the secretion process. The addition of a heterologous leader sequence may be required to express and secrete some proteins.

Certain exemplary leader sequence sequences are described, e.g., in the online Leader sequence Database maintained by the Department of Biochemistry, National University of Singapore. See Choo et al., *BMC* Bioinformatics, 6: 249 (2005); and PCT Publication No. WO 2006/081430.

III. Properties of Afucosylated Anti-FGFR2IIIb Antibodies

In some embodiments, afucosylated anti-FGFR2IIIb antibodies have enhanced ADCC activity in vitro and/or in vivo. In some embodiments, afucosylated anti-FGFR2IIIb antibodies have enhanced ADCC activity in vitro. In some embodiments, ADCC activity in vitro is determined by a method described herein, e.g., in Example 3. Briefly, FGFR2IIIb-expressing cells are contacted with freshly isolated human PBMCs at a ratio of 25:1 effector (PBMCs) to target cells, in the presence of fucosylated antibody or afucosylated antibody. In some embodiments, Ba/F3 cells that express FGFR2IIIb are used as target cells. In some embodiments, cytotoxicity is determined by quantifying LDH release using CytoTox Non-Radioactive Cytotoxicity Assay (Promega, Madison, Wis.). In some embodiments, maximal lysis is determined using 5% Triton X-100 and spontaneous release is determined in the absence of antibody. In some embodiments, the percentage of specific lysis may be determined using the formula: (experimental−spontaneous release)/(maximal−spontaneous release)×100=% specific lysis. In some embodiments, an afucosylated anti-FGFR2IIIb antibody having enhanced ADCC activity results in specific lysis that is at least 10, at least 15, at least 20, at least 25, at least 30, at least 35, at least 40, at least 45, at least 50, at least 60, at least 65, at least 70, or at least 75 percentage points greater than specific lysis with the same amount of a fucosylated antibody, at at least one concentration of antibody tested. In some embodiments, an afucosylated anti-FGFR2IIIb antibody having enhanced ADCC activity results in specific lysis that is at least 10, at least 15, at least 20, at least 25, at least 30, at least 35, at least 40, at least 45, at least 50, at least 60, at least 65, at least 70, or at least 75 percentage points greater than specific lysis with a fucosylated antibody, where each antibody is at a concentration of between 0.01 and 1 µg/ml and the target cells are Ba/F3 cells expressing FGFR2IIIb. In some embodiments, the antibodies are tested at a concentration of 0.01 µg/ml, 0.1 µg/ml, or 1 µg/ml.

In some embodiments, afucosylated anti-FGFR2IIIb antibodies have enhanced affinity for Fc gamma RIIIA In some embodiments, afucosylated anti-FGFR2IIIb antibodies have enhanced affinity for Fc gamma RIIIA(V158). In some embodiments, afucosylated anti-FGFR2IIIb antibodies have enhanced affinity for Fc gamma RIIIA(F158). In some embodiments, antibody affinity for Fc gamma RIIIA is determined using surface plasmon resonance, e.g., as described herein in Example 2, and/or as follows, which is described with reference to Fc gamma RIIIA(V158), but which is also suitable for determining affinity for Fc gamma RIIIA(F158). Briefly, in some embodiments, fucosylated or afucosylated anti-FGFR2IIIb antibody is captured on a protein A-coated dextran chip. Fc gamma RIIIA (V158) (available from, e.g., R&D Systems) is injected at various concentrations. The association constant, dissociation constant, and affinity of Fc gamma RIIIA (V158) for fucosylated and afucosylated anti-FGFR2IIIb antibody may be determined, e.g., using software provided with the surface plasmon resonance system (for example, Biacore T200 Evaluation Software 1:1 binding model). In some embodiments, an afucosylated anti-FGFR2IIIb antibody with enhanced affinity for Fc gamma RIIIA (such as Fc gamma RIIIA (V158) or Fc gamma RIIIA(F158)) binds to Fc gamma RIIIA with at least 2-fold, at least 3-fold, at least 4-fold, at least 5-fold, at least 7-fold, at least 10-fold, at least 12-fold, at least 15-fold, at least 17-fold, or at least 20-fold greater affinity than a fucosylated anti-FGFR2IIIb antibody. For example, if an afucosylated anti-FGFR2IIIb antibody binds to Fc gamma RIIIA (V158) with an affinity ($K_D$) of 9.2 nM and a fucosylated anti-FGFR2IIIb antibody binds to Fc gamma RIIIA (V158) with an affinity ($K_D$) of 207 nM, then the afucosylated anti-FGFR2IIIb antibody binds to Fc gamma RIIIA (V158) with 207/9.2=22.5-fold greater affinity than the fucosylated anti-FGFR2IIIb antibody.

IV. Anti-FGFR2IIIb Antibody Expression and Production Nucleic Acid Molecules Encoding Anti-FGFR2IIIb Antibodies Nucleic acid molecules comprising polynucleotides that encode one or more chains of anti-FGFR2IIIb antibodies are provided. In some embodiments, a nucleic acid molecule comprises a polynucleotide that encodes a heavy chain or a light chain of an anti-FGFR2IIIb antibody. In some embodiments, a nucleic acid molecule comprises both a polynucleotide that encodes a heavy chain and a polynucleotide that encodes a light chain, of an anti-FGFR2IIIb antibody. In some embodiments, a first nucleic acid molecule comprises a first polynucleotide that encodes a heavy chain and a second nucleic acid molecule comprises a second polynucleotide that encodes a light chain.

In some such embodiments, the heavy chain and the light chain are expressed from one nucleic acid molecule, or from two separate nucleic acid molecules, as two separate polypeptides. In some embodiments, such as when an antibody is an scFv, a single polynucleotide encodes a single polypeptide comprising both a heavy chain and a light chain linked together.

In some embodiments, a polynucleotide encoding a heavy chain or light chain of an anti-FGFR2IIIb antibody comprises a nucleotide sequence that encodes a leader sequence, which, when translated, is located at the N terminus of the heavy chain or light chain. As discussed above, the leader sequence may be the native heavy or light chain leader sequence, or may be another heterologous leader sequence.

Nucleic acid molecules may be constructed using recombinant DNA techniques conventional in the art. In some embodiments, a nucleic acid molecule is an expression vector that is suitable for expression in a selected host cell.

Vectors

Vectors comprising polynucleotides that encode anti-FGFR2IIIb heavy chains and/or anti-FGFR2IIIb light chains are provided. Vectors comprising polynucleotides that encode anti-FGFR2IIIb heavy chains and/or anti-FGFR2IIIb light chains are also provided. Such vectors include, but are not limited to, DNA vectors, phage vectors, viral vectors, retroviral vectors, etc. In some embodiments, a vector comprises a first polynucleotide sequence encoding a heavy chain and a second polynucleotide sequence encoding a light chain. In some embodiments, the heavy chain and light chain are expressed from the vector as two separate polypeptides. In some embodiments, the heavy chain and light chain are expressed as part of a single polypeptide, such as, for example, when the antibody is an scFv.

In some embodiments, a first vector comprises a polynucleotide that encodes a heavy chain and a second vector comprises a polynucleotide that encodes a light chain. In some embodiments, the first vector and second vector are transfected into host cells in similar amounts (such as similar molar amounts or similar mass amounts). In some embodiments, a mole- or mass-ratio of between 5:1 and 1:5 of the first vector and the second vector is transfected into host cells. In some embodiments, a mass ratio of between 1:1 and 1:5 for the vector encoding the heavy chain and the vector encoding the light chain is used. In some embodiments, a mass ratio of 1:2 for the vector encoding the heavy chain and the vector encoding the light chain is used.

In some embodiments, a vector is selected that is optimized for expression of polypeptides in CHO or CHO-derived cells, or in NS0 cells. Exemplary such vectors are described, e.g., in Running Deer et al., Biotechnol. Prog. 20:880-889 (2004).

Host Cells

In various embodiments, anti-FGFR2IIIb heavy chains and/or anti-FGFR2IIIb light chains may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO-S, DG44. Lec13 CHO cells, and FUT8 CHO cells; PER.C6® cells (Crucell); and NS0 cells. In some embodiments, anti-FGFR2IIIb heavy chains and/or anti-FGFR2IIIb light chains may be expressed in yeast. See, e.g., U.S. Publication No. US 2006/0270045 A1. In some embodiments, a particular eukaryotic host cell is selected based on its ability to make desired post-translational modifications to the anti-FGFR2IIIb heavy chains and/or anti-FGFR2IIIb light chains. For example, in some embodiments, CHO cells produce polypeptides that have a higher level of sialylation than the same polypeptide produced in 293 cells.

Introduction of one or more nucleic acids into a desired host cell may be accomplished by any method, including but not limited to, calcium phosphate transfection, DEAE-dextran mediated transfection, cationic lipid-mediated transfection, electroporation, transduction, infection, etc. Nonlimiting exemplary methods are described, e.g., in Sambrook et al., Molecular Cloning, A Laboratory Manual, 3$^{rd}$ ed. Cold Spring Harbor Laboratory Press (2001). Nucleic acids may be transiently or stably transfected in the desired host cells, according to any suitable method.

In some embodiments afucosylated anti-FGFR2IIIb antibodies are produced in cells capable of producing afucosylated antibodies, such as Lec13 CHO cells deficient in protein fucosylation (Ripka et al. Arch. Biochem. Biophys. 249:533-545 (1986); US Patent Application No. US 2003/0157108 A1, Presta, L; and WO 2004/056312 A1, Adams et al., especially at Example 11), and knockout cell lines, such as cell lines lacking a functional alpha-1,6-fucosyltransferase gene, FUT8, e.g., knockout CHO cells (see, e.g., Yamane-Ohnuki et al. Biotech. Bioeng. 87: 614 (2004); Kanda, Y. et al., Biotechnol. Bioeng., 94(4):680-688 (2006); and WO2003/085107). In some embodiments, afucosylated anti-FGFR2IIIb antibodies are produced in CHO cells lacking a functional FUT8 gene. In some embodiments, afucosylated anti-FGFR2IIIb antibodies are produced in Potelligent® CHOK1SV cells (BioWa/Lonza, Allendale, N.J.).

Purification of Anti-FGFR2IIIb Antibodies

Anti-FGFR2IIIb antibodies may be purified by any suitable method. Such methods include, but are not limited to, the use of affinity matrices or hydrophobic interaction chromatography. Suitable affinity ligands include the FGFR2IIIb ECD and ligands that bind antibody constant regions. For example, a Protein A, Protein G, Protein A/G, or an antibody affinity column may be used to bind the constant region and to purify an anti-FGFR2IIIb antibody. Hydrophobic interactive chromatography, for example, a butyl or phenyl column, may also suitable for purifying some polypeptides. Many methods of purifying polypeptides are known in the art.

Cell-Free Production of Anti-FGFR2IIIb Antibodies

In some embodiments, an anti-FGFR2IIIb antibody is produced in a cell-free system. Nonlimiting exemplary cell-free systems are described, e.g., in Sitaraman et al., Methods Mol. Biol. 498: 229-44 (2009); Spirin, Trends Biotechnol. 22: 538-45 (2004); Endo et al., Biotechnol. Adv. 21: 695-713 (2003).

V. Therapeutic Compositions and Methods

Methods of Treating Diseases Using Anti-FGFR2IIIb Antibodies

Antibodies of the invention, and compositions comprising antibodies of the invention, are provided for use in methods of treatment for humans or animals. Methods of treating disease comprising administering afucosylated anti-FGFR2IIIb antibodies are also provided. Nonlimiting exemplary diseases that can be treated with afucosylated anti-FGFR2IIIb antibodies include, but are not limited to cancer. In some embodiments, methods of treating cancer are provided, comprising administering an afucosylated anti-FGFR2IIIb antibody. In some embodiments, the cancer is selected from gastric cancer, breast cancer, ovarian cancer, endometrial cancer, pancreatic cancer, or esophageal cancer. In some embodiments, methods of treating gastric cancer are provided, comprising administering an afucosylated anti-FGFR2IIIb antibody.

In some embodiments, a cancer comprises an FGFR2 gene amplification. In some embodiments, a cancer comprising an FGFR2 gene amplification overexpresses FGFR2IIIb. In some embodiments, a cancer comprising FGFR2 amplification overexpresses FGFR2IIIb to a greater extent than FGFR2IIIc. In some embodiments, a cancer comprising FGFR2 amplification expresses FGFR2IIIb at a normalized level that is more than 2-fold, 3-fold, 5-fold, or 10-fold greater than the normalized level of FGFR2IIIc expression. In some embodiments, the expression levels are normalized to GUSB. In some embodiments, a cancer overexpresses FGFR2IIIb but does not comprise FGFR2 gene amplification. In some embodiments, a gastric cancer comprises an FGFR2 gene amplification. In some embodiments, a gastric cancer comprising an FGFR2 gene amplification overexpresses FGFR2IIIb. In some embodiments, a gastric cancer comprising FGFR2 amplification overexpresses FGFR2IIIb to a greater extent than FGFR2IIIc. In some embodiments, a gastric cancer comprising FGFR2 amplification expresses FGFR2IIIb at a normalized level that is more than 2-fold, 3-fold, 5-fold, or 10-fold greater than the normalized level of FGFR2IIIc expression. In some embodiments, the expression levels are normalized to GUSB. In some embodiments, a gastric cancer overexpresses FGFR2IIIb but does not comprise FGFR2 gene amplification. In some embodiments, overexpression is mRNA overexpression. In some embodiments, overexpression is protein overexpression.

FGFR2IIIb gene amplification may be determined by any suitable method in the art, including but not limited to, in situ hybridization (ISH). In some embodiments, FGFR2 amplification comprises FGFR2:CEN10 (chromosome 10 centromere) ratio of >3.

FGFR2IIIb mRNA overexpression may be determined by any suitable method in the art, including but not limited to, methods comprising quantitative PCR (qPCR). The term "FGFR2IIIb mRNA overexpression" means elevated levels of FGFR2IIIb mRNA, regardless of the cause of such elevated levels (i.e., whether the elevated levels are a result of increased transcription and/or decreased degradation of mRNA, other mechanism, or a combination of mechanisms).

FGFR2IIIb protein overexpression may be determined by any suitable method in the art, including but not limited to, antibody-based methods such as immunohistochemistry (IHC). In some embodiments, the IHC staining is scored according to methods in the art. The term "FGFR2IIIb protein overexpression" means elevated levels of FGFR2IIIb protein, regardless of the cause of such elevated levels (i.e., whether the elevated levels are a result of increased translation and/or decreased degradation of protein, other mechanism, or a combination of mechanisms). In some embodiments, 1+, 2+, or 3+ staining of tumor cells by IHC indicates FGFR2IIIb overexpression. In some embodiments, 2+ or 3+ staining of tumor cells by IHC indicates FGFR2IIIb overexpression. In some embodiments, the IHC staining is scored as described in Example 6.

Pharmaceutical Compositions

In various embodiments, compositions comprising afucosylated anti-FGFR2IIIb antibodies are provided in formulations with a wide variety of pharmaceutically acceptable carriers (see, e.g., Gennaro, Remington: The Science and Practice of Pharmacy with Facts and Comparisons: Drugfacts Plus, 20th ed. (2003); Ansel et al., Pharmaceutical Dosage Forms and Drug Delivery Systems, 7$^{th}$ ed., Lippencott Williams and Wilkins (2004); Kibbe et al., Handbook of Pharmaceutical Excipients, 3$^{rd}$ ed., Pharmaceutical Press (2000)). Various pharmaceutically acceptable carriers, which include vehicles, adjuvants, and diluents, are available. Moreover, various pharmaceutically acceptable auxiliary substances, such as pH adjusting and buffering agents, tonicity adjusting agents, stabilizers, wetting agents and the like, are also available. Non-limiting exemplary carriers include saline, buffered saline, dextrose, water, glycerol, ethanol, and combinations thereof.

In various embodiments, compositions comprising afucosylated anti-FGFR2IIIb antibodies may be formulated for injection, including subcutaneous administration, by dissolving, suspending, or emulsifying them in an aqueous or nonaqueous solvent, such as vegetable or other oils, synthetic aliphatic acid glycerides, esters of higher aliphatic acids, or propylene glycol; and if desired, with conventional additives such as solubilizers, isotonic agents, suspending agents, emulsifying agents, stabilizers and preservatives. In various embodiments, the compositions may be formulated for inhalation, for example, using pressurized acceptable propellants such as dichlorodifluoromethane, propane, nitrogen, and the like. The compositions may also be formulated, in various embodiments, into sustained release microcapsules, such as with biodegradable or non-biodegradable polymers. A non-limiting exemplary biodegradable formulation includes poly lactic acid-glycolic acid polymer. A non-limiting exemplary non-biodegradable formulation includes a polyglycerin fatty acid ester. Certain methods of making such formulations are described, for example, in EP 1 125 584 A1.

Routes of Administration

In various embodiments, afucosylated anti-FGFR2IIIb antibodies may be administered in vivo by various routes, including, but not limited to, oral, intra-arterial, parenteral, intranasal, intramuscular, intracardiac, intraventricular, intratracheal, buccal, rectal, intraperitoneal, intradermal, topical, transdermal, and intrathecal, or otherwise by implantation or inhalation. The subject compositions may be formulated into preparations in solid, semi-solid, liquid, or gaseous forms; including, but not limited to, tablets, capsules, powders, granules, ointments, solutions, suppositories, enemas, injections, inhalants, and aerosols. The appropriate formulation and route of administration may be selected according to the intended application.

Pharmaceutical compositions are administered in an amount effective for treatment or prophylaxis of cancer, such as gastric cancer, breast cancer, ovarian cancer, endometrial cancer, pancreatic cancer, or esophageal cancer. The therapeutically effective amount is typically dependent on the weight of the subject being treated, his or her physical or health condition, the extensiveness of the condition to be treated, or the age of the subject being treated. In general, afucosylated anti-FGFR2IIIb antibodies may be administered in an amount in the range of about 10 µg/kg body weight to about 100 mg/kg body weight per dose. In some embodiments, afucosylated anti-FGFR2IIIb antibodies may be administered in an amount in the range of about 50 µg/kg body weight to about 5 mg/kg body weight per dose. In some embodiments, anti-FGFR2IIIb antibodies may be administered in an amount in the range of about 100 µg/kg body weight to about 10 mg/kg body weight per dose. In some embodiments, afucosylated anti-FGFR2IIIb antibodies may be administered in an amount in the range of about 100 µg/kg body weight to about 20 mg/kg body weight per dose. In some embodiments, afucosylated anti-FGFR2IIIb antibodies may be administered in an amount in the range of about 0.5 mg/kg body weight to about 20 mg/kg body weight per dose.

The afucosylated anti-FGFR2IIIb antibody compositions may be administered as needed to subjects. Determination of the frequency of administration may be made by persons skilled in the art, such as an attending physician based on considerations of the condition being treated, age of the subject being treated, severity of the condition being treated, general state of health of the subject being treated and the like. In some embodiments, an effective dose of an afucosylated anti-FGFR2IIIb antibody is administered to a subject one or more times. In various embodiments, an effective dose of an afucosylated anti-FGFR2IIIb antibody is administered to the subject once a month, more than once a month, such as, for example, every two months or every three months. In other embodiments, an effective dose of an afucosylated anti-FGFR2IIIb antibody is administered less than once a month, such as, for example, every two weeks or every week. An effective dose of an afucosylated anti-FGFR2IIIb antibody is administered to the subject at least once. In some embodiments, the effective dose of an afucosylated anti-FGFR2IIIb antibody may be administered multiple times, including for periods of at least a month, at least six months, or at least a year.

Combination Therapy

Afucosylated anti-FGFR2IIIb antibodies may be administered alone or with other modes of treatment. They may be provided before, substantially contemporaneous with, or after other modes of treatment, for example, surgery, chemotherapy, or radiation therapy. In some embodiments, an afucosylated anti-FGFR2IIIb antibody is administered in conjunction with another anti-cancer agent. Nonlimiting exemplary anti-cancer agents that may be administered with an afucosylated anti-FGFR2IIIb antibody include platinum agents (such as cisplatin, oxaliplatin, and carboplatin), paclitaxel (TAXOL®), albumin-engineered nanoparticle formulation of paclitaxel (ABRAXANE®), docetaxel (TAXOTERE®), gemcitabine (GEMZAR®), capecitabine (XELODA®), irinotecan (CAMPTOSAR®), epirubicin (ELLENCE®, PHARMORUBICIN®), FOLFOX (oxaliplatin combined with 5-FU and leucovorin), FOLFIRI (combination of leucovorin, 5-FU and irinotecan), leucovorin, fluorouracil (5-FU, EFUDEX®), mitomycin C (MITOZYTREX™, MUTAMYCIN®), and doxorubicin hydrochloride (Adriamycin PFS, Adriamycin RDF, RUBEX®). In some embodiments, an afucosylated anti-FGFR2IIIb antibody is administered in conjunction with paclitaxel. In some embodiments, an afucosylated anti-FGFR2IIIb antibody is administered in conjunction with cisplatin and/or 5-FU. In some embodiments, an afucosylated anti-FGFR2IIIb antibody is administered in conjunction with cisplatin and 5-FU. In some embodiments, an afucosylated anti-FGFR2IIIb antibody is administered in conjunction with FOLFOX (oxaliplatin, 5-FU, and leucovorin).

Kits/Articles of Manufacture

The invention also provides kits, medicines, compositions, and unit dosage forms for use in any of the methods described herein.

Kits of the invention include one or more containers comprising an afucosylated anti-FGFR2IIIb antibody (or unit dosage forms and/or articles of manufacture). In some embodiments, a unit dosage is provided wherein the unit dosage contains a predetermined amount of a composition comprising an afucosylated anti-FGFR2IIIb antibody, with or without one or more additional agents. In some embodiments, such a unit dosage is supplied in single-use prefilled syringe for injection. In various embodiments, the composition contained in the unit dosage may comprise saline, sucrose, or the like; a buffer, such as phosphate, or the like; and/or be formulated within a stable and effective pH range. Alternatively, in some embodiments, the composition may be provided as a lyophilized powder that may be reconstituted upon addition of an appropriate liquid, for example, sterile water. In some embodiments, the composition comprises one or more substances that inhibit protein aggregation, including, but not limited to, sucrose and arginine. In some embodiments, a composition of the invention comprises heparin and/or a proteoglycan.

In some embodiments, kits of the invention further comprise instructions for use in the treatment of, e.g., cancer (such as gastric cancer, breast cancer, ovarian cancer, endometrial cancer, pancreatic cancer, or esophageal cancer) in accordance with any of the methods described herein. The kit may further comprise a description of selection an individual suitable or treatment. Instructions supplied in the kits of the invention are typically written instructions on a label or package insert (e.g., a paper sheet included in the kit), but machine-readable instructions (e.g., instructions carried on a magnetic or optical storage disk) are also acceptable. In some embodiments, the kit further comprises another therapeutic agent.

The kits of the invention are in suitable packaging. Suitable packaging include, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

EXAMPLES

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1: Production of Afucosylated Anti-FGFR2IIIb Antibody

Construction of Expression Vector.

Nucleotide sequences encoding the heavy chain (HC) and light chain (LC) of monoclonal antibody αFGFR2b were cloned into the GS Gene Expression System (Lonza, Basel, Switzerland) according to the manufacturer's instructions. The system generates a double gene vector (DGV) containing the expression cassettes for both the light chain and the heavy chain.

Choice of Host Cell Line.

To generate afucosylated monoclonal antibody αFGFR2bA (the designation "A" after αFGFR2b refers to "afucosylated"), the Potelligent® CHOK1SV cells (BioWa/Lonza, Allendale, N.J.) was chosen as host cell line. Potelligent® CHOK1SV cells lack the FUT8 gene (α1,6-fucosyltransferase) and therefore produce fucose-free antibodies (afucosylated antibodies).

Construction of Stable Cell Line for Production of Afucosylated αFGFR2bA Antibody:

The expression vector comprising the nucleotide sequences encoding αFGFR2b antibody heavy chain and light chain described above transfected into Potelligent® CHOK1SV cells by electroporation according to the manufacturer's instructions. Electroporated cells were seeded into a 96-well plate at about 10,000 cells/50 μl/well in CD CHO medium without L-glutamine. Selective CD CHO medium containing 67 μM L-methionine sulfoximine (MSX, SIGMA cat #M5379, St. Louis, Mo.) was added the next day at 150 μl/well. Cell growth and clone formation was monitored with an IN Cell Analyzer 2000 (GE Healthcare, Piscataway, N.J.).

After 4-6 weeks, the surviving colonies were screened for expression of αFGFR2bA antibody using a Homogenous Time Resolved Fluorescence (HTRF) based assay against standard curves generated with purified αFGFR2b antibody, using XL665 conjugated protein A and cryptate conjugated polyclonal rabbit IgG (Cisbio, Bedford, Mass.). The highest expressing clones were expanded through a series of increasing-scale production processes, including 24-well plates, spin tubes, shake flasks, bench scale bioreactors, and finally a platform production process. At each step, only a subset comprising the highest-expressing clones were taken on to the next process. The final production clone was selected based on the evaluation of protein product titers, cell growth characteristics, product quality, stability, as well as scalability in bioreactors. The final production line had an expression level of about 3.5 g/L for αFGFR2bA. Lack of fucosylation in αFGFR2bA produced in the final production cell line was confirmed using normal phase HLPC (N-HPLC) chromatography.

αFGFR2bA antibody was purified by column chromatography and ultrafiltration to concentrate the purified material, then diafiltration to exchange into formulation buffer (20 mM histidine, 150 mM L-arginine, 0.01% polysorbate 20, pH 6.0). Antibody was stored below −70° C.

Figure 7A:
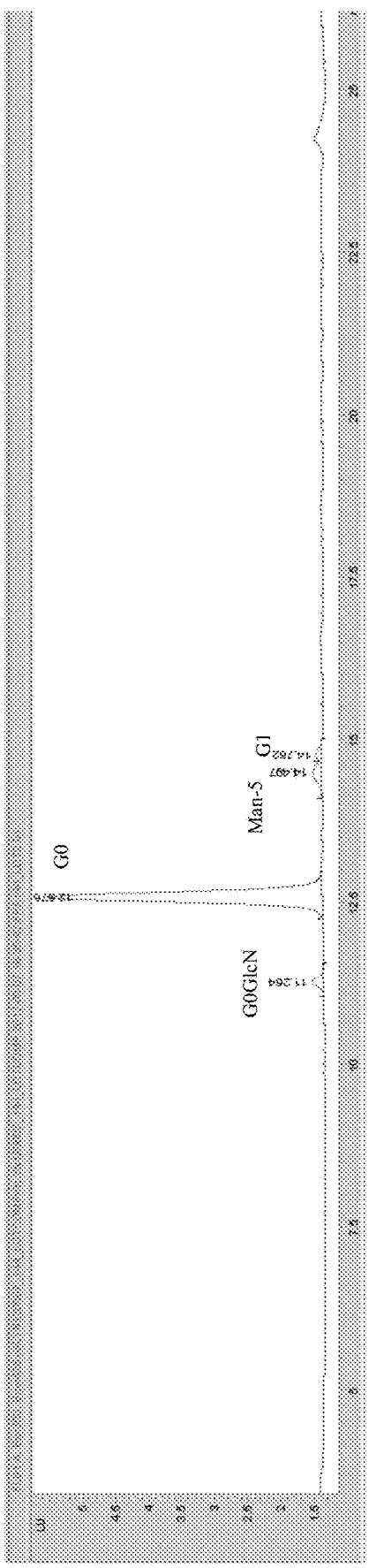
FIGS. 7A and 7B show the glycan profile of αFGFR2b antibody produced in (7A) Potelligent® CHOK1SV cells and (7B) CHOK1SV cells, as described in Example 1.
Figure 7B:
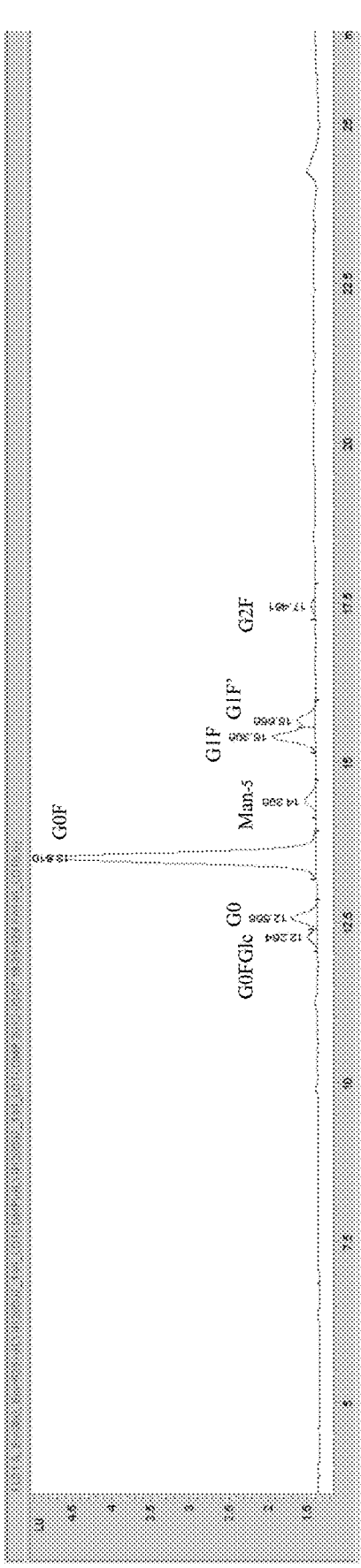

Glycan analysis of αFGFR2bA is performed by releasing the glycans from the protein, labeling the glycans with anthranilic acid (2-AA), and then purifying the labeled glycans. Normal phase HPLC with fluorescent detection is used to separate the glycans and measure the relative amount of each glycan in the antibody. FIG. 7 shows that αFGFR2b derived from the Potelligent® CHOK1SV cell line and αFGFR2b produced from CHOK1SV had two different glycan distributions. (A) Glycan distribution of αFGFR2b derived from the Potelligent® CHOK1SV cell line shows that the antibody lacks fucose ("G0"). (B) Glycan distribution of αFGFR2b derived from the CHOK1SV cell line shows that the antibody contains fucose ("G0F").

Glycan peaks from the normal phase HPLC separation were identified using two orthogonal methods. First, the Potelligent® CHOK1SV produced αFGFR2b were labeled and separated using the normal phase HPLC method. After the fluorescent detection, the glycans were passed through a QTrap mass spectrometer. The mass of each peak was determined and used to positively identify each glycan, and is shown in Table 2.

TABLE 2

| | Mass of glycan peaks | |
|---|---|---|
| Glycan | Theoretical Mass (Da) | Observed Mass (Da) |
| G0 | 1437 | 1437.4 |
| Man-5 | 1355 | 1355.3 |
| G1 | 1600 | 1599.4 |

Figure 8:
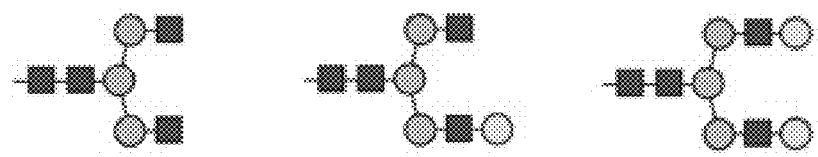
FIG. 8 shows schematic diagrams of N-linked glycans typically found in antibodies.
Figure 8:
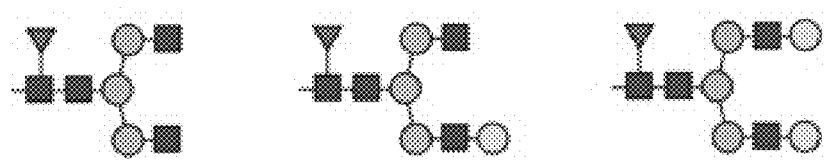
Figure 8:
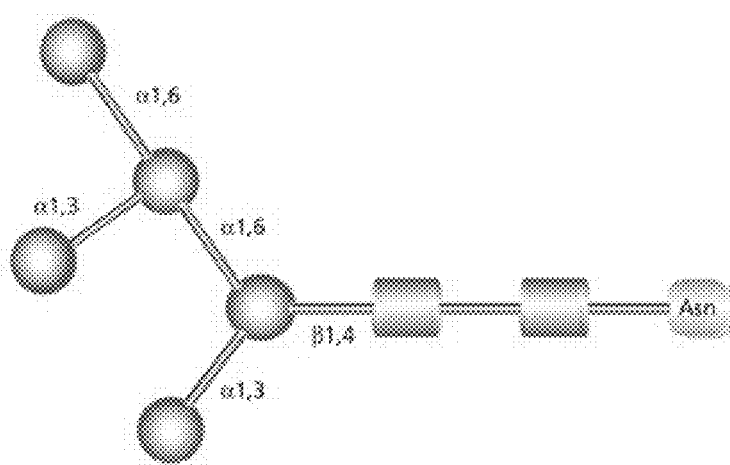

The mass of each fucosylated form of the glycans (G0F, G1F, and G2F) were also searched in the Potelligent® CHOK1SV produced αFGFR2b and were not observed. FIG. 8 shows schematic diagrams of the G0, G1, G2, G0F, G1F, G2F, and mannose-5 (or Man-5) glycan structures typically observed in antibodies.

The peak identities from the HPLC assay were also confirmed using glycan standards purchased from Prozyme and matching the retention time between the standards and the αFGFR2 profiles from both the Potelligent® CHOK1SV cell line and the CHOK1SV cell line. These standards were able to identify G0, G0F, Man5, G1, G1F, and G2F.

The results from the HPLC assay as well as the characterization data confirmed the lack of fucosylation in αFGFR2 derived from the Potelligent® CHOK1SV cell line.

Example 2: Afucosylated Anti-FGFR2b Antibody Binding Affinity

The binding affinities of αFGFR2bA and αFGFR2bF (the designation "F" after αFGFR2b refers to "fucosylated") for Fc gamma RIIIA(V158) were determined by surface plasmon resonance. Briefly, Protein A was covalently attached to a dextran chip using the Amine Coupling Kit (GE Healthcare Life Sciences, Piscataway, N.J.) and 100 mM ethylenediamine (Sigma) in 100 mM sodium borate buffer, pH 8.0 (Sigma, St. Louis, Mo.) as the blocking reagent. Approximately 600-800RU of αFGFR2bA and αFGFR2bF were captured on separate flow cells and a Protein A (Pierce) derivatized flow cell served as a reference control. Fc gamma RIIIA (V158) (R&D Systems, Minneapolis, Minn.) was diluted in HBS-P+ running buffer (Biacore, GE Healthcare, Piscataway, N.J.) and injected at 5 concentrations (0 nM, 12.3 nM, 37 nM, 111 nM, 333 nM, and 1000 nM) in duplicate. The association constant, dissociation constant, and affinity for αFGFR2bA were calculated using the Biacore T200 Evaluation Software 1:1 binding model. The affinity constant for αFGFR2bF binding was determined using the Biacore T200 Evaluation Software steady state affinity model. The results are shown in Table 3.

TABLE 3

| αFGFR2bA and αFGFR2bF antibody affinities for Fc gamma RIIIA(V158) | | | |
|---|---|---|---|
| αFGFR2b | $K_D$ ($k_d/k_a$) (nM) | $k_a$ (1/Ms) × 10^3 | $k_d$ (1/ms) |
| A | 9.2 | 940.1 | 8.6 |
| F | 207 | — | — |

As shown in Table 3, Fc gamma RIIIA(V158) bound αFGFR2bA with more than 20-fold greater affinity than it bound αFGFR2bF.

Example 3: Afucosylated Anti-FGFR2b Antibody ADCC Activity

In vitro assays to determine the ADCC activity of αFGFR2bA antibody versus αFGFR2bF antibody were performed. Ba/F3 FGFR2IIIb-expressing target cells were produced as follows. Ba/F3 cells acquired from Leibniz-Institut DSMZ-Deutsche Sammlung von Mikroorganismen and Zellkulturen GmbH (DSMZ, cat #ACC300, Braunschweig, Germany) were maintained in RPMI (Mediatech, cat #10-041-CV, Manassas, Va.), supplemented with 10% fetal bovine serum (Mediatech, cat #35-010-CV), 1 ng/mL murine IL-3 (Peprotech, cat #213-13, Rocky Hill, N.J.), 1×BME (Invitrogen, cat #1047574, Grand Island, N.Y.), and 1× Penicillin-streptomycin (Mediatech cat #30-002-C1). The Ba/F3 cells were transfected with an expression vector that expresses FGFR2IIIb, pBNew-hFGFR2b, using Cell Line Nucleofector® Kit V (Lonza, cat #VCA-1003) following the manufacturer's protocol. pBNew vector contains a CAG promoter with a chicken β-actin intron and ampicillin and puromycin growth selection genes. Transfected cells were incubated in full growth media for 3 days then treated with 2 μg/mL of puromycin (InVivoGen, cat #ant-pr-1, San Diego, Calif.). Puromycin selection was maintained throughout culturing. To generate individual stable clones, cells were plated at a density of 1 cell per 3 wells. Fluorescent activated cell sorting (FACS) with an anti-FGFR2IIIb antibody was used to select the clones with the highest level of FGFR2IIIb expression.

MFM-223 cells were obtained from the Health Protection Agency, UK; OCUM-2M cells were obtained from Osaka City University, Osaka, Japan; and KATO III cells were obtained from ATCC, Rockville, Md. All cells were cultured using standard methods. Freshly isolated PMBC from healthy donors were obtained from AllCells, Emeryville, Calif.

ADCC assays were conducted using effector cells from 3 independent donors on 3 different days. ADCC assay testing was performed using freshly isolated human PBMCs as effector cells at an effector to target (E/T) cell ratio of 25:1. The target cells were incubated for 16 hours in the presence of effectors and increasing concentrations of antibody. The ADCC assay was validated using 2 positive control antibodies, HERCEPTIN® on SKOV-3 target cells and RITUXIN® on Raji target cells. A fully human IgG1 negative control antibody (Eureka Therapeutics, Catalog ET901, Emeryville, Calif.) was used for non-specific cell cytotoxicity. Cytotoxicity was determined by quantifying LDH release as per the manufacturer's instructions (CytoTox Non Radioactive Cytotoxicity Assay, Promega, Madison, Wis.).

Figure 1B:
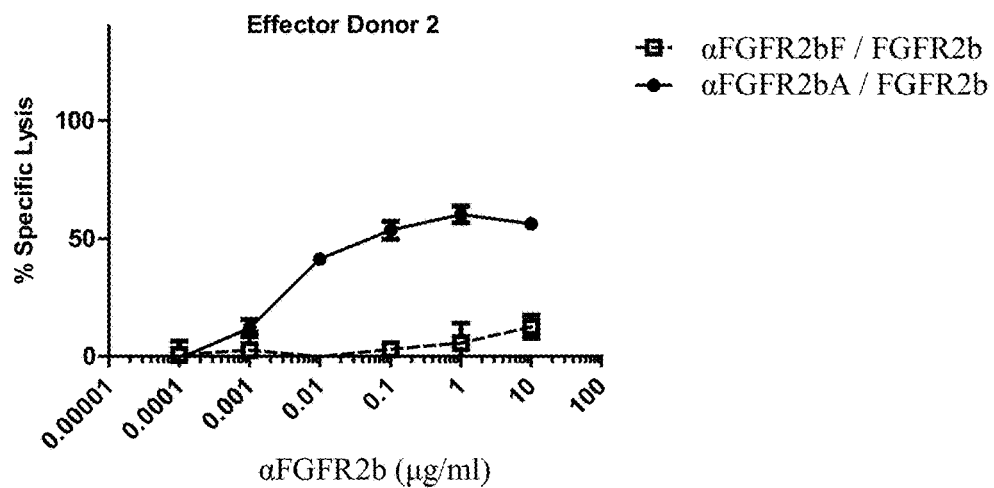
Figure 1C:
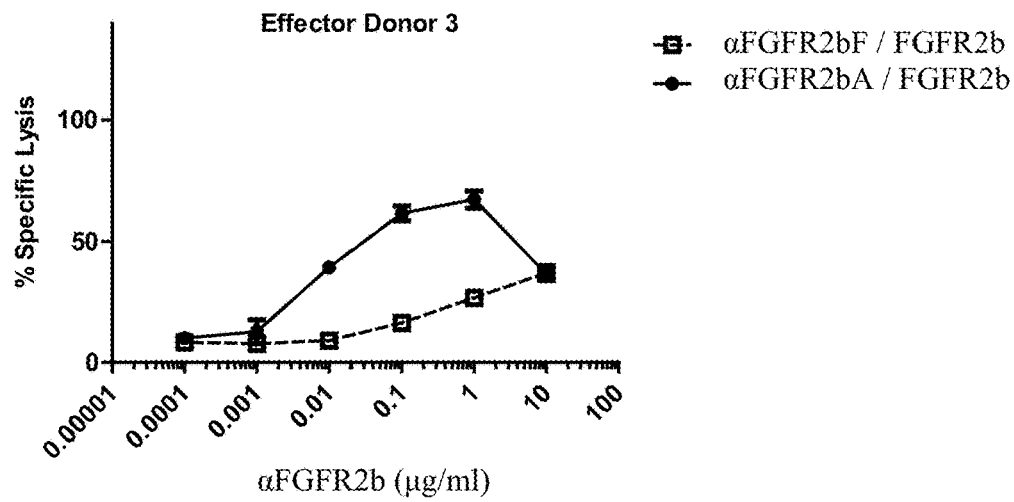
Figure 2A:
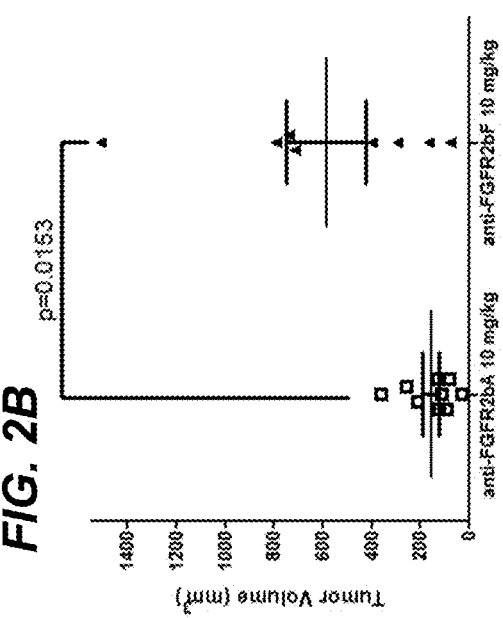
FIGS. 2A to 2D show efficacy of afucosylated αFGFR2bA and fucosylated αFGFR2bF in an OCUM-2M gastric cancer xenograft model, at (A and B) 10 mg/kg and (C and D) 3 mg/kg, as discussed in Example 4.
Figure 2B:
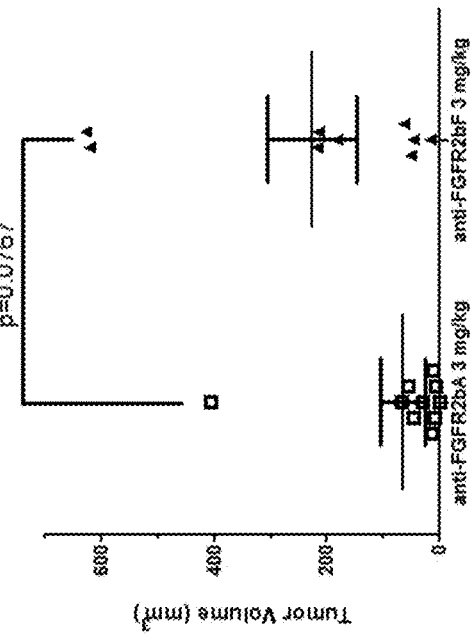
Figure 2C:
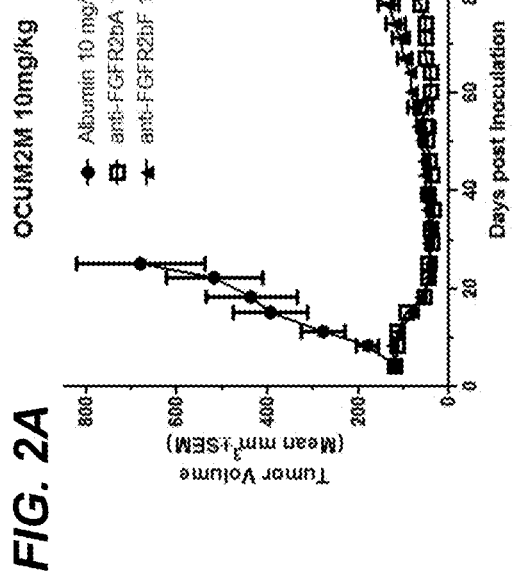
Figure 2D:
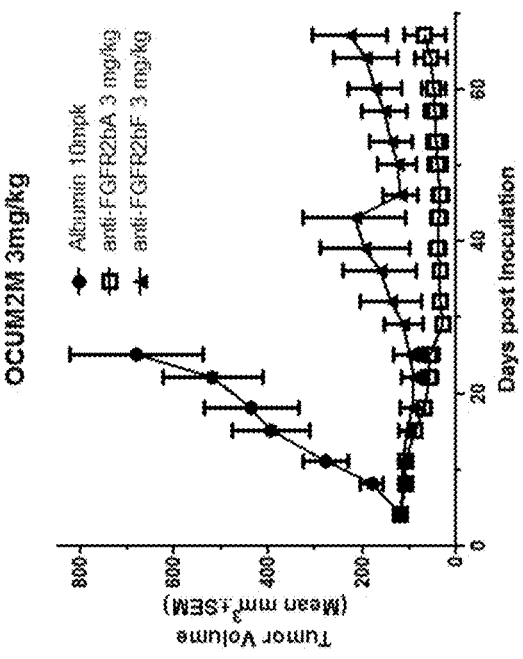

Maximal lysis was determined in the presence of 5% Triton X-100, and spontaneous release was determined in the absence of antibody. Percentage of specific lysis was calculated as follows, as a percentage of maximal lysis less spontaneous release:

(experimental−spontaneous release)/(maximal−spontaneous release)×100=% specific lysis The results for the Ba/F3 cells are shown in FIG. 1. Afucosylated αFGFR2bA antibody induced greater specific lysis than fucosylated αFGFR2bF antibody in FGFR2IIIb-expressing Ba/F3 cells. In OCUM-2M, MFM 223, and KATO III cells, αFGFR2bA showed greater ADCC activity at lower concentrations than αFGFR2bF, although maximal specific lysis of the antibodies was comparable in OCUM-2M and MFM 223 cells (data not shown). Further, αFGFR2b showed little to no ADCC activity in FGFR2IIIc-expressing Ba/F3 cells. See FIG. 1A.

Example 4: Afucosylated Anti-FGFR2b Antibody Activity in Gastric Cancer and Breast Cancer Xenograft Models Six week old female CB17 SCID mice were purchased from Charles River Laboratories (Wilmington, Mass.) and were acclimated for 1 week before the start of the study. Human gastric carcinoma cell line OCUM-2M or breast carcinoma cell line MFM-223 were used as the tumor models. OCUM-2M was purchased from Public University Corporation Osaka City University (OCU, Osaka, Japan), and MFM-223 was purchased from Culture Collections, Public Health England (98050130, HPA Culture Collections, Salisbury, UK). The cells were cultured for up to three passages in complete growth medium to expand for implantation. OCUM-2M and MFM-223 cells were cultured in Dulbecco's Minimum Essential Medium (DMEM) and Minimum Essential Medium (MEM), respectively. All medium was supplemented with 10% heat-inactivated Fetal Bovine Serum (FBS), 2 mM L-Glutamine, and Penicillin-Streptomycin solution. Cells were grown at 37° C. in a humidified atmosphere with 5% $CO_2$.

When the cultured cells reached 85-90% confluence, cells were harvested and resuspended in cold $Ca^{2+}$ and $Mg^{2+}$ free phosphate buffered saline (PBS) containing 50% Matrigel (BD BioSciences, San Jose, Calif.). OCUM-2M cells were implanted subcutaneously over the right flank of the mice at $5 \times 10^5$ cells/100 μl/mouse. MFM-223 cells were implanted subcutaneously over the right flank of the mice at $5 \times 10^5$ cells/100 μl/mouse, and 0.72 mg 90-day release 1713 estradiol pellets (Innovative Research of America, Sarasota, Fla.) were inoculated subcutaneously into the right flank. Mice were monitored twice weekly following cell implantation for tumor growth. Tumor size was measured according to the formula: Tumor size $(mm^3)$=(width (mm)×length $(mm)^2$)/2. When MFM-223 tumors reached 80 $mm^3$ mice were sorted and randomized (n=10), and treatment was initiated. For OCUM-2M tumors, single therapy with anti-FGFR2b was initiated once tumors reached an average size of 100 $mm^3$, and combination therapy was initiated once tumors reached an average size of 250 $mm^3$.

Anti-FGFR2IIIb humanized antibody (Afucosylated, αFGFR2bA; Fucosylated, αFGFR2bF) or albumin as a negative control was administered at doses ranging from 1 to 10 mg/kg via intraperitoneal injection twice per week as specified in the figure legends. Chemotherapeutic agents were administered via intraperitoneal injection twice per week at 12 mg/kg for paclitaxel, 2.3 mg/kg for fluorouracil (5-FU), and 33 mg/kg for cisplatin. Upon initiation of therapy, tumor sizes were measured in each mouse twice weekly. The length and width of each tumor was measured using calipers and the tumor size calculated according to the formula above. Mice were euthanized when the subcutaneous tumor volumes exceeded 2000 $mm^3$ or when the tumors became excessively necrotic.

Comparisons of tumor volume as a consequence of were determined to be statistically significant if P<0.05. P-values were calculated using unpaired, two-tailed t-test analyses of the calculated tumor volumes on the final day upon which tumors were measured.

FIG. 2 shows efficacy of αFGFR2bA and αFGFR2bF at (A and B) 10 mg/kg and (C and D) 3 mg/kg in an OCUM-2M human gastric cancer xenograft model with FGFR2 amplification. (A) At 10 mg/kg, both fucosylated and afucosylated antibody induced immediate tumor regression. However, afucosylated αFGFR2bA induced a more durable response than fucosylated αFGFR2bF. (B) Afucosylated αFGFR2bA significantly reduced final OCUM-2M tumor size compared to fucosylated αFGFR2bF (p=0.0153). Statistical significance was determined via two-tailed, unpaired t-Test. (C) When dosed at 3 mg/kg, afucosylated αFGFR2bA reduced tumor growth compared to fucosylated αFGFR2bF. Indeed, afucosylated αFGFR2bA induced greater tumor regression and durable response compared to fucosylated αFGFR2bF (note: one animal was removed from the αFGFR2bF group at about day 42, resulting in a shift in the curve). (D) Afucosylated αFGFR2bA at 3 mg/kg compared to fucosylated αFGFR2bF notably reduced final OCUM-2M tumor size (p=0.0767). Statistical significance was determined via two-tailed, unpaired t-Test.

Figure 3B:
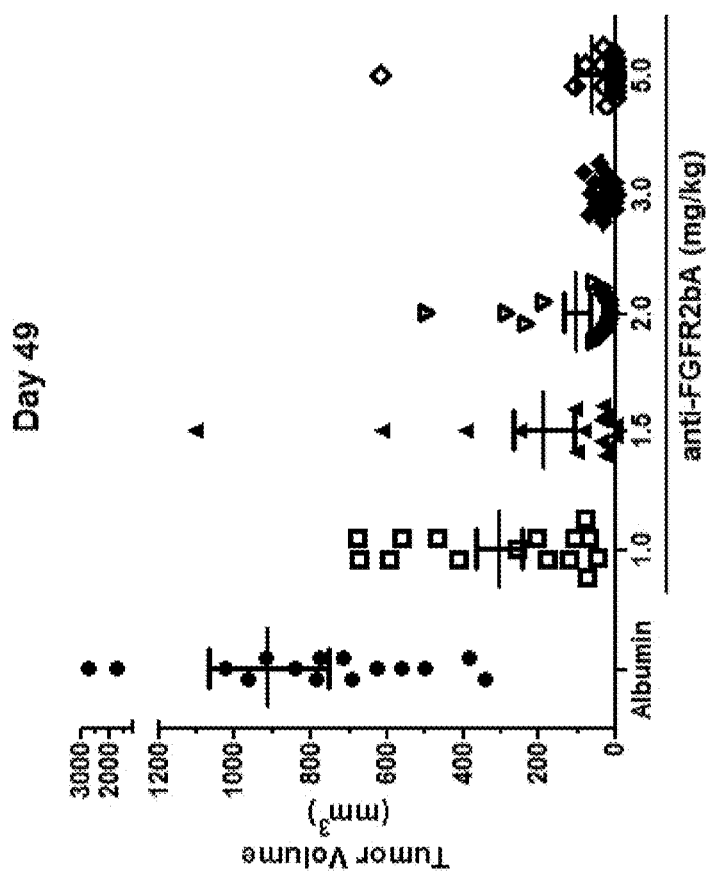
FIGS. 3A and 3B show dose-dependent efficacy of afucosylated αFGFR2bA in an OCUM-2M gastric cancer xenograft model, as discussed in Example 4.
Figure 3A:
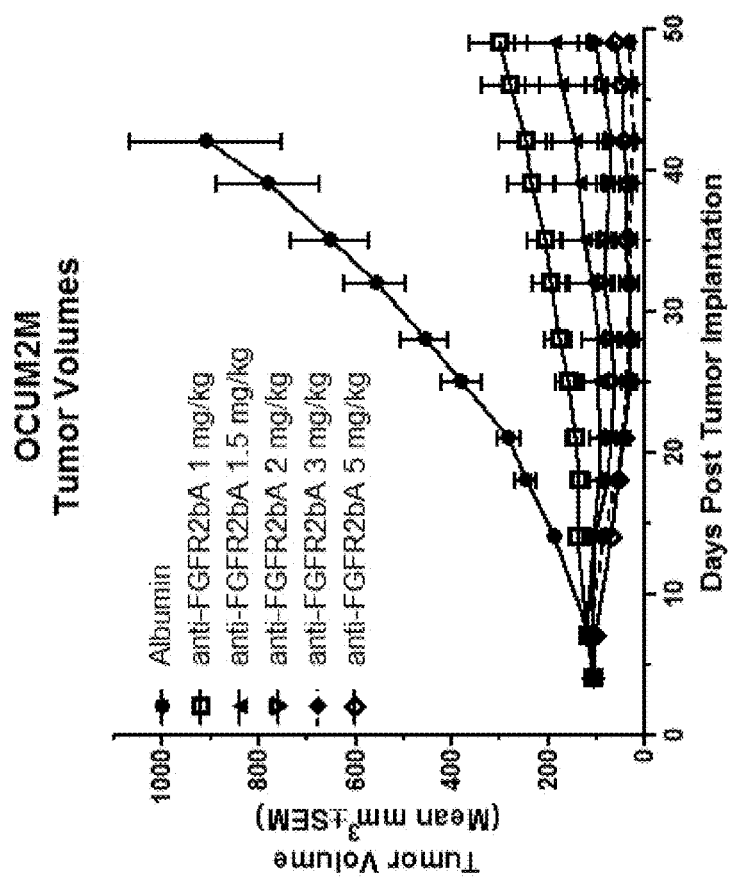

FIG. 3 shows dose-dependent tumor inhibition by αFGFR2bA. (A) SCID mice bearing subcutaneous OCUM-2M xenografts were treated with 1, 1.5, 2, 3, or 5 mg/kg afucosylated αFGFR2bA when average tumor size reached approximately 100 $mm^3$. Although all doses of afucosylated αFGFR2bA inhibited tumor growth, the greatest suppression and durable response were observed with 3 and 5 mg/kg, with reduced growth suppression observed with 2, 1.5, and 1 mg/kg αFGFR2bA. (B) Afucosylated αFGFR2bA reduced final OCUM-2M tumor size, with higher doses showing more potent growth suppression. Tumor growth suppression was statistically significant for all doses (5 mg/kg, p<0.0001; 3 mg/kg, p<0.0001; 2 mg/kg, p<0.0001; 1.5 mg/kg, p=0.0003; 1 mg/kg, p=0.0013). Statistical significance was determined via two-tailed, unpaired t-Test.

Figure 4B:
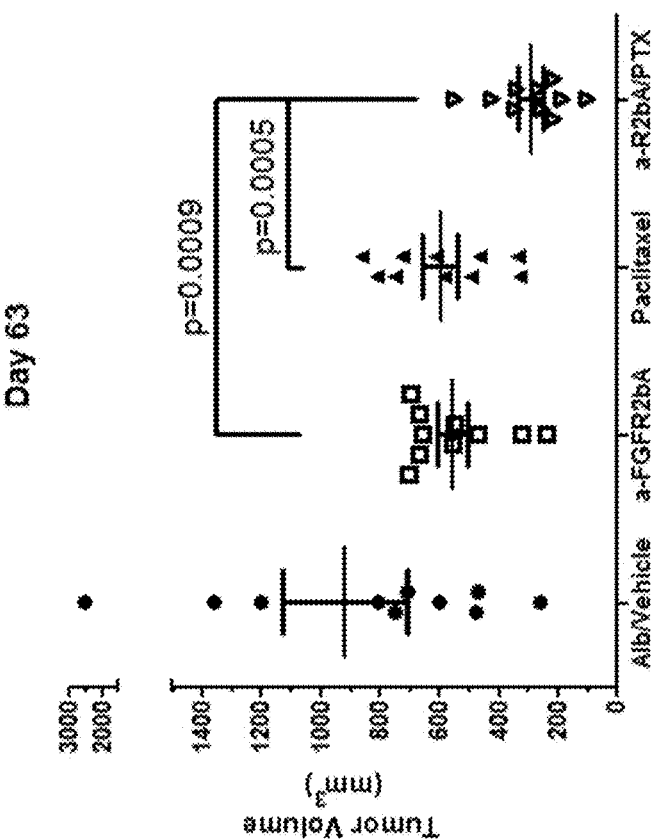
FIGS. 4A and 4B show efficacy of combination therapy with afucosylated αFGFR2bA and paclitaxel in an OCUM-2M gastric cancer xenograft model, as discussed in Example 4.
Figure 4A:
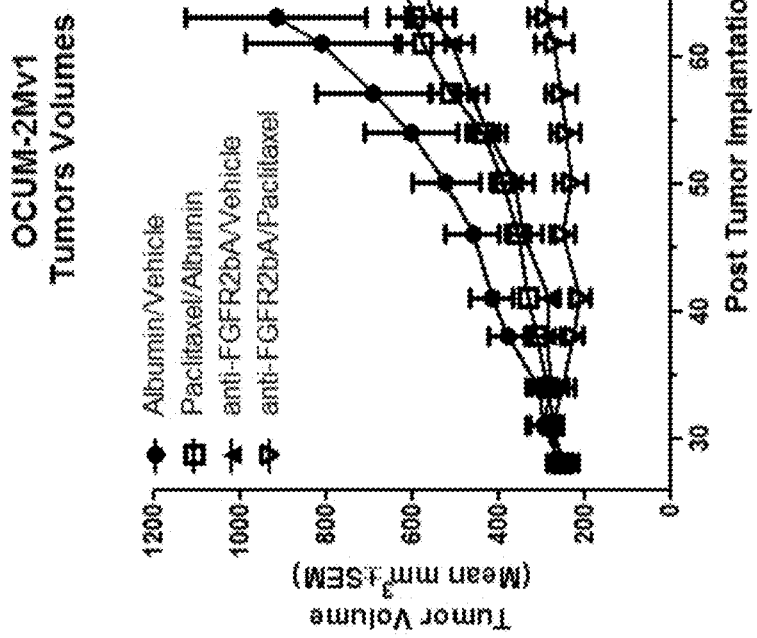

FIG. 4 shows enhancement of paclitaxel anti-tumor activity in an OCUM-2M gastric cancer xenograft model by administration with afucosylated αFGFR2bA. (A) SCID mice bearing subcutaneous OCUM-2M xenografts were treated with afucosylated αFGFR2bA (5 mg/kg), paclitaxel (12 mg/kg), or a combination of the two when average tumor size reached approximately 285 mm$^3$. Combining afucosylated αFGFR2bA with paclitaxel reduced tumor size compared to either αFGFR2bA or paclitaxel alone. (B) Combined αFGFR2bA/paclitaxel therapy significantly reduced final OCUM-2M tumor size compared to either paclitaxel (p=0.0005) or αFGFR2bA (p=0.0009) alone. Statistical significance was determined via two-tailed, unpaired t-Test.

Figure 5B:
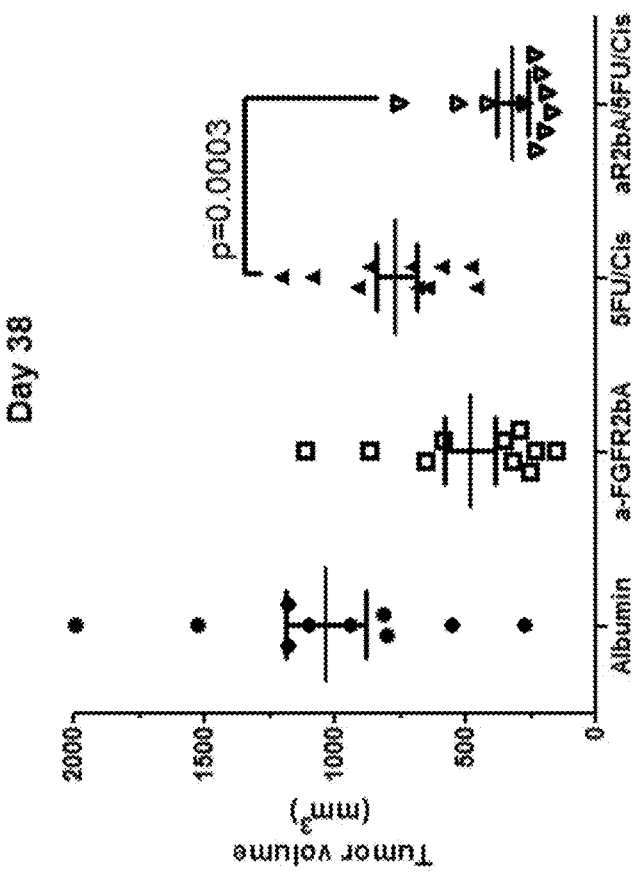
FIGS. 5A and 5B show efficacy of combination therapy with afucosylated αFGFR2bA and 5-FU/cisplatin in an OCUM-2M gastric cancer xenograft model, as discussed in Example 4.
Figure 5A:
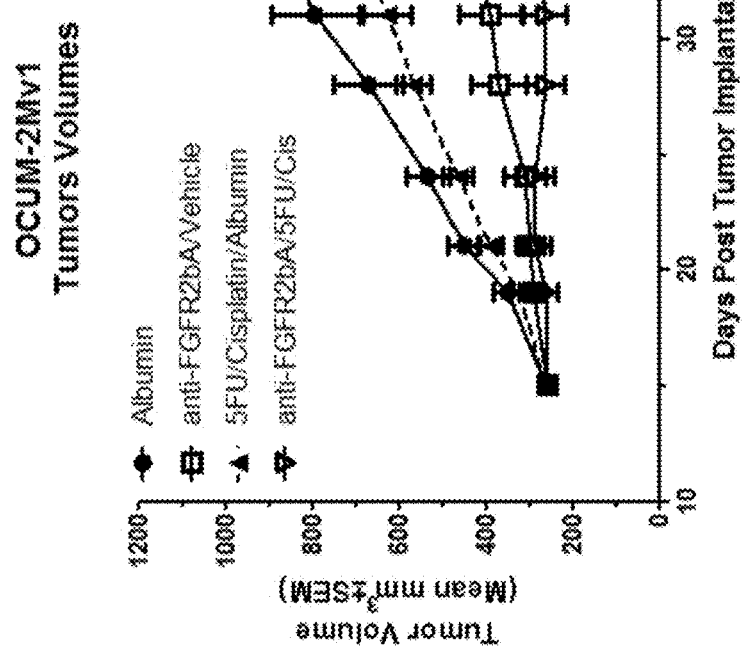

FIG. 5 shows enhancement of cisplatin/5-FU anti-tumor activity in an OCUM-2M gastric cancer xenograft model by administration with afucosylated αFGFR2bA. (A) SCID mice bearing subcutaneous OCUM-2M xenografts were treated with afucosylated αFGFR2bA (5 mg/kg), fluorouracil (5-FU) plus cisplatin (2.3 and 33 mg/kg, respectively), or a combination of the three when average tumor size reached approximately 260 mm$^3$. Combining afucosylated αFGFR2bA with 5-FU/cisplatin reduced tumor size compared to either αFGFR2bA or 5-FU/cisplatin alone. (B) Combined αFGFR2bA/5-FU/cisplatin therapy significantly reduced final OCUM-2M tumor size compared to 5-FU/cisplatin (p=0.0003). Increased reduction in tumor size by combined αFGFR2bA/5-FU/cisplatin therapy compared to αFGFR2bA alone was notable but not statistically significant. Statistical significance was determined via two-tailed, unpaired t-Test.

Figure 6B:
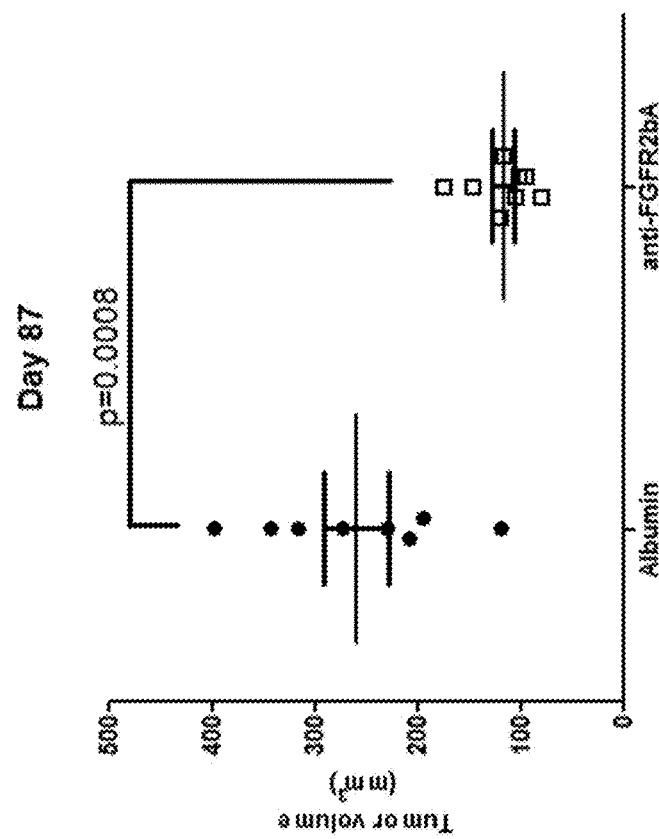
FIGS. 6A and 6B show efficacy of afucosylated αFGFR2bA in a MFM-223 breast cancer xenograft model, as discussed in Example 4.
Figure 6A:
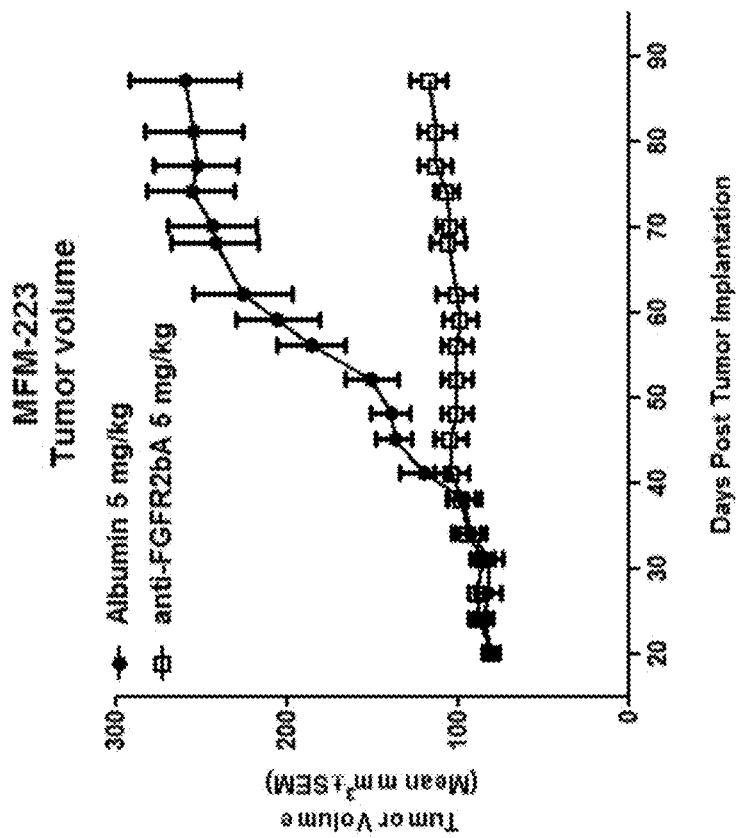

FIG. 6 shows efficacy of αFGFR2bA in an MFM-223 human breast cancer xenograft model. (A) MFM-223, a human breast carcinoma cell line with FGFR2 amplification, was implanted subcutaneously into SCID mice, and afucosylated αFGFR2bA therapy was initiated when average tumor size reached approximately 80 mm$^3$. Afucosylated αFGFR2bA (5 mg/kg) dramatically reduced growth of MFM-223 tumors compared to albumin control (5 mg/kg). (B) Afucosylated αFGFR2bA significantly reduced final MFM-223 tumor size compared to albumin control (p=0.0008). Statistical significance was determined via two-tailed, unpaired t-Test.

Example 5: Afucosylated Anti-FGFR2b Antibody Mediates Greater ADCC than Fucosylated Anti-FGFR2b Antibody In vitro assays to determine the ADCC activity of αFGFR2bA antibody versus αFGFR2bF antibody were performed. Ba/F3 FGFR2IIIb-expressing target cells were generated as described before. OCUM-2M cells were obtained from Osaka City University, Osaka, Japan. All cells were cultured using standard methods. Freshly isolated PMBC from healthy donors were obtained from AllCells, Emeryville, Calif.

ADCC assays were conducted using freshly isolated human PBMCs as effector cells at an effector to target (E:T) cell ratio of 25:1. The target cells were incubated for 16 hours in the presence of effectors and increasing concentrations of antibody. All conditions were tested in triplicate. Cytotoxicity was determined by quantifying LDH release as per the manufacturer's recommendations (Promega's Cyto-Tox Non-Radioactive Cytotoxicity Assay). For the OCUM-2M cells, maximal lysis was determined in the presence of 5% Triton X-100, and spontaneous release was determined in the absence of antibody. Percentage of specific lysis was calculated as a percentage of maximal lysis less spontaneous release, as follows: (experimental−spontaneous release)/(maximal−spontaneous release)×100=% specific lysis. GraphPad software curve-fitting analysis was used to obtain EC50 values.

Figure 9:
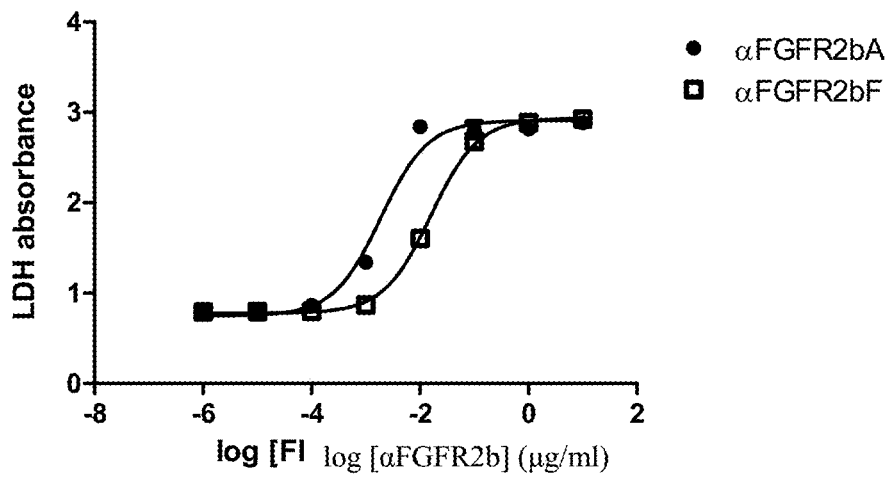
FIG. 9 shows ADCC of Ba/F3 FGF2b cells with increasing concentrations of αFGFR2bA or αFGFR2bF. Assays were performed with normal human PBMC at an E:T ratio of 25:1, as described in Example 5. Data are plotted as LDH release.
Figure 10:
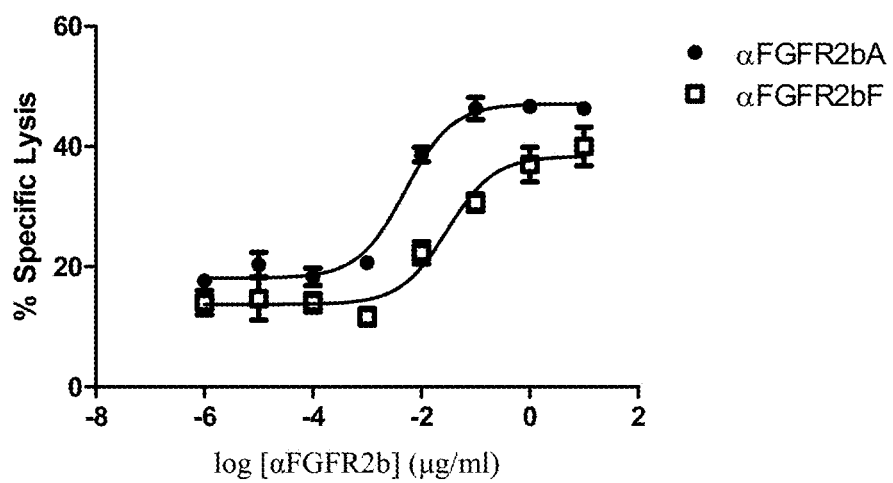
FIG. 10 shows ADCC of OCUM-2M cells with increasing concentrations of αFGFR2bA or αFGFR2bF. Assays were performed with normal human PBMC at an E:T ratio of 25:1. As described in Example 5. Data are plotted as percent specific lysis.
Figure 11C:
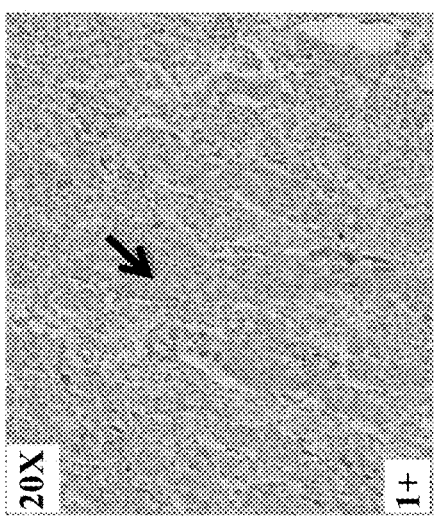
FIGS. 11A to 11F show detection of FGFR2IIIb in tumor tissue samples using immunohistochemistry, as described in Example 6.
Figure 11F:
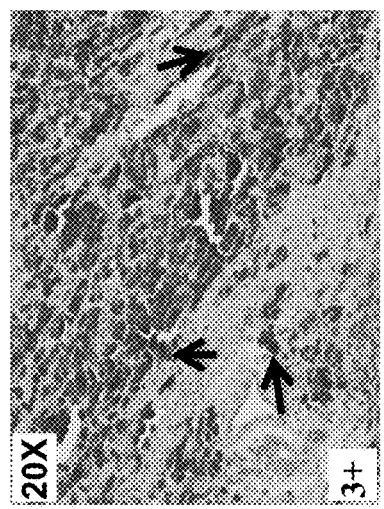
Figure 11B:
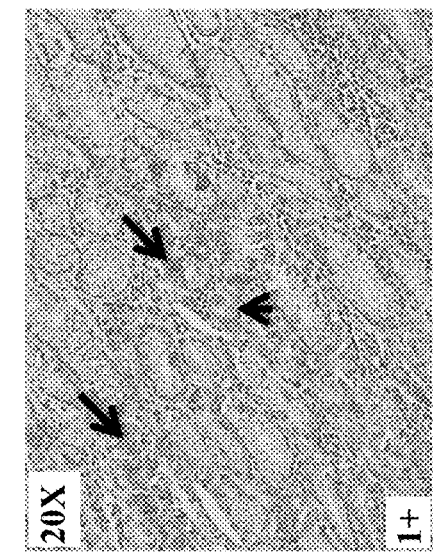
Figure 11E:
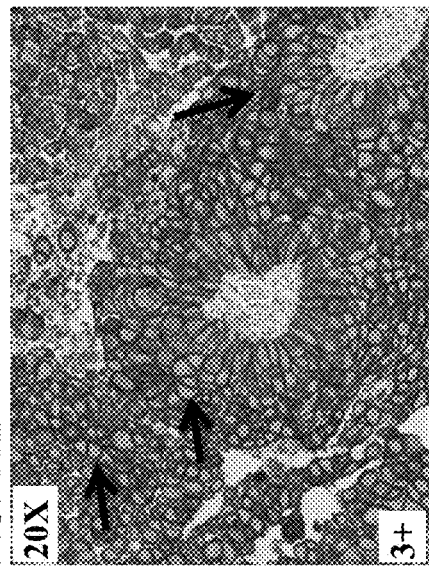
Figure 11A:
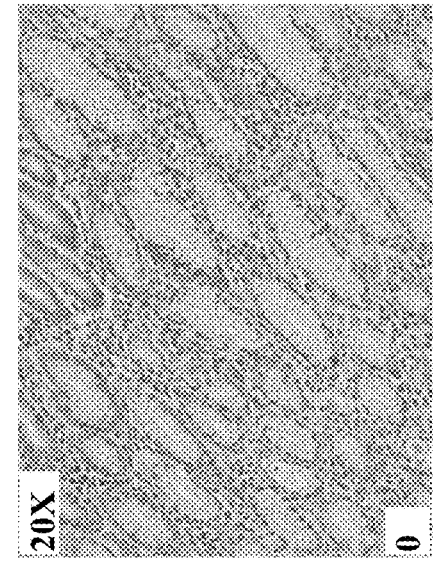
Figure 11D:
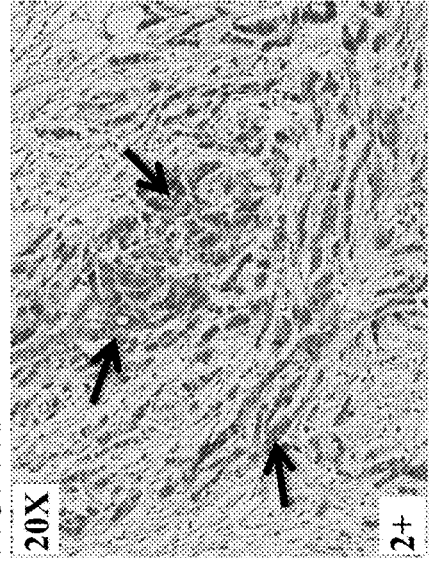

The results for the Ba/F3 cells are shown in FIG. 9. Afucosylated αFGFR2bA antibody showed higher potency (greater ADCC activity at lower concentrations) than fucosylated αFGFR2bF antibody in FGFR2IIIb-expressing Ba/F3 cells. Similar results are shown for OCUM-2M cells in FIG. 10. Table 4 shows the potency fold increase of afucosylated anti-FGFRb antibody compared to fucosylated anti-FGFR2b antibody in the two different cell lines shown in FIGS. 9 and 10.

TABLE 4

| Potency fold increase of afucosylated versus fucosylated anti-FGFR2b antibody EC50 (ng/mL) | | | |
|---|---|---|---|
| Cells | αFGFR2bA | αFGFR2bF | Potency Fold Increase of αFGFR2bA |
| OCUM-2M | 5 | 30 | 6 |
| BaF3 FGFR2b | 2 | 16 | 8 |

Example 6: Immunohistochemical Detection of FGFR2IIIb Protein in Tumor Tissue Murine αFGFR2b antibody comprising the murine variable regions of GAL-FR21 (see U.S. Pat. No. 8,101,723 B2) and a murine IgG2a constant region was used to detect FGFR2IIIb protein in formalin-fixed paraffin embedded (FFPE) gastric tumor tissue. FFPE tumor tissue as deparaffinized with successive washes of xylenes and decreasing concentrations of ethanol, and rehydrated with water for five minutes. Slide-mounted tissue sections were immersed in 0.1 mM citrate buffer (pH 6.0) heated to 95°-99° C. for 15 minutes. Tissue sections were cooled and contacted with 3% $H_2O_2$ for 5 minutes at room temperature, and then washed twice in TBST (0.05M Tris, 0.15M NaCl, 0.05% Tween 20) and blocked in blocking buffer (2.5% normal horse serum in TBST) for 30 minutes at room temperature. Tissue sections were then incubated with 5 μg/ml αFGFR2b antibody in blocking buffer for 30 minutes at room temperature. Incubation times between 30 minutes and 2 hours produced similar staining intensities. Following three washes with TBST buffer, tissue sections were incubated with ready-to-use (RTU) biotinylated secondary horse anti-mouse antibody (10 m/ml diluted in blocking buffer (Vector Laboratories, Burlingame, Calif.; Cat. No. PK-7200) for 30 minutes at room temperature. Tissue sections were washed twice with TBST buffer, and the incubated with RTU streptavidin-horse radish peroxidase (HRP; Vector Laboratories, Cat. No. PK-7200) for 30 minutes at room temperature. Detection was performed using 3',3'-diaminobenzidine (DAB) substrate (Vector Laboratories, Cat. No. PK-4105) for ten minutes at room temperature per manufacturer's instructions. Tissue sections were then counter-stained with hematoxylin (Dako North America, Carpinteria, Calif., Cat. No. K-8008) per manufacturer's instructions. Tissue sections were dehydrated using successive washes with increasing concentrations of ethanol and xylenes, and then covered with a coverslip.

Staining concentrations of 0.1 to 5 mg/ml αFGFR2b antibody were found to be particularly effective for protein detection.

The staining was scored as follows:

0 No staining with αFGFR2b antibody observed

1+ Faint staining is observed in samples stained with the αFGFR2b antibody. The staining is absent in corresponding sections stained with the negative control antibody.

2+ Membrane-cytoplasmic staining specific to αFGFR2b antibody is more prevalent in the sections.

3+ Strong specific staining with αFGFR2b antibody with distinct membrane localization in at least a subset of stained tumor cells.

FIG. 11 shows exemplary 0 (A), 1+(B, C), 2+(D), and 3+(E, F) staining of tumor tissues. In FIG. 11A, ductal cells and interspersed tumor cells show an absence of staining using the αFGFR2b antibody. In FIG. 11B, which shows an interstitial type gastric tumor sample, tumor cells (arrows) show some staining using the αFGFR2b antibody, while surrounding ductal cells show no staining. In FIG. 11C, which shows a diffuse-type gastric tumor sample, tumor cells (arrows) show some staining using the αFGFR2b antibody, while surrounding stromal cells (arrowheads) show no staining. In FIG. 11D, tumor cells (arrows) show intermediate staining using the αFGFR2b antibody, while surrounding stromal cells (arrowheads) show no staining. In FIG. 11E, tumor cells (arrows) show high membrane-localized staining using the αFGFR2b antibody, while surrounding stromal cells (arrowheads) show no staining. In FIG. 11F, tumor cells (arrows) show high membrane/cytoplasmic staining using the αFGFR2b antibody, while surrounding stromal cells (arrowheads) show no staining.

TABLE OF SEQUENCES

| SEQ ID NO | Description | Sequence |
|---|---|---|
| 1 | Mature human FGFR2IIIb | RPSFSLVED TTLEPEEPPT KYQISQPEVY VAAPGESLEV RCLLKDAAVI SWTKDGVHLG PNNRTVLIGE YLQIKGATPR DSGLYACTAS RTVDSETWYF MVNVTDAISS GDDEDDTDGA EDFVSENSNN KRAPYWTNTE KMEKRLHAVP AANTVKFRCP AGGNPMPTMR WLKNGKEFKQ EHRIGGYKVR NQHWSLIMES VVPSDKGNYT CVVENEYGSI NHTYHLDVVE RSPHRPILQA GLPANASTVV GGDVEFVCKV YSDAQPHIQW IKHVEKNGSK YGPDGLPYLK VLKHSGINSS NAEVLALFNV TEADAGEYIC KVSNYIGQAN QSAWLTVLPK QQAPGREKEI TASPDYLEIA IYCIGVFLIA CMVVTVILCR MKNTTKKPDF SSQPAVHKLT KRIPLRRQVT VSAESSSSMN SNTPLVRITT RLSSTADTPM LAGVSEYELP EDPKWEFPRD KLTLGKPLGE GCFGQVVMAE AVGIDKDKPK EAVTVAVKML KDDATEKDLS DLVSEMEMMK MIGKHKNIIN LLGACTQDGP LYVIVEYASK GNLREYLRAR RPPGMEYSYD INRVPEEQMT FKDLVSCTYQ LARGMEYLAS QKCIHRDLAA RNVLVTENNV MKIADFGLAR DINNIDYYKK TTNGRLPVKW MAPEALFDRV YTHQSDVWSF GVLMWEIFTL GGSPYPGIPV EELFKLLKEG HRMDKPANCT NELYMMMRDC WHAVPSQRPT FKQLVEDLDR ILTLTTNEEY LDLSQPLEQY SPSYPDTRSS CSSGDDSVFS PDPMPYEPCL PQYPHINGSV KT |
| 2 | αFGFR2b heavy chain; Asn297 is in bold and underlined | QVQLVQSGAE VKKPGSSVKV SCKASGYIFT TYNVHWVRQA PGQGLEWIGS IYPDNGDTSY NQNFKGRATI TADKSTSTAY MELSSLRSED TAVYYCARGD FAYWGQGTLV TVSSASTKGP SVFPLAPSSK STSGGTAALG CLVKDYFPEP VTVSWNSGAL TSGVHTFPAV LQSSGLYSLS SVVTVPSSSL GTQTYICNVN HKPSNTKVDK RVEPKSCDKT HTCPPCPAPE LLGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPQVYTLPP SREEMTKNQV SLTCLVKGFY PSDIAVEWES NGQPENNYKT TPPVLDSDGS FFLYSKLTVD KSRWQQGNVF SCSVMHEALH NHYTQKSLSL SPGK |
| 3 | αFGFR2b light chain | DIQMTQSPSS LSASVGDRVT ITCKASQGVS NDVAWYQQKP GKAPKLLIYS ASYRYTGVPS RFSGSGSGTD FTFTISSLQP EDIATYYCQQ HSTTPYTFGQ GTKLEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 4 | αFGFR2b heavy chain variable region | QVQLVQSGAE VKKPGSSVKV SCKASGYIFT TYNVHWVRQA PGQGLEWIGS IYPDNGDTSY NQNFKGRATI TADKSTSTAY MELSSLRSED TAVYYCARGD FAYWGQGTLV TVSS |
| 5 | αFGFR2b light chain variable region | DIQMTQSPSS LSASVGDRVT ITCKASQGVS NDVAWYQQKP GKAPKLLIYS ASYRYTGVPS RFSGSGSGTD FTFTISSLQP EDIATYYCQQ HSTTPYTFGQ GTKLEIK |

TABLE OF SEQUENCES-continued

| SEQ ID NO | Description | Sequence |
|---|---|---|
| 6 | αFGFR2b heavy chain (HC) HVR1 | TYNVH |
| 7 | αFGFR2b HC HVR2 | SIYPDNGDTS YNQNFKG |
| 8 | αFGFR2b HC HVR3 | GDFAY |
| 9 | αFGFR2b light chain (LC) HVR1 | KASQGVSNDV A |
| 10 | αFGFR2b LC HVR2 | SASYRYT |
| 11 | αFGFR2b LC HVR3 | QQHSTTPYT |
| 12 | Mature human FGFR2IIIc | RPSFSLVED TTLEPEEPPT KYQISQPEVY VAAPGESLEV RCLLKDAAVI SWTKDGVHLG PNNRTVLIGE YLQIKGATPR DSGLYACTAS RTVDSETWYF MVNVTDAISS GDDEDDTDGA EDFVSENSNN KRAPYWTNTE KMEKRLHAVP AANTVKFRCP AGGNPMPTMR WLKNGKEFKQ EHRIGGYKVR NQHWSLIMES VVPSDKGNYT CVVENEYGSI NHTYHLDVVE RSPHRPILQA GLPANASTVV GGDVEFVCKV YSDAQPHIQW IKHVEKNGSK YGPDGLPYLK VLKAAGVNTT DKEIEVLYIR NVTFEDAGEY TCLAGNSIGI SFHSAWLTVL PAPGREKEIT ASPDYLEIAI YCIGVFLIAC MVVTVILCRM KNTTKKPDFS SQPAVHKLTK RIPLRRQVTV SAESSSSMNS NTPLVRITTR LSSTADTPML AGVSEYELPE DPKWEFPRDK LTLGKPLGEG CFGQVVMAEA VGIDKDKPKE AVTVAVKMLK DDATEKDLSD LVSEMEMMKM IGKHKNIINL LGACTQDGPL YVIVEYASKG NLREYLRARR PPGMEYSYDI NRVPEEQMTF KDLVSCTYQL ARGMEYLASQ KCIHRDLAAR NVLVTENNVM KIADFGLARD INNIDYYKKT TNGRLPVKWM APEALFDRVY THQSDVWSFG VLMWEIFTLG GSPYPGIPVE ELFKLLKEGH RMDKPANCTN ELYMMMRDCW HAVPSQRPTF KQLVEDLDRI LTLTTNEEYL DLSQPLEQYS PSYPDTRSSC SSGDDSVFSP DPMPYEPCLP QYPHINGSVK T |

The invention claimed is:

1. A composition which can be used for treating solid tumors, comprising anti-FGFR2IIIb antibodies, wherein each anti-FGFR2IIIb antibody comprises heavy chain and light chain variable regions, wherein the heavy chain variable region comprises:
   (i) HVR-H1 comprising the amino acid sequence of SEQ ID NO: 6;
   (ii) HVR-H2 comprising the amino acid sequence of SEQ ID NO: 7; and
   (iii) HVR-H3 comprising the amino acid sequence of SEQ ID NO: 8;
   and the light chain variable region comprises:
   (iv) HVR-L1 comprising the amino acid sequence of SEQ ID NO: 9;
   (v) HVR-L2 comprising the amino acid sequence of SEQ ID NO: 10; and
   (vi) HVR-L3 comprising the amino acid sequence of SEQ ID NO: 11;
   wherein at least 95% of the anti-FGFR2IIIb antibodies in the composition are afucosylated.

2. The composition of claim 1, wherein the heavy chain variable region comprises the amino acid sequence of SEQ ID NO: 4.

3. The composition of claim 1, wherein the light chain variable region comprises the amino acid sequence of SEQ ID NO: 5.

4. The composition of claim 1, wherein the heavy chain variable region comprises the amino acid sequence of SEQ ID NO: 4 and the light chain variable region comprises the amino acid sequence of SEQ ID NO: 5.

5. The composition of claim 1, wherein the antibody heavy chain comprises the amino acid sequence of SEQ ID NO: 2.

6. The composition of claim 1, wherein the antibody light chain comprises the amino acid sequence of SEQ ID NO: 3.

7. The composition of claim 1, wherein the antibody heavy chain comprises the amino acid sequence of SEQ ID NO: 2 and the antibody light chain comprises the amino acid sequence of SEQ ID NO: 3.

8. The composition of claim 1, wherein the antibodies are monoclonal antibodies.

9. The composition of claim 1, wherein the antibodies are chimeric antibodies.

10. The composition of claim 1, wherein the antibodies are humanized antibodies.

11. The composition of claim 1, wherein the afucosylated antibodies lack fucose at Asn297.

12. The composition of claim 1, wherein the antibodies comprise a κ light chain constant region.

13. The composition of claim 1, wherein the antibodies comprise an IgG1 heavy chain constant region.

14. The composition of claim 1, wherein the afucosylated antibodies have enhanced ADCC activity in vitro compared to a fucosylated anti-FGFR2IIIb antibody having the same amino acid sequence.

15. The composition of claim 14, wherein the afucosylated anti-FGFR2IIIb antibodies cause specific lysis that is at least 30 percentage points greater than specific lysis with the fucosylated anti-FGFR2IIIb antibody.

16. The composition of claim 15, wherein ADCC activity is determined using Ba/F3 cells expressing FGFR2IIIb as target cells and isolated human PBMCs as effector cells.

17. The composition of claim 1, wherein the afucosylated antibodies have enhanced affinity for Fc gamma RIIIA compared to a fucosylated anti-FGFR2IIIb antibody having the same amino acid sequence.

18. The composition of claim 17, wherein the afucosylated anti-FGFR2IIIb antibodies bind to Fc gamma RIIIA with at least 3-fold greater affinity than the fucosylated anti-FGFR2IIIb antibody.

19. The composition of claim 18, wherein affinity for Fc gamma RIIIA is determined using surface plasmon resonance.

20. The composition of claim 17, wherein Fc gamma RIIIA is selected from Fc gamma RIIIA(V158) and Fc gamma RIIIA(F158).

21. The composition of claim 20, wherein Fc gamma RIIIA is Fc gamma RIIIA(V158).

22. The composition of claim 1, wherein the afucosylated anti-FGFR2IIIb antibodies do not bind to FGFR2IIIc.

23. The composition of claim 1, wherein fucose is not detectable in the composition.

24. A pharmaceutical composition comprising the composition of claim 1 and at least one pharmaceutically acceptable carrier.

25. An afucosylated anti-FGFR2IIIb antibody which can be used for treating solid tumors, comprising heavy chain and light chain variable regions, wherein the heavy chain variable region comprises:
- (i) HVR-H1 comprising the amino acid sequence of SEQ ID NO: 6;
- (ii) HVR-H2 comprising the amino acid sequence of SEQ ID NO: 7; and
- (iii) HVR-H3 comprising the amino acid sequence of SEQ ID NO: 8;

and the light chain variable region comprises:
- (iv) HVR-L1 comprising the amino acid sequence of SEQ ID NO: 9;
- (v) HVR-L2 comprising the amino acid sequence of SEQ ID NO: 10; and
- (vi) HVR-L3 comprising the amino acid sequence of SEQ ID NO: 11.

26. The afucosylated anti-FGFR2IIIb antibody of claim 25, wherein the heavy chain variable region comprises the amino acid sequence of SEQ ID NO: 4.

27. The afucosylated anti-FGFR2IIIb antibody of claim 25, wherein the light chain variable region comprises the amino acid sequence of SEQ ID NO: 5.

28. The afucosylated anti-FGFR2IIIb antibody of claim 25, wherein the heavy chain variable region comprises the amino acid sequence of SEQ ID NO: 4 and the light chain variable region comprises the amino acid sequence of SEQ ID NO: 5.

29. The afucosylated anti-FGFR2IIIb antibody of claim 25, wherein the antibody heavy chain comprises the amino acid sequence of SEQ ID NO: 2.

30. The afucosylated anti-FGFR2IIIb antibody of claim 25, wherein the antibody light chain comprises the amino acid sequence of SEQ ID NO: 3.

31. The afucosylated anti-FGFR2IIIb antibody of claim 25, wherein the antibody heavy chain comprises the amino acid sequence of SEQ ID NO: 2 and the antibody light chain comprises the amino acid sequence of SEQ ID NO: 3.

32. The afucosylated anti-FGFR2IIIb antibody of claim 25, wherein the antibodies are monoclonal antibodies.

33. The afucosylated anti-FGFR2IIIb antibody of claim 25, wherein the antibodies are chimeric antibodies.

34. The afucosylated anti-FGFR2IIIb antibody of claim 25, wherein the antibodies are humanized antibodies.

35. The afucosylated anti-FGFR2IIIb antibody of claim 25, wherein the antibodies lack fucose at Asn297.

36. The afucosylated anti-FGFR2IIIb antibody of claim 25, wherein the antibodies comprise a κ light chain constant region.

37. The afucosylated anti-FGFR2IIIb antibody of claim 25, wherein the antibodies comprise an IgG1 heavy chain constant region.

38. The afucosylated anti-FGFR2IIIb antibody of claim 25, wherein the afucosylated antibodies have enhanced ADCC activity in vitro compared to a fucosylated anti-FGFR2IIIb antibody having the same amino acid sequence.

39. The afucosylated anti-FGFR2IIIb antibody of claim 38, wherein the afucosylated anti-FGFR2IIIb antibodies cause specific lysis that is at least 30 percentage points greater than specific lysis with the fucosylated anti-FGFR2IIIb antibody.

40. The afucosylated anti-FGFR2IIIb antibody of claim 38, wherein ADCC activity is determined using Ba/F3 cells expressing FGFR2IIIb as target cells and isolated human PBMCs as effector cells.

41. The afucosylated anti-FGFR2IIIb antibody of claim 25, wherein the afucosylated antibodies have enhanced affinity for Fc gamma RIIIA compared to a fucosylated anti-FGFR2IIIb antibody having the same amino acid sequence.

42. The afucosylated anti-FGFR2IIIb antibody of claim 41, wherein the afucosylated anti-FGFR2IIIb antibodies bind to Fc gamma RIIIA with at least 3-fold greater affinity than the fucosylated anti-FGFR2IIIb antibody.

43. The afucosylated anti-FGFR2IIIb antibody of claim 42, wherein affinity for Fc gamma RIIIA is determined using surface plasmon resonance.

44. The afucosylated anti-FGFR2IIIb antibody of claim 42, wherein Fc gamma RIIIA is selected from Fc gamma RIIIA(V158) and Fc gamma RIIIA(F158).

45. The afucosylated anti-FGFR2IIIb antibody of claim 44, wherein Fc gamma RIIIA is Fc gamma RIIIA(V158).

46. The afucosylated anti-FGFR2IIIb antibody of claim 25, wherein the afucosylated anti-FGFR2IIIb antibodies do not bind to FGFR2IIIc.

47. A pharmaceutical composition comprising the afucosylated anti-FGFR2IIIb antibody of claim 25 and at least one pharmaceutically acceptable carrier.

48. The pharmaceutical composition of claim 1, wherein the antibody heavy chain variable region comprises the amino acid sequence of SEQ ID NO: 4 and the light chain variable region comprises the amino acid sequence of SEQ ID NO: 5, wherein the afucosylated antibodies lack fucose at Asn297, and wherein the antibodies comprise an IgG1 constant region.

49. The afucosylated anti-FGFR2IIIb antibody of claim 25, wherein the heavy chain variable region comprises the amino acid sequence of SEQ ID NO: 4 and the light chain variable region comprises the amino acid sequence of SEQ ID NO: 5, wherein the antibody lacks fucose at Asn297, and wherein the antibody comprises an IgG1 constant region.

50. The composition of claim 1, wherein the antibody heavy chain comprises the amino acid sequence of SEQ ID NO: 2 and the light chain comprises the amino acid sequence of SEQ ID NO: 3, and wherein the afucosylated antibodies lack fucose at Asn297.

51. The afucosylated anti-FGFR2IIIb antibody of claim 25, wherein the antibody heavy chain comprises the amino acid sequence of SEQ ID NO: 2 and the antibody light chain comprises the amino acid sequence of SEQ ID NO: 3, and wherein the antibody lacks fucose at Asn297.

52. A composition which can be used for treating solid tumors, comprising afucosylated anti-FGFR2IIIb antibodies, wherein fucose at Asn297 is detectable in less than about 5% of the anti-FGFR2IIIb antibodies, the anti-FGFR2IIIb antibodies comprising heavy chain and light chain variable regions, wherein the heavy chain variable region comprises:
- (i) HVR-H1 comprising the amino acid sequence of SEQ ID NO: 6;
- (ii) HVR-H2 comprising the amino acid sequence of SEQ ID NO: 7; and
- (iii) HVR-H3 comprising the amino acid sequence of SEQ ID NO: 8;

and the light chain variable region comprises:
- (iv) HVR-L1 comprising the amino acid sequence of SEQ ID NO: 9;
- (v) HVR-L2 comprising the amino acid sequence of SEQ ID NO: 10; and (vi) HVR-L3 comprising the amino acid sequence of SEQ ID NO: 11; and wherein:
  (a) the anti-FGFR2IIIb antibodies bind to FGFR2IIIb and inhibit FGFR2 signaling; and
  (b) the anti-FGFR2IIIb antibodies induce enhanced ADCC activity.

53. The composition of claim 52, wherein the afucosylated anti-FGFR2IIIb antibodies block FGFR2IIIb if administered to a tumor where FGFR2 is overexpressed due to FGFR2 amplification or overexpression.

54. The composition of claim 52, wherein the afucosylated anti-FGFR2IIIb antibodies mediate ADCC in the presence of human effector cells more effectively than a second antibody that is fucosylated, wherein the second antibody has the same amino acid sequence as the afucosylated anti-FGFR2IIIb antibody.

55. The composition of claim 52, wherein the afucosylated anti-FGFR2IIIb antibodies bind to Fc gamma RIIIA with at least 2-fold or greater affinity than a fucosylated anti-FGFR2IIIb antibody having the same sequence as the afucosylated antibody, wherein said affinity is measured by surface plasmon resonance.

56. The composition of claim 52, wherein the afucosylated anti-FGFR2IIIb antibodies have enhanced affinity for Fc gamma RIIIA compared to a fucosylated anti-FGFR2IIIb antibody having the same amino acid sequence.

57. The composition of claim 56, wherein the afucosylated anti-FGFR2IIIb antibodies bind to Fc gamma RIIIA with at least 3-fold greater affinity than the fucosylated anti-FGFR2IIIb antibody.

58. The composition of claim 55, wherein Fc gamma RIIIA is Fc gamma RIIIA(V158).

59. The composition of claim 52, wherein the afucosylated anti-FGFR2IIIb antibodies do not bind to FGFR2IIIc.

* * * * *

SEQUENCE LISTING

<160> NUMBER OF SEQ ID NOS: 12

<210> SEQ ID NO 1
<211> LENGTH: 801
<212> TYPE: PRT
<213> ORGANISM: Homo sapiens

<400> SEQUENCE: 1

```
Arg Pro Ser Phe Ser Leu Val Glu Asp Thr Thr Leu Glu Pro Glu Glu
1               5                   10                  15

Pro Pro Thr Lys Tyr Gln Ile Ser Gln Pro Glu Val Tyr Val Ala Ala
            20                  25                  30

Pro Gly Glu Ser Leu Glu Val Arg Cys Leu Leu Lys Asp Ala Ala Val
        35                  40                  45

Ile Ser Trp Thr Lys Asp Gly Val His Leu Gly Pro Asn Asn Arg Thr
    50                  55                  60

Val Leu Ile Gly Glu Tyr Leu Gln Ile Lys Gly Ala Thr Pro Arg Asp
65                  70                  75                  80

Ser Gly Leu Tyr Ala Cys Thr Ala Ser Arg Thr Val Asp Ser Glu Thr
                85                  90                  95

Trp Tyr Phe Met Val Asn Val Thr Asp Ala Ile Ser Ser Gly Asp Asp
            100                 105                 110
```

```
Glu Asp Asp Thr Asp Gly Ala Glu Asp Phe Val Ser Glu Asn Ser Asn
        115                 120                 125

Asn Lys Arg Ala Pro Tyr Trp Thr Asn Thr Glu Lys Met Glu Lys Arg
    130                 135                 140

Leu His Ala Val Pro Ala Ala Asn Thr Val Lys Phe Arg Cys Pro Ala
145                 150                 155                 160

Gly Gly Asn Pro Met Pro Thr Met Arg Trp Leu Lys Asn Gly Lys Glu
                165                 170                 175

Phe Lys Gln Glu His Arg Ile Gly Gly Tyr Lys Val Arg Asn Gln His
            180                 185                 190

Trp Ser Leu Ile Met Glu Ser Val Val Pro Ser Asp Lys Gly Asn Tyr
        195                 200                 205

Thr Cys Val Val Glu Asn Glu Tyr Gly Ser Ile Asn His Thr Tyr His
    210                 215                 220

Leu Asp Val Val Glu Arg Ser Pro His Arg Pro Ile Leu Gln Ala Gly
225                 230                 235                 240

Leu Pro Ala Asn Ala Ser Thr Val Val Gly Gly Asp Val Glu Phe Val
                245                 250                 255

Cys Lys Val Tyr Ser Asp Ala Gln Pro His Ile Gln Trp Ile Lys His
            260                 265                 270

Val Glu Lys Asn Gly Ser Lys Tyr Gly Pro Asp Gly Leu Pro Tyr Leu
        275                 280                 285

Lys Val Leu Lys His Ser Gly Ile Asn Ser Ser Asn Ala Glu Val Leu
    290                 295                 300

Ala Leu Phe Asn Val Thr Glu Ala Asp Ala Gly Glu Tyr Ile Cys Lys
305                 310                 315                 320

Val Ser Asn Tyr Ile Gly Gln Ala Asn Gln Ser Ala Trp Leu Thr Val
                325                 330                 335

Leu Pro Lys Gln Gln Ala Pro Gly Arg Glu Lys Glu Ile Thr Ala Ser
            340                 345                 350

Pro Asp Tyr Leu Glu Ile Ala Ile Tyr Cys Ile Gly Val Phe Leu Ile
        355                 360                 365

Ala Cys Met Val Val Thr Val Ile Leu Cys Arg Met Lys Asn Thr Thr
    370                 375                 380

Lys Lys Pro Asp Phe Ser Ser Gln Pro Ala Val His Lys Leu Thr Lys
385                 390                 395                 400

Arg Ile Pro Leu Arg Arg Gln Val Thr Val Ser Ala Glu Ser Ser Ser
                405                 410                 415

Ser Met Asn Ser Asn Thr Pro Leu Val Arg Ile Thr Thr Arg Leu Ser
            420                 425                 430

Ser Thr Ala Asp Thr Pro Met Leu Ala Gly Val Ser Glu Tyr Glu Leu
        435                 440                 445

Pro Glu Asp Pro Lys Trp Glu Phe Pro Arg Asp Lys Leu Thr Leu Gly
    450                 455                 460

Lys Pro Leu Gly Glu Gly Cys Phe Gly Gln Val Val Met Ala Glu Ala
465                 470                 475                 480

Val Gly Ile Asp Lys Asp Lys Pro Lys Glu Ala Val Thr Val Ala Val
                485                 490                 495

Lys Met Leu Lys Asp Asp Ala Thr Glu Lys Asp Leu Ser Asp Leu Val
            500                 505                 510

Ser Glu Met Glu Met Met Lys Met Ile Gly Lys His Lys Asn Ile Ile
        515                 520                 525
```

-continued

```
Asn Leu Leu Gly Ala Cys Thr Gln Asp Gly Pro Leu Tyr Val Ile Val
530                 535                 540

Glu Tyr Ala Ser Lys Gly Asn Leu Arg Glu Tyr Leu Arg Ala Arg Arg
545                 550                 555                 560

Pro Pro Gly Met Glu Tyr Ser Tyr Asp Ile Asn Arg Val Pro Glu Glu
                565                 570                 575

Gln Met Thr Phe Lys Asp Leu Val Ser Cys Thr Tyr Gln Leu Ala Arg
            580                 585                 590

Gly Met Glu Tyr Leu Ala Ser Gln Lys Cys Ile His Arg Asp Leu Ala
        595                 600                 605

Ala Arg Asn Val Leu Val Thr Glu Asn Asn Val Met Lys Ile Ala Asp
610                 615                 620

Phe Gly Leu Ala Arg Asp Ile Asn Asn Ile Asp Tyr Tyr Lys Lys Thr
625                 630                 635                 640

Thr Asn Gly Arg Leu Pro Val Lys Trp Met Ala Pro Glu Ala Leu Phe
                645                 650                 655

Asp Arg Val Tyr Thr His Gln Ser Asp Val Trp Ser Phe Gly Val Leu
            660                 665                 670

Met Trp Glu Ile Phe Thr Leu Gly Gly Ser Pro Tyr Pro Gly Ile Pro
        675                 680                 685

Val Glu Glu Leu Phe Lys Leu Leu Lys Glu Gly His Arg Met Asp Lys
690                 695                 700

Pro Ala Asn Cys Thr Asn Glu Leu Tyr Met Met Met Arg Asp Cys Trp
705                 710                 715                 720

His Ala Val Pro Ser Gln Arg Pro Thr Phe Lys Gln Leu Val Glu Asp
                725                 730                 735

Leu Asp Arg Ile Leu Thr Leu Thr Thr Asn Glu Glu Tyr Leu Asp Leu
            740                 745                 750

Ser Gln Pro Leu Glu Gln Tyr Ser Pro Ser Tyr Pro Asp Thr Arg Ser
        755                 760                 765

Ser Cys Ser Ser Gly Asp Asp Ser Val Phe Ser Pro Asp Pro Met Pro
770                 775                 780

Tyr Glu Pro Cys Leu Pro Gln Tyr Pro His Ile Asn Gly Ser Val Lys
785                 790                 795                 800

Thr
```

```
<210> SEQ ID NO 2
<211> LENGTH: 444
<212> TYPE: PRT
<213> ORGANISM: Artificial sequence
<220> FEATURE:
<223> OTHER INFORMATION: Synthetic

<400> SEQUENCE: 2

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Thr Thr Tyr
            20                  25                  30

Asn Val His Trp Val Arg Gln Ala Pro Gly Gln Gly Leu Glu Trp Ile
        35                  40                  45

Gly Ser Ile Tyr Pro Asp Asn Gly Asp Thr Ser Tyr Asn Gln Asn Phe
    50                  55                  60

Lys Gly Arg Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
```

```
                    85                  90                  95

Ala Arg Gly Asp Phe Ala Tyr Trp Gly Gln Gly Thr Leu Val Thr Val
                100                 105                 110

Ser Ser Ala Ser Thr Lys Gly Pro Ser Val Phe Pro Leu Ala Pro Ser
                115                 120                 125

Ser Lys Ser Thr Ser Gly Gly Thr Ala Ala Leu Gly Cys Leu Val Lys
            130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
                180                 185                 190

Gln Thr Tyr Ile Cys Asn Val Asn His Lys Pro Ser Asn Thr Lys Val
                195                 200                 205

Asp Lys Arg Val Glu Pro Lys Ser Cys Asp Lys Thr His Thr Cys Pro
            210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
                260                 265                 270

Asn Trp Tyr Val Asp Gly Val Glu Val His Asn Ala Lys Thr Lys Pro
                275                 280                 285

Arg Glu Glu Gln Tyr Asn Ser Thr Tyr Arg Val Val Ser Val Leu Thr
            290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
                340                 345                 350

Glu Glu Met Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys
            435                 440

<210> SEQ ID NO 3
<211> LENGTH: 214
<212> TYPE: PRT
<213> ORGANISM: Artificial sequence
<220> FEATURE:
<223> OTHER INFORMATION: Synthetic

<400> SEQUENCE: 3

Asp Ile Gln Met Thr Gln Ser Pro Ser Ser Leu Ser Ala Ser Val Gly
```

-continued

```
              1               5                  10                 15
            Asp Arg Val Thr Ile Thr Cys Lys Ala Ser Gln Gly Val Ser Asn Asp
                            20                  25                 30

Val Ala Trp Tyr Gln Gln Lys Pro Gly Lys Ala Pro Lys Leu Leu Ile
                        35                  40                 45

Tyr Ser Ala Ser Tyr Arg Tyr Thr Gly Val Pro Ser Arg Phe Ser Gly
                    50                  55                 60

Ser Gly Ser Gly Thr Asp Phe Thr Phe Thr Ile Ser Ser Leu Gln Pro
            65                  70                  75                 80

Glu Asp Ile Ala Thr Tyr Tyr Cys Gln Gln His Ser Thr Thr Pro Tyr
                            85                  90                 95

Thr Phe Gly Gln Gly Thr Lys Leu Glu Ile Lys Arg Thr Val Ala Ala
                            100                 105                110

Pro Ser Val Phe Ile Phe Pro Pro Ser Asp Glu Gln Leu Lys Ser Gly
                        115                 120                125

Thr Ala Ser Val Val Cys Leu Leu Asn Asn Phe Tyr Pro Arg Glu Ala
                        130                 135                140

Lys Val Gln Trp Lys Val Asp Asn Ala Leu Gln Ser Gly Asn Ser Gln
            145                 150                 155                160

Glu Ser Val Thr Glu Gln Asp Ser Lys Asp Ser Thr Tyr Ser Leu Ser
                            165                 170                175

Ser Thr Leu Thr Leu Ser Lys Ala Asp Tyr Glu Lys His Lys Val Tyr
                        180                 185                 190

Ala Cys Glu Val Thr His Gln Gly Leu Ser Ser Pro Val Thr Lys Ser
                        195                 200                205

Phe Asn Arg Gly Glu Cys
                210

<210> SEQ ID NO 4
<211> LENGTH: 114
<212> TYPE: PRT
<213> ORGANISM: Artificial sequence
<220> FEATURE:
<223> OTHER INFORMATION: Synthetic

<400> SEQUENCE: 4

Gln Val Gln Leu Val Gln Ser Gly Ala Glu Val Lys Lys Pro Gly Ser
            1               5                  10                 15

Ser Val Lys Val Ser Cys Lys Ala Ser Gly Tyr Ile Phe Thr Thr Tyr
                            20                  25                 30

Asn Val His Trp Val Arg Gln Ala Pro Gly Gln Gly Leu Glu Trp Ile
                        35                  40                 45

Gly Ser Ile Tyr Pro Asp Asn Gly Asp Thr Ser Tyr Asn Gln Asn Phe
                    50                  55                 60

Lys Gly Arg Ala Thr Ile Thr Ala Asp Lys Ser Thr Ser Thr Ala Tyr
            65                  70                  75                 80

Met Glu Leu Ser Ser Leu Arg Ser Glu Asp Thr Ala Val Tyr Tyr Cys
                            85                  90                 95

Ala Arg Gly Asp Phe Ala Tyr Trp Gly Gln Gly Thr Leu Val Thr Val
                            100                 105                110

Ser Ser

<210> SEQ ID NO 5
<211> LENGTH: 107
<212> TYPE: PRT
<213> ORGANISM: Artificial sequence
```

```
<220> FEATURE:
<223> OTHER INFORMATION: Synthetic

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Gly Val Ser Asn Asp
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Ser Thr Thr Pro Tyr
                85                  90                  95

Thr Phe Gly Gln Gly Thr Lys Leu Glu Ile Lys
            100                 105

<210> SEQ ID NO 6
<211> LENGTH: 5
<212> TYPE: PRT
<213> ORGANISM: Artificial sequence
<220> FEATURE:
<223> OTHER INFORMATION: Synthetic

<400> SEQUENCE: 6

Thr Tyr Asn Val His
1               5

<210> SEQ ID NO 7
<211> LENGTH: 17
<212> TYPE: PRT
<213> ORGANISM: Artificial sequence
<220> FEATURE:
<223> OTHER INFORMATION: Synthetic

<400> SEQUENCE: 7

Ser Ile Tyr Pro Asp Asn Gly Asp Thr Ser Tyr Asn Gln Asn Phe Lys
1               5                   10                  15

Gly

<210> SEQ ID NO 8
<211> LENGTH: 5
<212> TYPE: PRT
<213> ORGANISM: Artificial sequence
<220> FEATURE:
<223> OTHER INFORMATION: Synthetic

<400> SEQUENCE: 8

Gly Asp Phe Ala Tyr
1               5

<210> SEQ ID NO 9
<211> LENGTH: 11
<212> TYPE: PRT
<213> ORGANISM: Artificial sequence
<220> FEATURE:
<223> OTHER INFORMATION: Synthetic

<400> SEQUENCE: 9

Lys Ala Ser Gln Gly Val Ser Asn Asp Val Ala
1               5                   10
```

```
<210> SEQ ID NO 10
<211> LENGTH: 7
<212> TYPE: PRT
<213> ORGANISM: Artificial sequence
<220> FEATURE:
<223> OTHER INFORMATION: Synthetic

<400> SEQUENCE: 10

Ser Ala Ser Tyr Arg Tyr Thr
1               5

<210> SEQ ID NO 11
<211> LENGTH: 9
<212> TYPE: PRT
<213> ORGANISM: Artificial sequence
<220> FEATURE:
<223> OTHER INFORMATION: Synthetic

<400> SEQUENCE: 11

Gln Gln His Ser Thr Thr Pro Tyr Thr
1               5

<210> SEQ ID NO 12
<211> LENGTH: 800
<212> TYPE: PRT
<213> ORGANISM: Homo sapiens

<400> SEQUENCE: 12

Arg Pro Ser Phe Ser Leu Val Glu Asp Thr Thr Leu Glu Pro Glu Glu
1               5                   10                  15

Pro Pro Thr Lys Tyr Gln Ile Ser Gln Pro Glu Val Tyr Val Ala Ala
            20                  25                  30

Pro Gly Glu Ser Leu Glu Val Arg Cys Leu Leu Lys Asp Ala Ala Val
        35                  40                  45

Ile Ser Trp Thr Lys Asp Gly Val His Leu Gly Pro Asn Asn Arg Thr
    50                  55                  60

Val Leu Ile Gly Glu Tyr Leu Gln Ile Lys Gly Ala Thr Pro Arg Asp
65                  70                  75                  80

Ser Gly Leu Tyr Ala Cys Thr Ala Ser Arg Thr Val Asp Ser Glu Thr
                85                  90                  95

Trp Tyr Phe Met Val Asn Val Thr Asp Ala Ile Ser Ser Gly Asp Asp
            100                 105                 110

Glu Asp Asp Thr Asp Gly Ala Glu Asp Phe Val Ser Glu Asn Ser Asn
        115                 120                 125

Asn Lys Arg Ala Pro Tyr Trp Thr Asn Thr Glu Lys Met Glu Lys Arg
    130                 135                 140

Leu His Ala Val Pro Ala Ala Asn Thr Val Lys Phe Arg Cys Pro Ala
145                 150                 155                 160

Gly Gly Asn Pro Met Pro Thr Met Arg Trp Leu Lys Asn Gly Lys Glu
                165                 170                 175

Phe Lys Gln Glu His Arg Ile Gly Gly Tyr Lys Val Arg Asn Gln His
            180                 185                 190

Trp Ser Leu Ile Met Glu Ser Val Val Pro Ser Asp Lys Gly Asn Tyr
        195                 200                 205

Thr Cys Val Val Glu Asn Glu Tyr Gly Ser Ile Asn His Thr Tyr His
    210                 215                 220

Leu Asp Val Val Glu Arg Ser Pro His Arg Pro Ile Leu Gln Ala Gly
225                 230                 235                 240
```

-continued

Leu Pro Ala Asn Ala Ser Thr Val Val Gly Gly Asp Val Glu Phe Val
                245                 250                 255

Cys Lys Val Tyr Ser Asp Ala Gln Pro His Ile Gln Trp Ile Lys His
            260                 265                 270

Val Glu Lys Asn Gly Ser Lys Tyr Gly Pro Asp Gly Leu Pro Tyr Leu
        275                 280                 285

Lys Val Leu Lys Ala Ala Gly Val Asn Thr Thr Asp Lys Glu Ile Glu
    290                 295                 300

Val Leu Tyr Ile Arg Asn Val Thr Phe Glu Asp Ala Gly Glu Tyr Thr
305                 310                 315                 320

Cys Leu Ala Gly Asn Ser Ile Gly Ile Ser Phe His Ser Ala Trp Leu
            325                 330                 335

Thr Val Leu Pro Ala Pro Gly Arg Glu Lys Glu Ile Thr Ala Ser Pro
        340                 345                 350

Asp Tyr Leu Glu Ile Ala Ile Tyr Cys Ile Gly Val Phe Leu Ile Ala
    355                 360                 365

Cys Met Val Val Thr Val Ile Leu Cys Arg Met Lys Asn Thr Thr Lys
    370                 375                 380

Lys Pro Asp Phe Ser Ser Gln Pro Ala Val His Lys Leu Thr Lys Arg
385                 390                 395                 400

Ile Pro Leu Arg Arg Gln Val Thr Val Ser Ala Glu Ser Ser Ser Ser
            405                 410                 415

Met Asn Ser Asn Thr Pro Leu Val Arg Ile Thr Thr Arg Leu Ser Ser
        420                 425                 430

Thr Ala Asp Thr Pro Met Leu Ala Gly Val Ser Glu Tyr Glu Leu Pro
    435                 440                 445

Glu Asp Pro Lys Trp Glu Phe Pro Arg Asp Lys Leu Thr Leu Gly Lys
450                 455                 460

Pro Leu Gly Glu Gly Cys Phe Gly Gln Val Val Met Ala Glu Ala Val
465                 470                 475                 480

Gly Ile Asp Lys Asp Lys Pro Lys Glu Ala Val Thr Val Ala Val Lys
            485                 490                 495

Met Leu Lys Asp Asp Ala Thr Glu Lys Asp Leu Ser Asp Leu Val Ser
        500                 505                 510

Glu Met Glu Met Met Lys Met Ile Gly Lys His Lys Asn Ile Ile Asn
    515                 520                 525

Leu Leu Gly Ala Cys Thr Gln Asp Gly Pro Leu Tyr Val Ile Val Glu
    530                 535                 540

Tyr Ala Ser Lys Gly Asn Leu Arg Glu Tyr Leu Arg Ala Arg Arg Pro
545                 550                 555                 560

Pro Gly Met Glu Tyr Ser Tyr Asp Ile Asn Arg Val Pro Glu Glu Gln
            565                 570                 575

Met Thr Phe Lys Asp Leu Val Ser Cys Thr Tyr Gln Leu Ala Arg Gly
        580                 585                 590

Met Glu Tyr Leu Ala Ser Gln Lys Cys Ile His Arg Asp Leu Ala Ala
    595                 600                 605

Arg Asn Val Leu Val Thr Glu Asn Asn Val Met Lys Ile Ala Asp Phe
    610                 615                 620

Gly Leu Ala Arg Asp Ile Asn Asn Ile Asp Tyr Tyr Lys Lys Thr Thr
625                 630                 635                 640

Asn Gly Arg Leu Pro Val Lys Trp Met Ala Pro Glu Ala Leu Phe Asp
            645                 650                 655

-continued

```
Arg Val Tyr Thr His Gln Ser Asp Val Trp Ser Phe Gly Val Leu Met
            660             665             670

Trp Glu Ile Phe Thr Leu Gly Gly Ser Pro Tyr Pro Gly Ile Pro Val
        675             680             685

Glu Glu Leu Phe Lys Leu Leu Lys Glu Gly His Arg Met Asp Lys Pro
    690             695             700

Ala Asn Cys Thr Asn Glu Leu Tyr Met Met Met Arg Asp Cys Trp His
705             710             715             720

Ala Val Pro Ser Gln Arg Pro Thr Phe Lys Gln Leu Val Glu Asp Leu
                725             730             735

Asp Arg Ile Leu Thr Leu Thr Thr Asn Glu Glu Tyr Leu Asp Leu Ser
            740             745             750

Gln Pro Leu Glu Gln Tyr Ser Pro Ser Tyr Pro Asp Thr Arg Ser Ser
        755             760             765

Cys Ser Ser Gly Asp Asp Ser Val Phe Ser Pro Asp Pro Met Pro Tyr
    770             775             780

Glu Pro Cys Leu Pro Gln Tyr Pro His Ile Asn Gly Ser Val Lys Thr
785             790             795             800
```